US011266394B2

(12) United States Patent
Widenhouse et al.

(10) Patent No.: US 11,266,394 B2
(45) Date of Patent: Mar. 8, 2022

(54) METHODS AND DEVICES FOR PROVIDING ACCESS INTO A BODY CAVITY

(71) Applicant: Ethicon LLC, Guaynabo, PR (US)

(72) Inventors: Christopher W. Widenhouse, Clarksville, OH (US); Frederick E. Shelton, IV, Hillsboro, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 231 days.

(21) Appl. No.: 16/663,808

(22) Filed: Oct. 25, 2019

(65) Prior Publication Data
US 2020/0060672 A1 Feb. 27, 2020

Related U.S. Application Data

(60) Continuation of application No. 16/027,907, filed on Jul. 5, 2018, now Pat. No. 10,470,751, which is a
(Continued)

(51) Int. Cl.
A61B 17/02 (2006.01)
A61B 17/34 (2006.01)
A61B 17/00 (2006.01)

(52) U.S. Cl.
CPC ...... A61B 17/0218 (2013.01); A61B 17/3423 (2013.01); A61B 17/3462 (2013.01);
(Continued)

(58) Field of Classification Search
CPC ............ A61B 17/0218; A61B 17/3423; A61B 17/3462; A61B 2017/00862;
(Continued)

(56) References Cited

U.S. PATENT DOCUMENTS 3,402,710 A 9/1968 Paleschuck
3,654,965 A 4/1972 Gramain
(Continued)

FOREIGN PATENT DOCUMENTS

EP 0568383 A1 11/1993
EP 0646358 A1 4/1995
(Continued)

OTHER PUBLICATIONS

European Search Report issued in European Application No. 10250399.2 dated Apr. 28, 2010.
(Continued)

Primary Examiner — Pedro Philogene
(74) Attorney, Agent, or Firm — Mintz Levin Cohn Ferris Glovsky and Popeo, P.C.

(57) ABSTRACT

Methods and devices are provided for providing surgical access into a body cavity. In one embodiment, a surgical access device is provided that includes a housing coupled to a retractor. The housing can be have one or more movable sealing ports for receiving surgical instruments. Each movable sealing port can include one or more sealing elements therein for sealing the port and/or forming a seal around a surgical instrument disposed therethrough. Each movable sealing port can be rotatable relative to the housing and each sealing element can be rotatable relative to the housing along a predetermined orbital path.

20 Claims, 45 Drawing Sheets

Related U.S. Application Data division of application No. 15/145,954, filed on May 4, 2016, now Pat. No. 10,039,542, which is a continuation of application No. 14/571,457, filed on Dec. 16, 2014, now Pat. No. 9,351,717, which is a continuation of application No. 12/399,625, filed on Mar. 6, 2009, now Pat. No. 8,926,506.

(52) U.S. Cl.
CPC ............ *A61B 2017/00862* (2013.01); *A61B 2017/3419* (2013.01); *A61B 2017/3445* (2013.01); *A61B 2017/3447* (2013.01); *A61B 2017/3449* (2013.01); *A61B 2017/3464* (2013.01); *A61B 2017/3466* (2013.01)

(58) Field of Classification Search
CPC .... A61B 2017/3419; A61B 2017/3445; A61B 2017/3447; A61B 2017/3449; A61B 2017/3464; A61B 2017/3466
See application file for complete search history.

(56) References Cited

U.S. PATENT DOCUMENTS

| | | |
|---|---|---|
| 4,112,932 A | 9/1978 | Chiulli |
| 4,306,545 A | 12/1981 | Ivan et al. |
| 2,129,391 A | 9/1983 | Frederick |
| 4,402,683 A | 9/1983 | Kopman |
| 4,417,888 A | 11/1983 | Cosentino et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,269,772 A | 12/1993 | Wilk |
| 5,308,336 A | 5/1994 | Hart et al. |
| 5,330,437 A | 7/1994 | Durman |
| 5,366,478 A | 11/1994 | Brinkerhoff et al. |
| 5,375,588 A | 12/1994 | Yoon |
| 5,385,553 A | 1/1995 | Hart et al. |
| 5,385,560 A | 1/1995 | Wulf |
| 5,391,154 A | 2/1995 | Young |
| 5,443,452 A | 8/1995 | Hart et al. |
| 5,443,484 A | 8/1995 | Kirsch et al. |
| 5,480,410 A | 1/1996 | Cuschieri et al. |
| 5,531,758 A | 7/1996 | Uschold et al. |
| 5,545,179 A | 8/1996 | Williamson, IV |
| 5,569,205 A | 10/1996 | Hart et al. |
| 5,569,254 A | 10/1996 | Carlson et al. |
| 5,584,850 A | 12/1996 | Hart et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,672,168 A | 9/1997 | de la Torre et al. |
| 5,676,657 A | 10/1997 | Yoon |
| 5,695,448 A | 12/1997 | Kimura et al. |
| 5,782,812 A | 7/1998 | Hart et al. |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,891,013 A | 4/1999 | Thompson |
| 5,906,577 A | 5/1999 | Beane et al. |
| 5,957,913 A | 9/1999 | de la Torre et al. |
| 5,990,382 A | 11/1999 | Fox |
| 6,024,736 A | 2/2000 | de la Torre et al. |
| RE36,702 E | 5/2000 | Green et al. |
| 6,077,288 A | 6/2000 | Shimomura et al. |
| 6,086,603 A | 7/2000 | Termin et al. |
| 6,120,513 A | 9/2000 | Bailey et al. |
| 6,123,689 A | 9/2000 | To et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,315,770 B1 | 11/2001 | de la Torre et al. |
| 6,319,246 B1 | 11/2001 | de la Torre et al. |
| 6,348,034 B1 | 2/2002 | Thompson |
| 6,352,503 B1 | 3/2002 | Matsui et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,706,033 B1 | 3/2004 | Martinez et al. |
| 6,706,050 B1 | 3/2004 | Giannadakis |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,214,185 B1 | 5/2007 | Rosney et al. |
| 7,338,473 B2 | 3/2008 | Campbell et al. |
| 7,344,547 B2 | 3/2008 | Piskun |
| 8,092,430 B2 | 1/2012 | Richard et al. |
| 8,187,178 B2 * | 5/2012 | Bonadio ............ A61B 17/3498 600/208 |
| 8,328,761 B2 | 12/2012 | Widenhouse et al. |
| 8,425,410 B2 | 4/2013 | Murray et al. |
| 8,430,811 B2 | 4/2013 | Hess et al. |
| 8,485,970 B2 | 7/2013 | Widenhouse et al. |
| 8,821,391 B2 | 9/2014 | Widenhouse et al. |
| 8,926,506 B2 | 1/2015 | Widenhouse et al. |
| 9,351,717 B2 | 5/2016 | Widenhouse et al. |
| 2002/0156432 A1 | 10/2002 | Racenet et al. |
| 2003/0028179 A1 | 2/2003 | Piskun |
| 2003/0139756 A1 | 7/2003 | Brustad |
| 2004/0015185 A1 | 1/2004 | Ewers et al. |
| 2004/0106942 A1 | 6/2004 | Taylor et al. |
| 2004/0138528 A1 | 7/2004 | Richter et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0020241 A1 | 1/2006 | Piskun et al. |
| 2006/0020281 A1 | 1/2006 | Smith |
| 2006/0071432 A1 | 4/2006 | Staudner |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247673 A1 | 11/2006 | Voegele et al. |
| 2006/0264706 A1 | 11/2006 | Piskun |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0118021 A1 | 5/2007 | Pokorney |

(56) References Cited

U.S. PATENT DOCUMENTS

| | | |
|---|---|---|
| 2007/0151566 A1 | 7/2007 | Kahle et al. |
| 2007/0185453 A1 | 8/2007 | Michael et al. |
| 2007/0208312 A1 | 9/2007 | Norton et al. |
| 2007/0255219 A1 | 11/2007 | Vaugh et al. |
| 2008/0027476 A1 | 1/2008 | Piskun |
| 2008/0051739 A1 | 2/2008 | McFarlane |
| 2008/0065021 A1 | 3/2008 | Jenkins et al. |
| 2008/0119821 A1 | 5/2008 | Agnihotri et al. |
| 2008/0161826 A1 | 7/2008 | Guiraudon |
| 2008/0255519 A1 | 10/2008 | Piskun et al. |
| 2009/0005799 A1 | 1/2009 | Franer et al. |
| 2009/0221966 A1 | 9/2009 | Richard |
| 2009/0227843 A1 | 9/2009 | Smith et al. |
| 2009/0287163 A1 | 11/2009 | Fischvogt et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0113886 A1 | 5/2010 | Piskun et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0274093 A1 | 10/2010 | Shelton, IV |
| 2011/0028793 A1 | 2/2011 | Martin et al. |
| 2011/0028794 A1 | 2/2011 | Widenhouse et al. |
| 2015/0099938 A1 | 4/2015 | Widenhouse et al. |
| 2016/0242758 A1 | 8/2016 | Widenhouse et al. |
| 2018/0317901 A1 | 11/2018 | Widenhouse et al. |

FOREIGN PATENT DOCUMENTS

| | | |
|---|---|---|
| EP | 0776231 A1 | 6/1997 |
| EP | 0950376 A1 | 10/1999 |
| EP | 1219251 A1 | 7/2002 |
| EP | 1219252 A1 | 7/2002 |
| EP | 1219253 A1 | 7/2002 |
| EP | 1350476 A1 | 10/2003 |
| EP | 1731105 A1 | 12/2006 |
| EP | 2119404 A1 | 11/2009 |
| EP | 2168512 A1 | 3/2010 |
| FR | 2710270 | 3/1995 |
| FR | 2904210 A1 | 2/2008 |
| JP | 2006320750 A | 11/2006 |
| WO | WO-96002297 A1 | 2/1996 |
| WO | WO-0217800 A2 | 3/2002 |
| WO | WO-05087112 A1 | 9/2005 |
| WO | WO-05094432 A2 | 10/2005 |
| WO | WO-07119232 A2 | 10/2007 |
| WO | WO-08024502 A2 | 2/2008 |
| WO | WO-08121294 A1 | 10/2008 |

OTHER PUBLICATIONS

European Search Report issued in European Application No. 10250401.6 dated May 21, 2010.

* cited by examiner

FIG. 5
FIG. 6
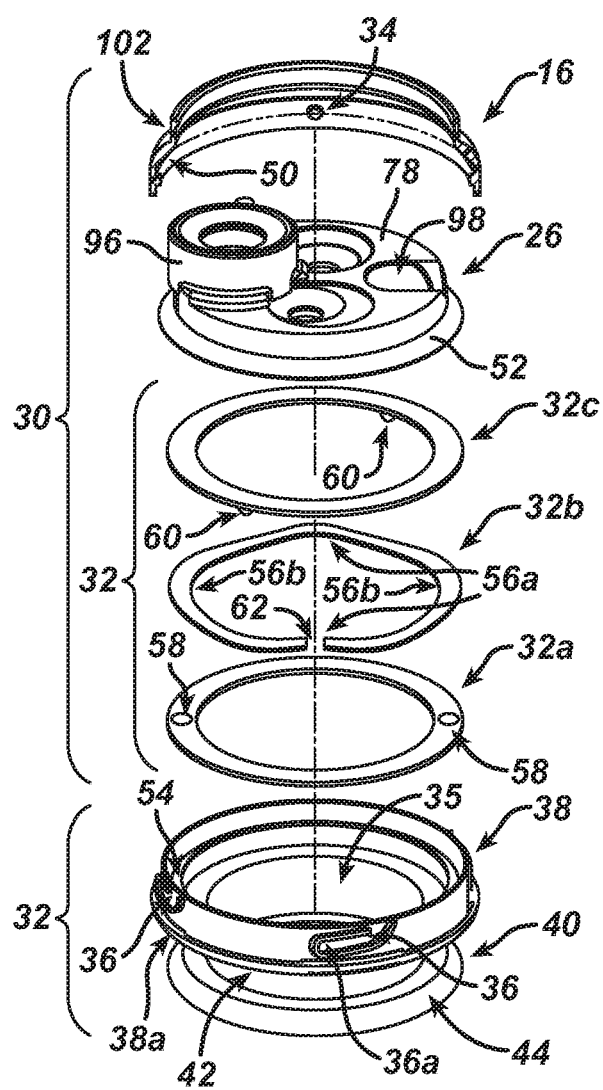
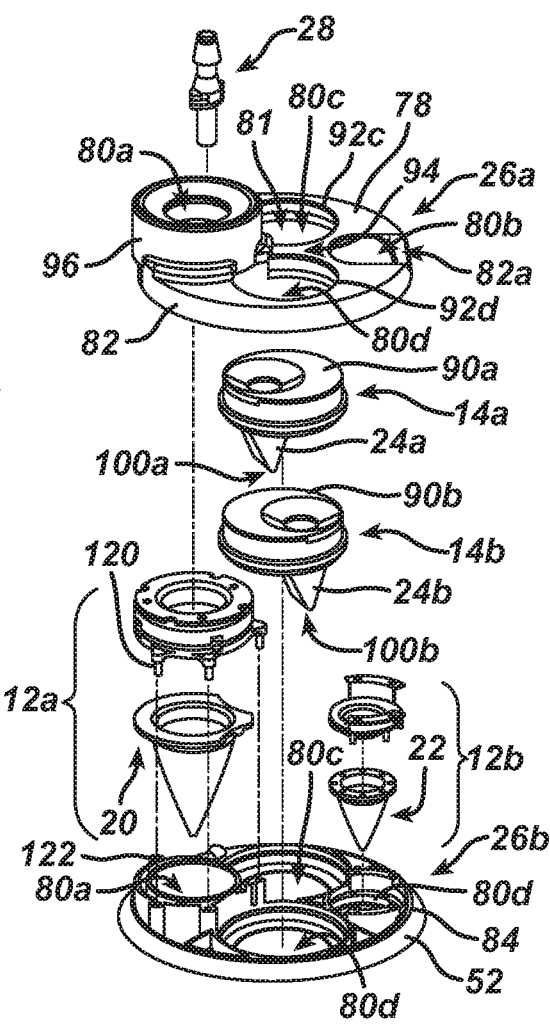

METHODS AND DEVICES FOR PROVIDING ACCESS INTO A BODY CAVITY

CROSS REFERENCES

The present application is a continuation of U.S. patent application Ser. No. 16/027,907 (now U.S. Pat. No. 10,470,751) entitled "Methods and Devices for Providing Access into a Body Cavity," filed on Jul. 5, 2018, which is a divisional of U.S. patent application Ser. No. 15/145,954 (now U.S. Pat. No. 10,039,542) entitled "Methods and Devices for Providing Access into a Body Cavity," filed on May 4, 2016, which is a continuation of U.S. patent application Ser. No. 14/571,457 (now U.S. Pat. No. 9,351,717) entitled "Methods and Devices for Providing Access into a Body Cavity," filed Dec. 16, 2014, which is a continuation of U.S. patent application Ser. No. 12/399,625 (now U.S. Pat. No. 8,926,506) entitled "Methods and Devices for Providing Access into a Body Cavity," filed Mar. 6, 2009, which are hereby incorporated by reference in their entireties.

FIELD OF THE INVENTION

The present invention relates to methods and devices for providing surgical access into a body cavity.

BACKGROUND OF THE INVENTION

Abdominal laparoscopic surgery gained popularity in the late 1980s, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through a the trocar sleeve. Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. Instruments used for mini-laparoscopic procedures are, however, generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller 2-3 mm incisions may still cause undesirable cosmetic outcomes and wound complications (bleeding, infection, pain, keloid formation, etc.).

Since the benefits of smaller and fewer body cavity incisions are proven, it would be desirable to perform an operation utilizing only a single incision. An umbilicus is well-hidden and the thinnest and least vascularized area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. One drawback with entry through the umbilicus, however, is that the placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems which allow laparoscopic procedures to be performed entirely through the umbilicus or a surgical port located elsewhere while at the same time reducing or eliminating the "chopstick effect."

SUMMARY OF THE INVENTION

The present invention generally provides methods and devices for providing surgical access into a body cavity. In one embodiment, a surgical access device is provided that includes a housing having a working channel extending therethrough, and a base coupled to the housing and having first and second sealing elements. The base is configured to rotate relative to the housing, and the first and second sealing elements are each configured to receive an instrument inserted therethrough and into the working channel. Each of the first and second sealing elements are movable independent of another of the first and second sealing elements in a predetermined orbital path.

The first and second sealing elements and the predetermined orbital paths in which they are movable can have any number of variations. For example, each of the first and second sealing elements can be laterally movable in a predetermined orbital path. For another example, the first sealing element with a surgical instrument held in a substantially fixed position therein can be configured to move in a predetermined orbital path in response to movement of the second sealing element in a predetermined orbital path. For yet another example, the predetermined orbital paths of the first and second sealing elements can each have a central axis that is offset from a central axis of the base. For still another example, each of the first and second sealing elements can be disposed within a support that is rotatably disposed within the base, each sealing element being eccentric relative to its respective support. In some embodiments, each of the first and second sealing elements can each be configured to provide a fluid seal with no instrument inserted therethrough.

The device can vary in any other number of ways. For example, the base can include first and second cut-outs formed therein, and perimeters of the first and second cut-outs can respectively define the predetermined orbital paths of the first and second sealing elements. In some embodiments, the device can include a side access port formed in a proximal retractor base configured to be coupled to the housing and configured to receive an instrument inserted therethrough. The side access port can extend in a plane that is offset from a plane containing the base. For yet another example, the device can include a retractor fixedly or rotatably coupled to the housing. The retractor can have a retractor shield disposed therein.

In some embodiments the device can include at least one fixed sealing element fixedly disposed within the base and configured to remain in a fixed position relative to the base. The first and second sealing elements and the at least one fixed sealing element can be positioned radially around a central axis of the base. The at least one fixed sealing element can be disposed in a plane offset from and parallel to a plane containing the first and second sealing elements. The device can include first and second fixed sealing elements, the first fixed sealing element being positioned below a plane containing the first and second sealing elements and the second fixed sealing element being positioned above the plane containing the first and second sealing elements.

In yet another embodiment, a surgical access device is provided that includes a housing defining a working channel. The housing has a base, a support rotatably disposed in the base, and a sealing element disposed in the support at a location offset from a central rotational axis of the support. The sealing element is configured to receive a surgical instrument inserted therethrough and into the working channel. In some embodiments, the housing can have a second support rotatably disposed in the base and a second sealing element disposed at a location offset from a central rotational axis of the second support. The second sealing element can be configured to receive a surgical instrument inserted therethrough and into the working channel. The central rotational axis of the second support can be offset from the central rotational axis of the first support. The sealing element with a surgical instrument held in a substantially fixed position therein can be configured to move in a predetermined orbital path in response to movement of the second sealing element in a predetermined orbital path. The device can have any number of variations. For example, the central rotational axis of the support is offset from a central axis of the base. For another example, the base has at least one fixed sealing element that is configured to remain in a fixed position relative to the base and to move with the base relative to the housing.

In yet another embodiment, a surgical access device is provided that includes a housing having a base rotatably coupled thereto. The base has a plurality of sealing elements including at least one movable sealing element configured to form a seal around an instrument inserted therethrough and being rotatable relative to the base independent of the other sealing elements. Rotation of the at least one movable sealing element relative to the base is effective to change a distance of the at least one movable sealing element from a center-point of the base. In some embodiments, the base can have first and second movable sealing elements. The device can have any number of variations. For example, the base can be circular-shaped and configured to rotate around the center-point of the base. For another example, the at least one movable sealing element can be rotatable in a plane of the base. In some embodiments, the device can include a flexible retractor coupled to the housing. A side access port can be formed in a proximal retractor base of the retractor and configured to receive a retractor inserted therethrough. The base can be configured to rotate relative to the side access port. For another example, the housing can define a working channel extending therethrough between a proximal end of the housing and a distal end of the housing. The base can be located at a proximal end of the housing such that instruments inserted through the sealing elements extend through the working channel. The at least one movable sealing elements can be disposed within a support that is rotatably disposed within a predefined shape formed in the base, the at least one movable sealing element being eccentric relative to its support. The center-point of the base can be spaced apart from the predefined shapes.

In another aspect, a method of providing access through tissue to a body cavity is provided. The method includes positioning a surgical access device within an opening formed through tissue such that the surgical access device forms a working channel extending through the tissue and into a body cavity, inserting a first surgical instrument through a first sealing element in the surgical access device and through the working channel of the surgical access device to position a distal end of the first surgical instrument within the body cavity, and moving the first surgical instrument to cause the first sealing element to move along an orbital path from a first position, in which the first sealing element is located a first distance from a center-point of the surgical access device, to a second position, in which the first sealing element is located a second distance from the center-point of the surgical access device that is different from the first distance. The method can have any number of variations. For example, moving the first surgical instrument can cause rotation of a base of the surgical access device that is coupled to the housing. The rotation of the base can cause a second sealing element in the surgical access device having a second surgical instrument inserted therethrough to move along an orbital path from a third position, in which the second sealing element is located a third distance from the center-point of the surgical access device, to a fourth position, in which the second sealing element is located a fourth distance from the center-point of the surgical access device that is different from the third distance. For another example, the working channel can extend through a housing of the surgical access device, and moving the first surgical instrument can cause a base of the surgical access device that is coupled to the housing to rotate relative to the housing.

BRIEF DESCRIPTION OF THE DRAWINGS

The invention will be more fully understood from the following detailed description taken in conjunction with the accompanying drawings, in which:

FIG. 5 is a partial cross-sectional, exploded view of the device of FIG. 1;

FIG. 6 is an exploded view of a seal base and sealing ports of the device of FIG. 1;

DETAILED DESCRIPTION OF THE INVENTION

Figure 1:
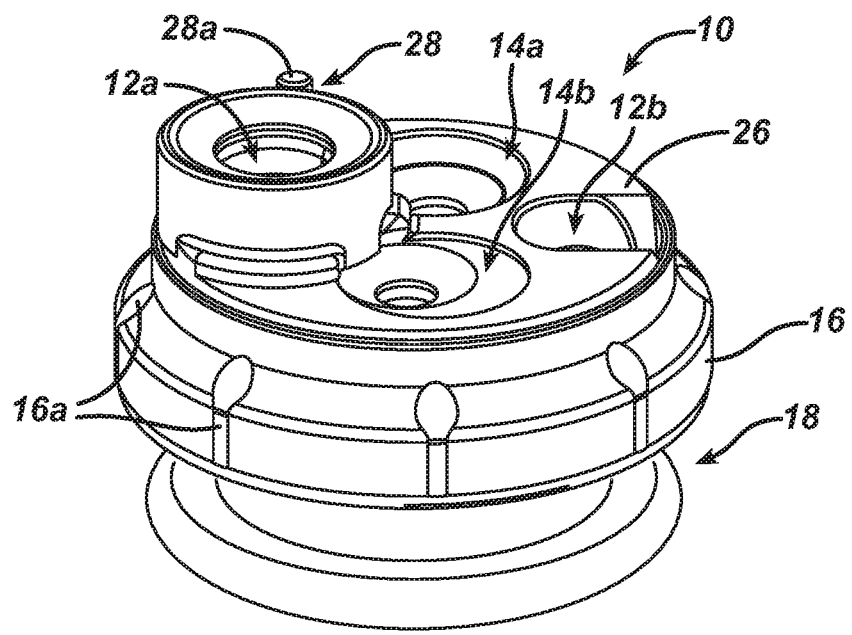
FIG. 1 is a perspective view of one embodiment of a surgical access device having first and second fixed sealing ports and first and second movable sealing ports extending therethrough.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for providing surgical access into a body cavity. In general, the methods and devices allow multiple surgical instruments to be inserted through independent access ports in a single surgical access device and into a body cavity. The instruments can be collectively rotatable about a central axis of the device, and they can be independently movable with respect to one another, thus allowing for ease of manipulation within a patient's body. In one embodiment, a surgical access device includes a housing having one or more movable access ports or movable sealing ports for receiving surgical instruments. Each movable sealing port can include one or more sealing elements therein for sealing the port and/or forming a seal around a surgical instrument disposed therethrough. The movable sealing ports can each be rotatable relative to the housing and the sealing elements can move around a predetermined orbital path, thereby allowing instruments inserted therethrough and into the body cavity to be optimally positioned. This can help avoid the "chopstick effect" and provide increased working space for instruments within the body cavity. The movable sealing ports can also be configured such that movement of a first surgical instrument inserted through a first movable sealing port can cause movement of a second movable sealing port to allow a second surgical instrument inserted through the second movable sealing port to remain in a fixed position, which can help optimally position the instruments with respect to each other.

The various surgical access devices can also include a wound protector, cannula, ring retractor, or other member for forming a pathway through tissue (hereinafter generally referred to as a retractor). The retractor can extend from the housing and it can be configured to be positioned within an opening in a patient's body, such as the umbilicus. The sealing ports can each define working channels extending through the housing and aligned with the retractor. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

As discussed further below, any and all embodiments of a surgical access device can also include one or more safety shields positioned through, in, and around any of the components and/or tissue to protect the components against puncture or tear by surgical instruments being inserted through the device. In addition, any and all embodiments of a surgical access device can include engagement and release mechanisms that allow certain components of the surgical access device to be removable as needed.

In use, and as also further discussed below, the surgical access devices disclosed herein can be used to provide access to a patient's body cavity. The retractor can be positionable within an opening in a patient's body such that a distal portion of the retractor extends into a patient's body cavity and a proximal portion configured to couple to a housing is positioned adjacent to the patient's skin on an exterior of the patient's body. A lumen in the retractor can form a pathway through the opening in a patient's body so that surgical instruments can be inserted from outside the body to an interior body cavity. The elasticity of the skin of the patient can assist in the retention of the retractor in the body opening or incision made in the body. The retractor can be placed in any opening within a patient's body, whether a natural orifice or an opening made by an incision. In one embodiment, the retractor can be substantially flexible so that it can easily be maneuvered into and within tissue as needed. In other embodiments, the retractor can be substantially rigid or substantially semi-rigid. The retractor can be formed of any suitable material known in the art, e.g., silicone, urethane, thermoplastic elastomer, and rubber.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel created by the sealing port when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment.

In an exemplary embodiment, shown in FIGS. 1-6, a surgical access device 10 includes at least one fixed sealing port and at least one movable sealing port. The surgical access device 10 can have a housing 16 removably coupled on one end to a seal base 26 that supports the fixed and movable sealing ports on another end and to a retractor 18 configured to distally extend from the housing 16. While any number of fixed and movable sealing ports can be formed in the seal base 26, in this illustrated embodiment, first and second fixed sealing ports 12a, 12b and first and second movable sealing ports 14a, 14b extend through the seal base 26. The base 26 can be movable with respect to the housing 16 and the retractor 18, and the first and second movable sealing ports 14a, 14b can be movable with respect to the base 26, the housing 16, the retractor 18, and each other, as will be discussed in more detail below. Such a configuration can help prevent interference between surgical instruments inserted through various ones of the sealing ports 12a, 12b, 14a, 14b, and can facilitate instrument positioning in a body cavity to which the device 10 provides access.

The device 10 can also include an insufflation port 28 supported by the base 26, although a person skilled in the art will appreciate that the insufflation port 28 can be located in the housing 16 or in other locations. A person skilled in the art will also appreciate that the insufflation port 28 can have a variety of configurations. Generally, the insufflation port 28 can be configured to pass an insufflation fluid through an insufflation orifice 28a of the insufflation port 28 into and/or out of a body cavity to which the device 10 provides access.

A proximal portion 30 of the surgical access device 10 can, as shown, include the seal base 26, the housing 16 in the form of a lock ring configured to releasably attach the base 26 to the retractor 18, and a spring assembly 32 configured to be disposed between the seal base 26 and the lock ring 30 to form a seat and seal between the base 26 and a distal portion of the device 10, e.g., the retractor 18. The retractor 18, the seal base 26, the housing 30, and the spring assembly 32 can each have various sizes, shapes, and configurations, as discussed further below.

As noted above, the retractor 18 can extend from the housing 16, and it can be configured to be positioned in an opening formed in tissue. The retractor 18 can, as shown in this exemplary embodiment, be a substantially flexible member having a proximal flange 46 and a distal flange 40 with an inner elongate portion 42 extending therebetween. The inner elongate portion 42 can have a diameter less than a diameter of the proximal and distal flanges 46, 40, which can have the same diameter or different diameters from one another. The proximal flange 46 can be configured to be seated within a proximal retractor base 38 in a proximal portion of the retractor 18 and optionally attached thereto using an adhesive, sealant, complementary threads, or any other attachment mechanism, as will be appreciated by a person skilled in the art. A proximal o-ring 48 can be optionally positioned within the proximal flange 46 to help provide structural support to the retractor 18 within the proximal retractor base 38. A distal o-ring 44 can optionally be positioned within the distal flange 40 to provide structural support to the retractor 18 within a patient's body. The proximal and distal o-rings 48, 44 can be substantially flexible or substantially rigid as needed, same or different from one another, for use in a particular application.

The housing 16 can, as illustrated, be a substantially rigid cylindrical or circular member and can have a proximal circumferential sidewall with a diameter less than a diameter of a distal circumferential sidewall of the housing 16. A middle connecting circumferential sidewall 50 can extend between the proximal and distal sidewalls at an angle radially outward from the proximal and distal sidewalls. The middle sidewall 50 can have a size and shape corresponding to a complementary lip 52 formed on and extending radially outward from the seal base 26 such that the middle sidewall 50 can be configured to engage the lip 52 and movably couple the seal base 26 to the housing 16 and the retractor 18 when the housing 16 is attached to the retractor 18.

While any engagement and release mechanism known in the art can be used to releasably mate the housing 16 and the retractor 18 together, as illustrated in the embodiment shown in FIGS. 1-5, the device 10 can include an engagement and release mechanism in the form of a bayonet latch mechanism. At least one bayonet foot or pin, e.g., four radially arranged bayonet feet or pins 34 spaced equidistantly or any other distance apart, can extend any length from an inner circumference of the housing 16, e.g., from the distal sidewall, and they can be configured to engage corresponding slots 36 formed in an outer surface of the proximal retractor base 38. The bayonet pins 34 on the housing 16 can be lowered into the slots 36 in the proximal retractor base 38. The housing 16 can then be rotated in a first direction, e.g., a clockwise direction, relative to the retractor 18, thereby causing the bayonet pins 34 to travel laterally within the slots 36 to a position in which the pins 34 abut terminal ends 36a of the slots 36, thereby locking the housing 16 to the retractor 18. One or more of the slots 36 can angle proximally or distally (not shown) at their respective terminal ends 36a such that the bayonet pins 34 can proximally or distally slide and snap into the terminal ends 36a to help ensure that the bayonet pins 34 fully slide through the slots 36 to lock the housing 16 to the retractor 18. The housing 16 can optionally include surface features 16a, e.g., ridges, bumps, textured surface, etc., to help facilitate gripping and turning of the housing 16. If disengagement of the housing 16 and the retractor 18 is desired, e.g., to replace the seal base 26 with another seal base having a different number or different sizes of sealing ports or to replace the retractor 18, the housing 16 can be rotated in the second, opposite direction such that the bayonet pins 34 are free to be withdrawn from the slots 36.

With the housing 16 locked to the proximal retractor base 38, the seal base 26 can be rotated in the first direction and in a second opposite direction, e.g., a counter clockwise direction, to rotate the seal base 26 relative to the housing 16 as well as to the retractor 18. While the base 26 can be configured to be rotatable relative to the housing 16 and the retractor 18 in only one of the first and second directions, the base 26 as illustrated is rotatable in both the first and second directions, which can help more effectively position surgical instruments inserted through the seal base 26 with respect to each other.

As indicated above, the spring assembly 32 can be positioned between the seal base 26 and the retractor 18. More particularly, the spring assembly 32 can be coupled between a distal surface of the base's lip 52 and an interior ledge 54 of the proximal retractor base 38. The interior ledge 54 can continuously run circumferentially around the proximal retractor base 38 as shown, or the interior ledge 54 can run around one or more discrete portions of the proximal retractor base 38.

Although the spring assembly 32 can have a variety of sizes, shapes, and configurations as mentioned above, the spring assembly 32 can, as shown, include distal and proximal spring retaining rings 32a, 32c with a seal spring 32b positioned therebetween. To help provide resiliency to the spring assembly 32, the seal spring 32b can be a substantially c-shaped ring having a cut-out 62 formed through one section of its circumference and can have a wavy configuration with alternating proximally extending portions 56a and distally extending portions 56b. The distal and proximal spring retaining rings 32a, 32c can each be a substantially circular ring and can each have a planar configuration but can be configured to engage both the proximally extending portions 56a and the distally extending portions 56b of the seal spring 32b. For non-limiting example, the distal and proximal spring retaining rings 32a, 32c can include respective hemispherical dimples 58, 60. The distal spring retaining ring's dimples 58 can be proximally facing and configured to engage and be positioned under the proximally extending portions 56a of the seal spring 32b, and the proximal spring retaining ring's dimples 60 can be distally facing and configured to engage and be positioned under the distally extending portions 56b of the seal spring 32b. In the illustrated embodiment, the seal spring 32b includes two proximally extending portions 56a and two distally extending portions 56b with the distal and proximal spring retaining rings 32a, 32c each including two dimples 58, 60 corresponding to their respective wavy portions of the seal spring 32b, but a person skilled in the art will appreciate that the seal spring 32b can have any number of proximally and distally extending portions with the distal and proximal spring retaining rings 32a, 32c having any number of corresponding dimples 58, 60 or other stabilizing mechanism. A person skilled in the art will also appreciate that the dimples 58, 60 can be same or different from any of the other simples 58, 60 and that they can each have any size and shape, e.g., hemispherical, a spherical segment, conical, box-shaped, etc. The generally circular shapes of the seal assembly's components can generally conform the shape of the seal assembly 32 to the curved shapes of the seal base 26 and the retractor 18 to which the seal assembly 32 can be mated. While the seal assembly 32 can be configured to prevent vertical movement, e.g., proximal and/or distal movement along the central axis of the working channel, of the base 26 with respect to the retractor 18, the dimples 58, 60 can allow the seal assembly 32 to provide for vertical movement of the base 26 relative to the retractor 18, which can help provide for smoother rotation of the base 26 with respect to the housing 16. The distal and proximal spring retaining rings 32a, 32c can be configured to rotate relative to one another, as shown in this embodiment, which can also help provide for smooth rotation of the base 26 relative to the housing 16. The distal and proximal spring retaining rings 32a, 32c and the seal spring 32b can each be configured to rotate relative to the other elements of the seal assembly 32, as illustrated.

Figure 14:
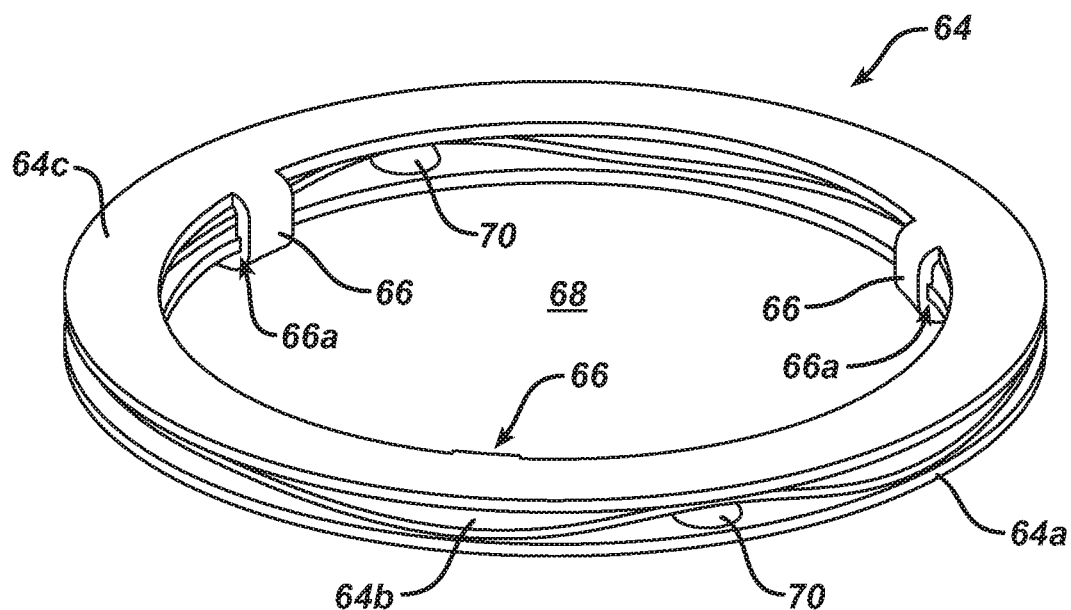
FIG. 14 is a perspective view of one embodiment of a seal assembly.

FIG. 14 illustrates an alternate embodiment of a seal assembly 64 that includes distal and proximal spring retaining rings 64a, 64c with a seal spring 64b positioned therebetween. The alternate seal assembly 64 is similar to the seal assembly 32 described above except that the alternate seal assembly 64 includes a locking mechanism configured to maintain the distal and proximal spring retaining rings 64a, 64c of the seal assembly 64 in a fixed radial position with respect to one another. The distal and proximal spring retaining rings 64a, 64c can be nevertheless be configured to be vertically movable with respect to one another, such as by including respective dimples 70 (only the distal spring retaining ring's dimples 70 are visible in FIG. 14) that engage wavy portions of the seal spring 64b, similar to that discussed above.

The seal assembly's locking mechanism can have a variety of configurations, and in this embodiment includes at least one tab 66. Although three radially arranged tabs 66 are spaced equidistantly apart around an inner circumference of the illustrated seal assembly 64, a person skilled in the art will appreciate that the seal assembly 64 can include any number of tabs 66 and that the tabs 64 can be arranged in any way. The tabs 66 include c-shaped clamps integrally formed with the proximal spring retaining ring 64c, although the tabs 66 can have any size, shape, and configuration and can be integrally formed with either or both of the spring retaining rings 64a, 64c or can be an independent element configured to couple to the spring retaining rings 64a, 64c. The tabs 66 extend from an inner circumference of the proximal spring retaining ring 64c, through an inner lumen 68 of the seal assembly 64, and to the distal spring retaining ring 64a. Positioning the locking mechanism substantially within the seal assembly's inner lumen 68 can help prevent the locking mechanism from impeding with the seal assembly's fit and rotation within the housing and the retractor to which the seal assembly 64 is mated. Each of the tabs 66 can mate to the distal spring retaining ring 64a with a notch 66a formed in a distal portion of the tab 66 that is configured to seat the distal spring retaining ring 64a therein. Although the tabs 66 are shown as identical to one another, each tab 66 can be the same or different from any other of the tabs 66. A seal assembly can include one or more types of locking mechanisms.

Figure 15:
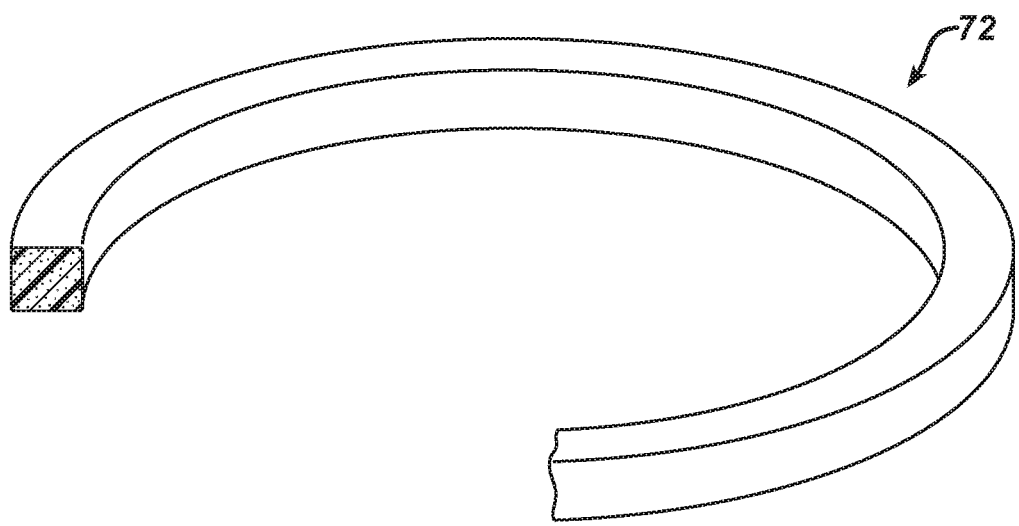
FIG. 15 is a partial cross-sectional view of one embodiment of a resilient seal assembly.
Figure 16:
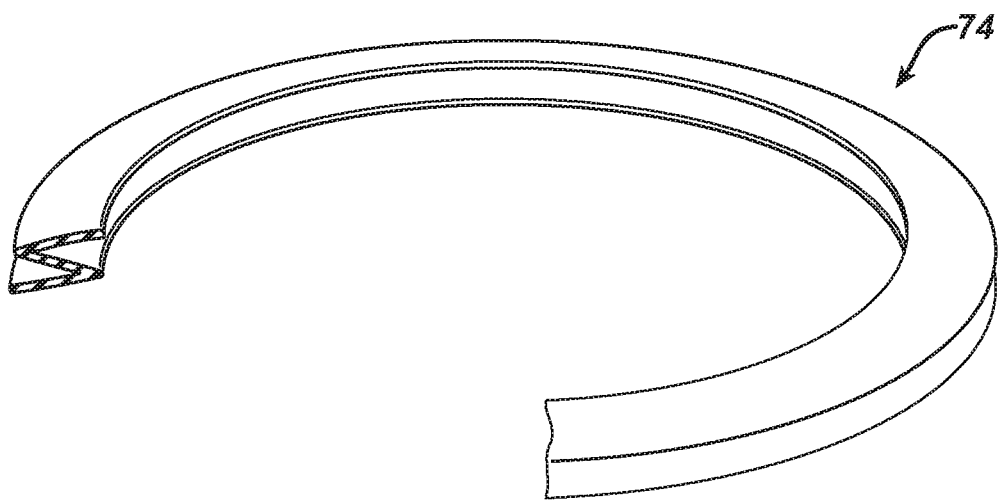
FIG. 16 is a partial cross-sectional view of another embodiment of a resilient seal assembly.
Figure 17:
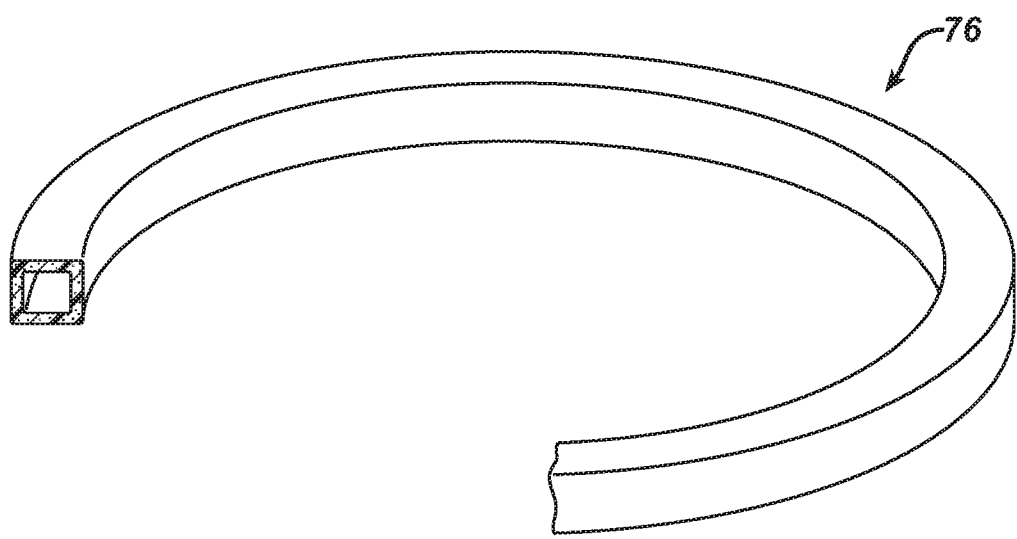
FIG. 17 is a partial cross-sectional view of one embodiment of a resilient seal assembly having a hollow interior.

While a surgical access device can include a seal assembly having multiple components, e.g., the seal assembly 32 of FIG. 5 and the seal assembly 64 of FIG. 14, in some embodiments a surgical access device can include a singular seal assembly configured to form a seat and seal between a seal base and a distal portion of a surgical access device to which the seal base is removably attached. FIG. 15 illustrates one embodiment of a singular seal member 72 in the form of a circular ring composed of a resilient foam material. Any resilient foam material can be used based on design choice for a particular spring rate, e.g., foamed polypropylene or polyethylene, sanoprene, and isoprene. The seal member 72 has a square cross-sectional shape, although the seal member can have any cross-sectional shape. For non-limiting example, as shown in FIG. 16, a singular seal member 74 composed of a resilient foam material and having a circular ring shape has a z-shaped cross-sectional shape. Although the singular seal members 72, 74 have solid cross-sections, in some embodiments, a singular seal member can have a hollow or partially hollow interior. FIG. 17 illustrates one embodiment of a hollow singular seal member 76 having a circular ring shape and a square cross-sectional shape with a square-shaped hollow interior.

The seal base 26 can have a variety of sizes, shapes, and configurations, as can the fixed and movable sealing ports 12a, 12b, 14a, 14b seated therein. As shown in FIG. 6, the seal base 26 can include proximal and distal base portions 26a, 26b configured to mate together with the first and second fixed sealing ports 12a, 12b and the first and second movable sealing ports 14a, 14b captured therebetween. The proximal base portion 26a can have a circular proximal surface 78 and a circumferential wall 82 extending distally from the proximal surface 78. The circumferential wall 82 can optionally include one or more cut-out portions 82a formed therein that are configured to help angle surgical instruments inserted through the base 26, as discussed further below. While any attachment or mating mechanism can be used to fixedly or removably mate the proximal and distal base portions 26a, 26b together, in the illustrated embodiment, an inner circumference of the proximal base portion 26a, e.g., an inner surface of the circumferential wall 82, can be configured to mate with an outer surface of a lip 84 proximally extending from the lip 52 formed on and extending from the distal base portion 26b. The proximal and distal base portions 26a, 26b can be fixedly attached together using an attachment mechanism, e.g., adhesive, sealant, etc., although as mentioned above, the proximal and distal base portions 26a, 26b can be removably attached together using an attachment mechanism, such as complementary threads. The proximal and distal base portions 26a, 26b can also or alternatively be held together by the housing 16.

Figure 7A:
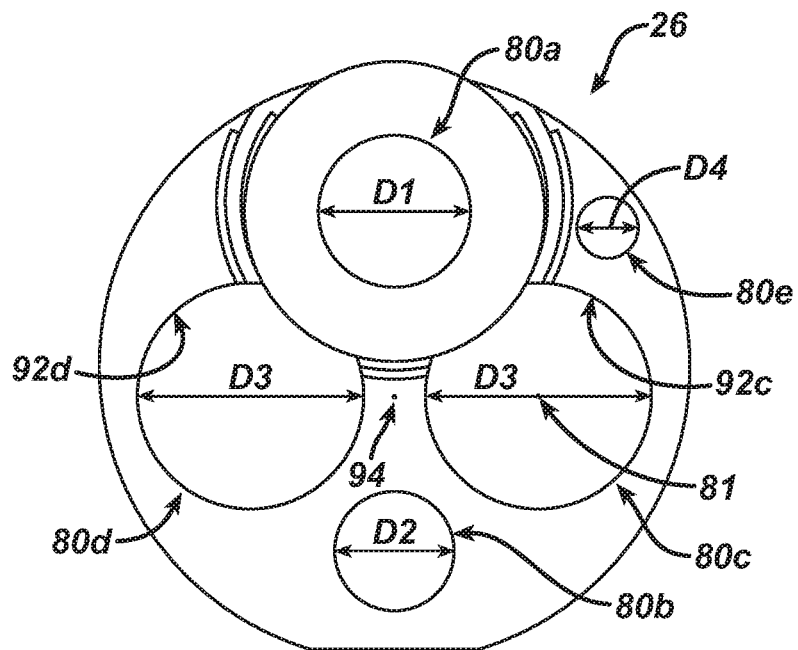
FIG. 7A is a top view of the seal base of the device of FIG. 1 without sealing ports extending through the seal base.
Figure 7B:
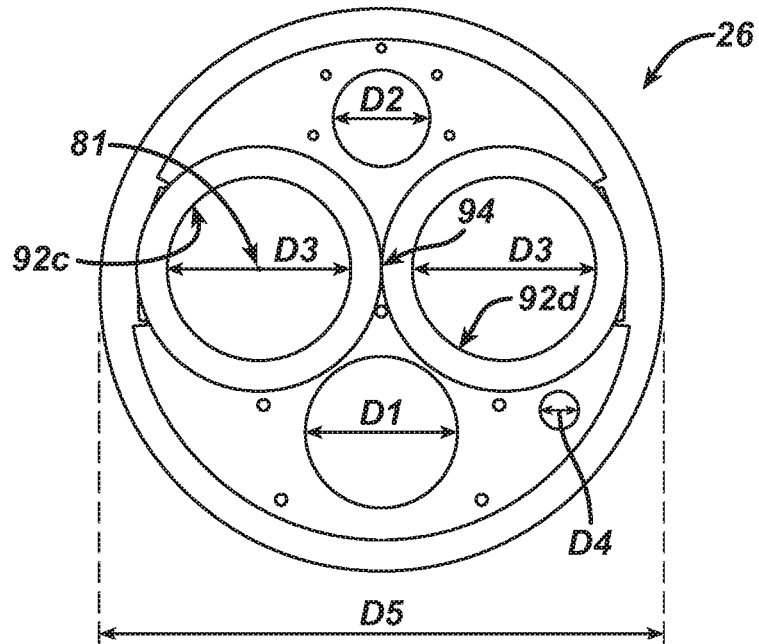
FIG. 7B is a bottom view of the seal base of the device of FIG. 1 without sealing ports extending through the seal base.

As shown in FIGS. 7A and 7B, first, second, third, and fourth port cut-outs or openings 80a, 80b, 80c, 80d can be formed through the seal base 26, e.g., through both the proximal and distal base portions 26a, 26b, for respectively receiving the sealing ports 12a, 12b, 14a, 14b. The seal base 26 can also have an insufflation port cut-out or opening 80e formed therethrough for seating the insufflation port 28. A person skilled in the art will appreciate that there can be any number of port openings formed in the seal base 26 that can be arranged in any way in the base 26. As shown in the illustrated embodiment, the port openings 80a, 80b, 80c, 80d, and hence also the sealing ports 12a, 12b, 14a, 14b, can be radially arranged around a central axis or center-point 94 of the seal base 26 with the fixed sealing ports 12a, 12b and the movable sealing ports 14a, 14b alternating around the base center-point 94.

The port openings 80a, 80b, 80c, 80d can also have any combination of sizes and shapes. As shown, the port openings 80a, 80b, 80c, 80d can each have a shape corresponding to a shape of the sealing port 12a, 12b, 14a, 14b, 28 seated therein, which in this illustrated embodiment is substantially circular for each of the openings 80a, 80b, 80c, 80d. The first port opening 80a for seating the first fixed sealing port 12a can have a first diameter D1 that is larger than a second diameter D2 of the second port opening 80b for seating the second fixed sealing port 12b, and the third and fourth port openings 80c, 80d for respectively seating the movable sealing ports 14a, 14b can each have a third diameter D3 that is larger than both the first and second diameters D1, D2. The insufflation port opening 80e can have any diameter D4. The third diameter D3 of the third and fourth port openings 80c, 80d can define a diameter of an orbital path of first and second movable sealing elements, as discussed further below. For non-limiting example, the base 26 can have a diameter D5 of about 60 mm, the first diameter D1 can be about 15 mm, the second diameter D2 can be about 9 mm, the third diameter D3 can be about 25 mm, and the insufflation diameter D4 can be about 2 mm.

In some embodiments, the proximal base surface of the seal base can be substantially flat with port openings being formed in a same plane with each other, either co-planar parallel to the proximal base surface or recessed in the seal base. In other embodiments, such as the one illustrated in FIGS. 1-6, the proximal base surface 78 can be non-planar with at least one recessed portion extending in a plane distally displaced from and parallel to a plane of the proximal base surface 78 and/or at least one raised portion proximally displaced from and parallel to a plane of the proximal base surface 78. The base 26 can also have port openings formed in the plane of the proximal base surface 78, such as the third and fourth port openings 80c, 80d seating the third and fourth movable sealing ports 14a, 14b. The seal base's one or more recessed portions and one or more raised portions can help compensate for sealing elements of different lengths to help prevent distal seal element openings of each of the sealing elements from contacting an interior of the retractor 18, as discussed below, at least when the surgical access device 10 is in a default position, e.g., as illustrated in FIGS. 1-4, where the device 10 is not positioned in tissue and has no surgical instruments inserted therethrough.

In this illustrated embodiment, the seal base 26 has one raised or proximally extending housing 96 in which the first port opening 80a is formed. The raised housing 96 can have any height, same or different from any other raised housings, configured to help provide clearance room for the first fixed sealing element 20 seated in the first port opening 80a positioned above the proximal base surface 78 to help prevent the first fixed sealing element from contacting the retractor 18, as discussed below, at least when the surgical access device 10 is in the default position. The raised housing 96 can be rigid, as shown, or it can be flexible to allow the raised housing 96 to move vertically, laterally, and angularly relative to the seal base 26.

The illustrated seal base 26 also has one recessed portion 98 in which the second port opening 80b is formed. The recessed portion 98 can be recessed any depth below the proximal base surface 78, and it can be configured to allow a relatively small sealing element to extend through the base 26 and have its distal end substantially co-planar with distal ends of any other sealing elements extending through the base 26. As illustrated in this embodiment, the recessed portion 98 of the base 26 can be in communication with the cut-out portion 82a formed in the circumferential wall 82 of the proximal base portion 26a, which can allow greater flexibility in angular insertion of a surgical instrument through the second port opening 80b within the recessed portion 98. A circumferential wall 102 of the housing 16 can include one or more cut-out portions (not shown) configured to correspond in radial location to the one or more cut-out portions 82a formed in the base 26 when the housing 16 and the base 26 are attached to the retractor 18 to further ease insertion of surgical instruments through the base 26.

The sealing ports 12a, 12b, 14a, 14b can be attached or mated to the seal base 26 using any attachment or mating mechanism known in the art, but in the illustrated embodiment the fixed sealing ports 12a, 12b each mate with the seal base 26 using engaging pins and holes, while the movable sealing ports 14a, 14b each mate with the seal base 26 through an interference fit between the proximal and distal base portions 26a, 26b. In general, the first and second fixed sealing ports 12a, 12b and the first and second movable sealing ports 14a, 14b can each include a port housing, which can be seated directly or indirectly in one of the port openings 80a, 80b, 80c, 80d in the seal base 26, and a sealing element, which can be positioned within an associated port housing. A sealing element can include at least one instrument seal and/or at least one channel seal, and can generally be configured to contact an instrument inserted through the sealing element's associated sealing port.

As shown in FIGS. 6 and 8-10 and discussed further below, the first fixed sealing port 12a can include a first port housing, which can be seated within the first port opening 80a in the seal base 26, and a first sealing element, which can be positioned within the first port housing. The first port housing can include a crown 112, a gasket ring 114, and a retainer ring 116. The first sealing element can include a first distal seal 20 and a proximal seal including a multi-layer conical seal 104 positioned proximal to the first distal seal 20 and a multi-layer protective member 108 disposed on a proximal surface of the conical seal 104. The second fixed sealing port 12b can include a second port housing, which can be seated within the second port opening 80b in the seal base 26, and a second sealing element, which can be positioned within the second port housing. The second port housing can include a press cap 126. The second sealing element can include a second distal seal 22, and a proximal seal including a lip seal 132 positioned on a proximal end of the distal seal 22 and a multi-layer protective member 124 positioned proximal to the lip seal 132. The first and second movable sealing ports 14a, 14b can respectively include first and second supports or movable port housings, which can be respectively seated in the third and fourth port openings 80c, 80d in the seal base 26, and first and second movable sealing elements, which can be respectively positioned within their respective movable port housings. The first and second supports or movable port housings can each include a proximal cap, a seal retainer, an eccentric seal, and an eccentric base. The first and second movable sealing elements can each include a distal seal, a lip seal positioned on a proximal end of the distal seal, and a multi-layer protective member positioned proximal to the lip seal.

The various port housings and sealing elements of the fixed and movable sealing ports 12a, 12b, 14a, 14b can have a variety of sizes, shapes, and configurations. A person skilled in the art will appreciate that while channel or zero-closure seals in the form of duckbill seals are shown for each of the distal seals 20, 22, 24a, 24b, any seal, e.g., duckbill seals, cone seals, flapper valves, gel seals, diaphragm seals, lip seals, iris seals, non-linear sealing elements such sealing elements with an S-shaped opening, etc., same or different from any other of the other distal seals 20, 22, 24a, 24b can be used and can be aligned in any way relative to the base 26. Generally, a zero-closure seal can be configured to form a seal in a working channel when no instrument is disposed therethrough to thus prevent the leakage of insufflation gases delivered through the surgical access device to the body cavity. A duckbill seal can generally have opposed flaps that extend at an angle toward one another in a distal direction and that come together at a distal end to form a seal face. The opposed flaps can be movable relative to one another to allow the seal face to move between a closed position, in which no instrument is disposed therethrough and the seal face seals the working channel of the surgical access device, and an open position in which an instrument is disposed therethrough. A duckbill seal can include various other features, as described in more detail in U.S. application Ser. No. 11/771,263, entitled "Duckbill Seal with Fluid Drainage Feature," filed on Jun. 29, 2007, which is hereby incorporated by reference in its entirety. In addition, the seal face of the duckbill seal can be in any nonlinear shape or configuration known in the art, for example in an S-shaped configuration, as described in more detail in U.S. Pat. No. 5,330,437, entitled "Self Sealing Flexible Elastomeric Valve and Trocar Assembly for Incorporating Same," filed Nov. 12, 1993, which is hereby incorporated by reference in its entirety.

As mentioned above and as illustrated in FIG. 8, the first fixed sealing port 12a can include the first port housing and the first sealing element. The multi-layer conical seal 104 of the first sealing element can include a series of overlapping seal segments 106 that are assembled in a woven arrangement to provide a complete seal body. The seal segments 106 can be stacked on top of one another or woven together in an overlapping fashion to form the multi-layer seal 104 having a central opening (not shown) therein. The seal segments 106 can be made from any number of materials known to those skilled in the art, but in an exemplary embodiment the seal segments 106 are formed from an elastomeric material. The multi-layer protective member 108 can similarly be formed from a series of overlapping segments 110 that are disposed proximal to the overlapping seal segments 106 and that are configured as anti-eversion elements to protect the seal segments 106 from damage caused by surgical instruments passed through the opening in the multi-layer seal 104. The protective member 108 can also be formed from various materials, but in certain exemplary embodiments the protective member 108 is formed from a molded thermoplastic polyurethane elastomer, such as Pellethane™.

Figure 8:
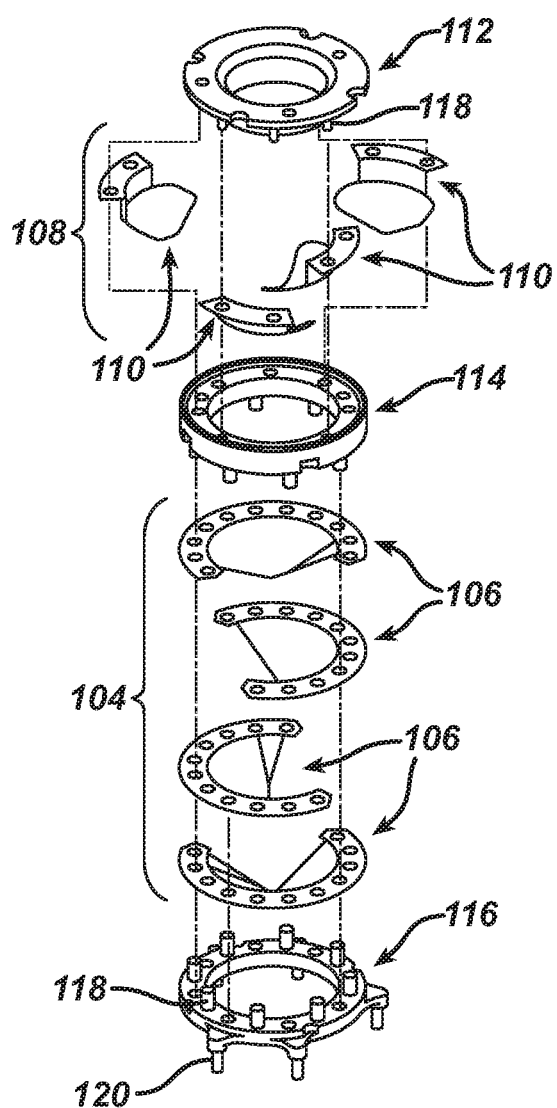
FIG. 8 is a partial, exploded view of a fixed sealing port of the device of FIG. 1.

The segments 106, 110 that form the multi-layer seal 104 and the protective member 108 can be held together using various techniques known in the art. As shown in FIG. 8, the segments 106, 110 can be held together by a plurality of ring members that mate to engage the segments 106, 110 therebetween. In particular, the protective member 108 can be engaged between the crown 112 and the gasket ring 114, and the seal 104 can be engaged between the gasket ring 114 and the retainer ring 116. Pins 118 can be used to mate the ring members 112, 114, 116 and to extend through and engage the segments 106, 110 of the seal 104 and the protective member 108. In some embodiments, an o-ring (not shown) can be positioned between the retainer ring 116 and the seal base 26 to ensure an air and liquid tight seal between the same.

When fully assembled, the first port housing can be disposed at various locations within the surgical access device 10, e.g., in the first port opening 80a formed in the base 26. As shown in FIGS. 6 and 8, the first port housing can include one or more distally extending seating pins, e.g., five pins 120 distally extending from the retainer ring 116, that are configured to be received in one or more corresponding slots formed in the base 26, e.g., five slots 122 formed in the distal base portion 26b, to properly position the first fixed sealing port 12a relative to the base 26. As mentioned above, the first fixed sealing port 12a can also include the first distal seal 20, which can have a proximal flange that is captured between the retainer ring 116 and the distal seal base portion 26b to secure the first distal seal 20 therebetween. In use, a surgical instrument can be passed through a center opening of the protective member 108 and the multi-layer seal 104, and the seal segments 106, 110 can engage and form a seal around an outer surface of the instrument to thereby prevent the passage of fluids and gas through the seal. When no instrument is disposed therethrough, the center opening will generally not form a seal in the working channel, however other configurations in which a seal is formed when no instrument is disposed therethrough are also conceivable. Exemplary instrument seal configurations are described in more detail in U.S. Patent Publication No. 2004/0230161 entitled "Trocar Seal Assembly," filed on Mar. 31, 2004, and U.S. patent application Ser. No. 10/687,502 entitled "Conical Trocar Seal," filed on Oct. 15, 2003, which are hereby incorporated by reference in their entireties. The instrument can be further inserted through the sealing element, e.g., through the first distal seal 20. When no instrument is disposed therethrough, the first distal seal 20 can be configured to form a seal in the working channel, however other configurations in which a seal is not formed without an instrument is disposed therethrough are also conceivable.

Figure 9:
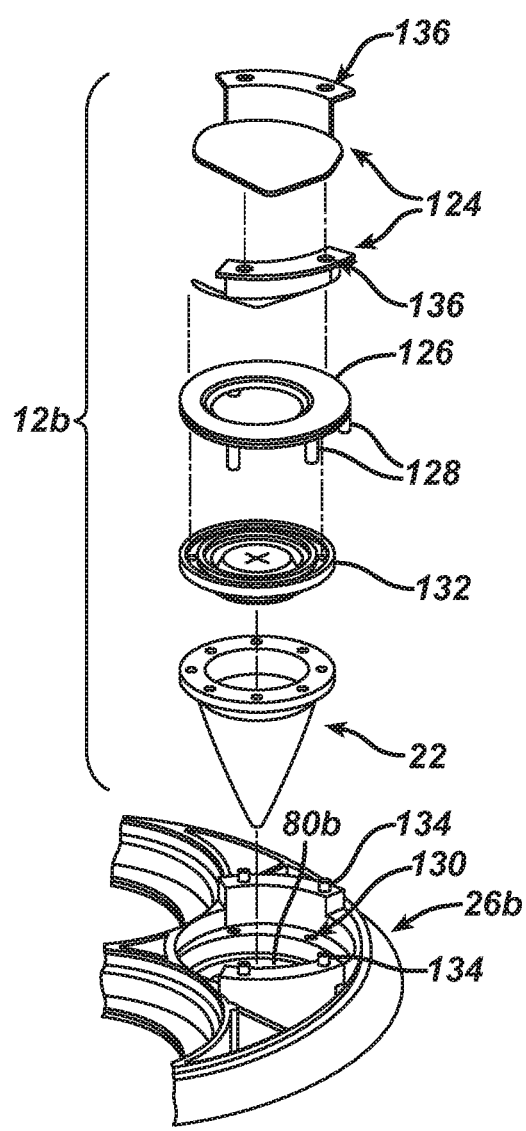
FIG. 9 is an exploded view of another fixed sealing port of the device of FIG. 1 and a partial perspective view of the seal base in which the fixed sealing port can be disposed.

The second fixed sealing port 12b can generally be configured and used as an instrument seal similar to the first fixed sealing port 12a. In this illustrated embodiment, as shown in FIG. 9, the second fixed sealing port 12b can include the second port housing configured to mate with the base 26 and can include the second sealing element configured to be disposed between the second port housing and the base 26. The second fixed sealing port 12b can generally have the multi-layer protective member 124 disposed on a proximal surface of the press cap 126. The press cap 126 can be configured to mate with the seal base 26 using a mating mechanism, e.g., pins 128 distally extending from the press cap 126 configured to engage corresponding holes 130 formed in the seal base 26. The second distal seal 22 with the lip seal 132 disposed on a proximal surface thereof can be secured between the press cap 126 and the seal base 26. The multi-layer protective member 124 can also mate to the seal base 26 to help fixedly secure the second fixed sealing port 12b within the second port opening 80b formed in the base 26 by using an attachment mechanism such as pins 134 proximally extending from the seal base 26 that are configured to engage corresponding holes 136 formed in the multi-layer protective member 124.

Figure 10:
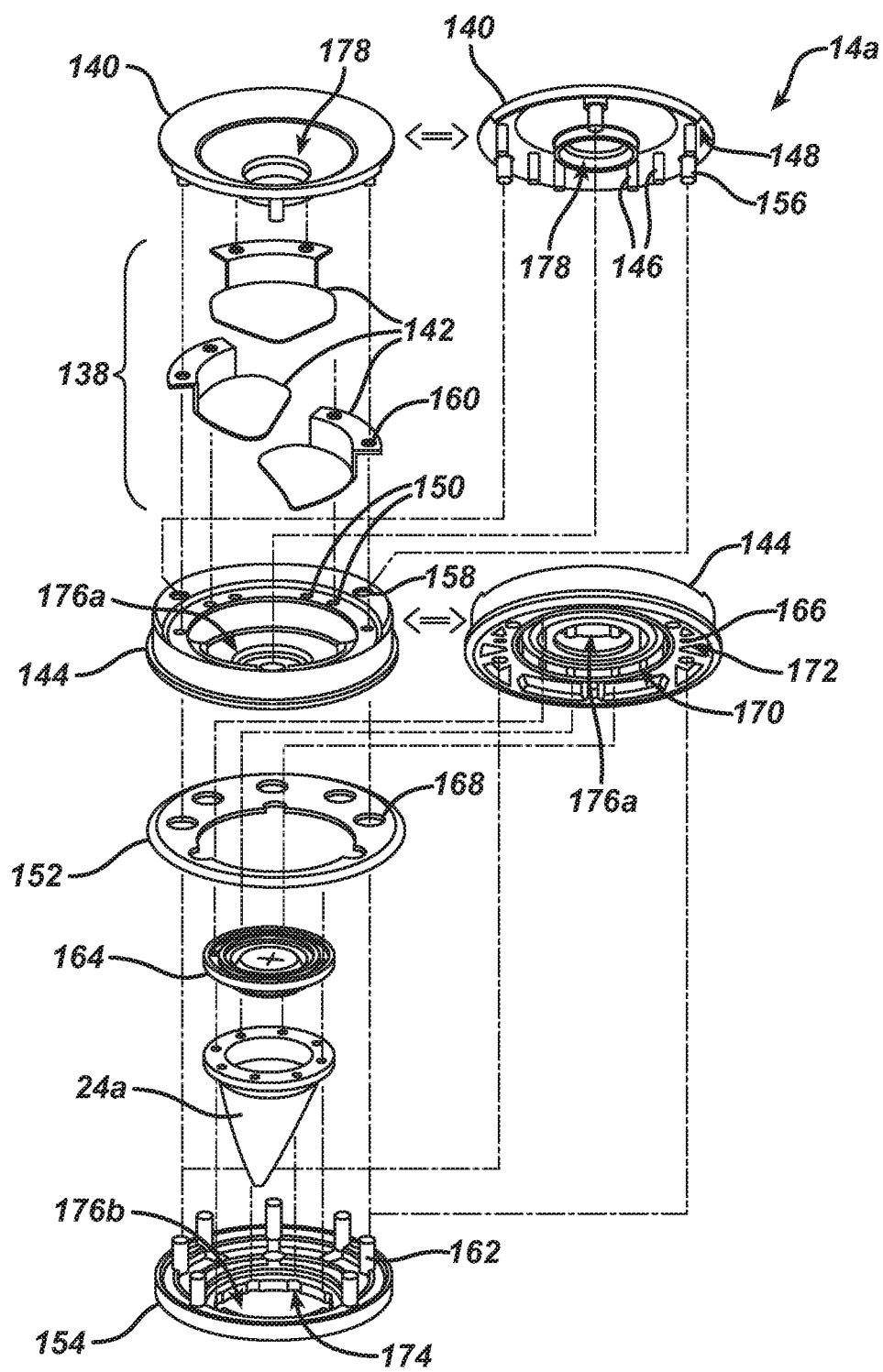
FIG. 10 is an exploded view of a movable sealing port of the device of FIG. 1.

The first movable sealing port 14a can generally be configured and used as an instrument seal similar to the first and second fixed sealing ports 12a, 12b. However, in contrast to the fixed sealing ports 12a, 12b, the first movable sealing port 14a can be configured to be movably rather than fixedly attached to the seal base 26. The first movable sealing port 14a can include the first movable port housing having a circular shape with the first movable sealing element disposed therein. As illustrated in FIG. 10, the third sealing port 14a can generally have a multi-layer protective member 138 positioned between a proximal cap 140 and a seal retainer 144. The multi-layer protective member 138 can be formed from a series of overlapping segments 142 that are configured as anti-eversion elements to protect the seal segments 142 from damage caused by surgical instruments passed through the first movable sealing port 14a. The proximal cap 140 and the seal retainer 144 can be configured to mate together with the protective member 138 positioned therebetween using a mating mechanism such as one or more cap retaining pins 156 distally extending from a distal surface 148 of the proximal cap 140 that are configured to engage one or more corresponding cap retaining pin openings 158 formed in the seal retainer 144. One or more leaf pins 146 distally extending from the distal surface 148 of the proximal cap 140 can be configured to pass through leaf segment openings 160 formed in the seal segments 142 and to engage one or more corresponding leaf pin openings 150 formed in the seal retainer 144 to retain the protective member 138 in a fixed position relative to the proximal cap 140 and the seal retainer 144.

Figure 2:
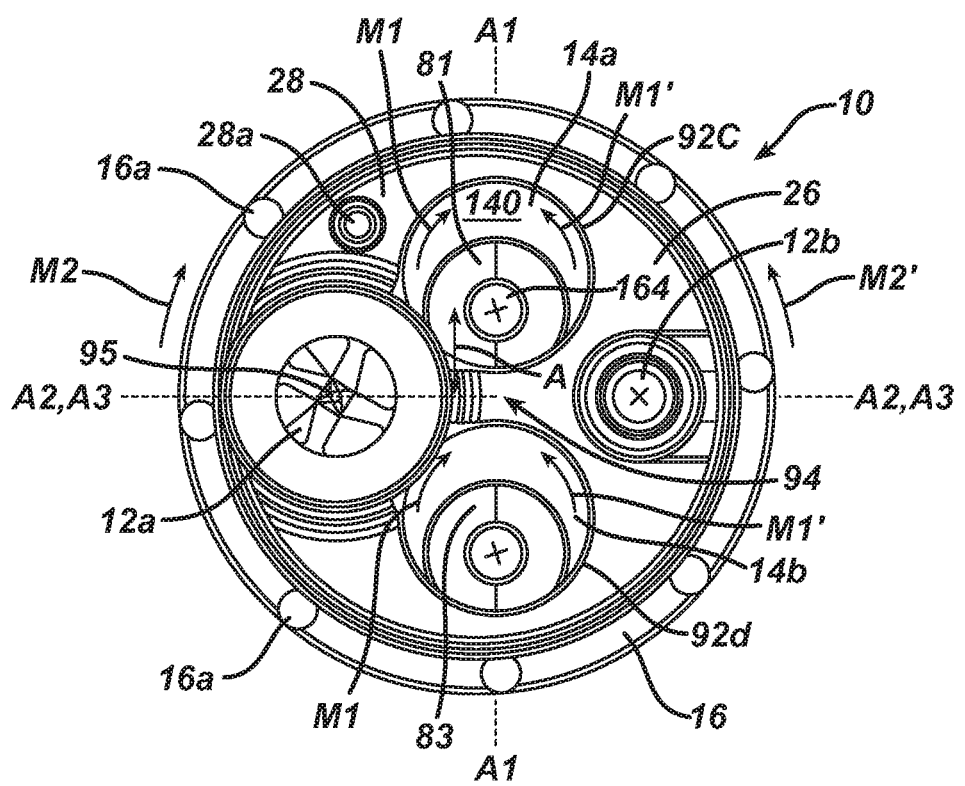
FIG. 2 is a top view of the device of FIG. 1.

A proximal movable port assembly including the protective member 138, the proximal cap 140, and the seal retainer 144 can be configured to mate with a distal movable port assembly including an eccentric ring 152 and an eccentric base 154, with the first movable distal seal 24a positioned between the seal retainer 144 and the eccentric base 154. The first movable distal seal 24a having a lip seal 164 positioned on a proximal end thereof can be disposed between opposed seal element openings 176a, 176b respectively formed in the seal retainer 144 and the eccentric base 154. The first movable distal seal 24a and the lip seal 164 coupled to the proximal end thereof, as well as the multi-layer protective member 138, can thereby be eccentric relative to the first movable port housing. The seal element openings 176a, 176b can be in communication with a seal opening 178 formed in the proximal cap 140 to allow a surgical instrument to be inserted through the seal opening 178 in the proximal cap 140 and into the first movable distal seal 24a. The seal element openings 176a, 176b and the seal opening 178 can define a central axis that is offset from a central axis or center-point 81 of the first movable port housing, which corresponds to a central axis or center-point 81 of the third port opening 80c in which the first movable port housing is seated, as illustrated in FIGS. 2, 6, and 10. One or more seal pins 162 proximally extending from a proximal surface of the eccentric base 154 can be configured to be positioned radially around the sealing element including a lip seal 164 positioned on a proximal end thereof, to pass through one or more seal pin openings 168 formed in the eccentric ring 152, and to engage one or more corresponding seal pin openings 170 formed in a distal surface 172 of the seal retainer 144. An alignment mechanism can be configured to properly align the seal retainer 144 and the eccentric base 154 relative to one another, e.g., one or more locating pins 166 distally extending from the distal surface 172 of the seal retainer that are configured to engage one or more corresponding locating pin channels 174 formed in the eccentric base 154.

The second movable sealing port 14b in the illustrated embodiment can be configured and used similar to the first movable sealing port 14a, although a person skilled in the art will appreciate that the first and second movable sealing ports 14a, 14b can be configured different from one another.

Figure 3:
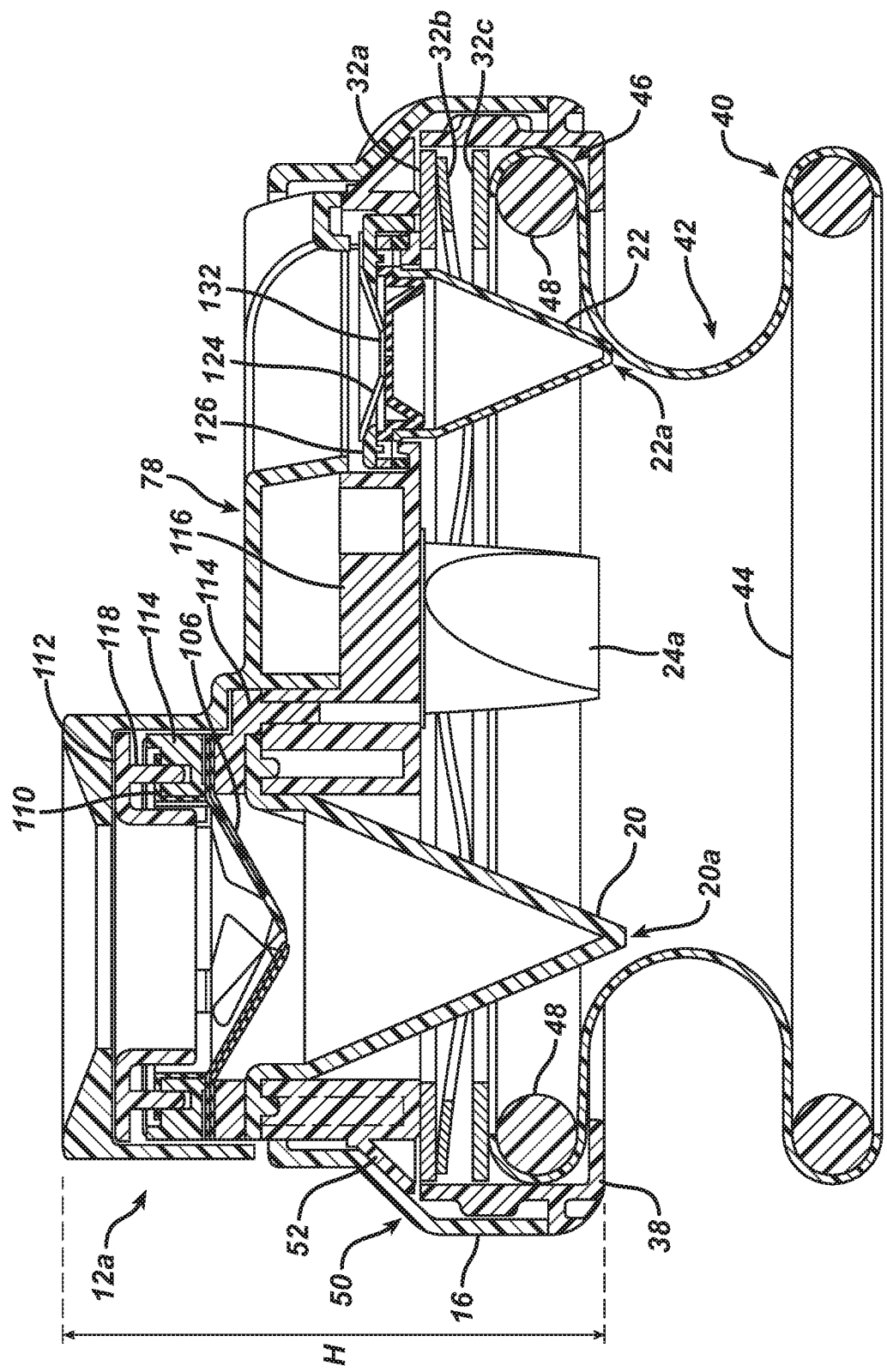
FIG. 3 is a cross-sectional view of the device of FIG. 1.
Figure 4:
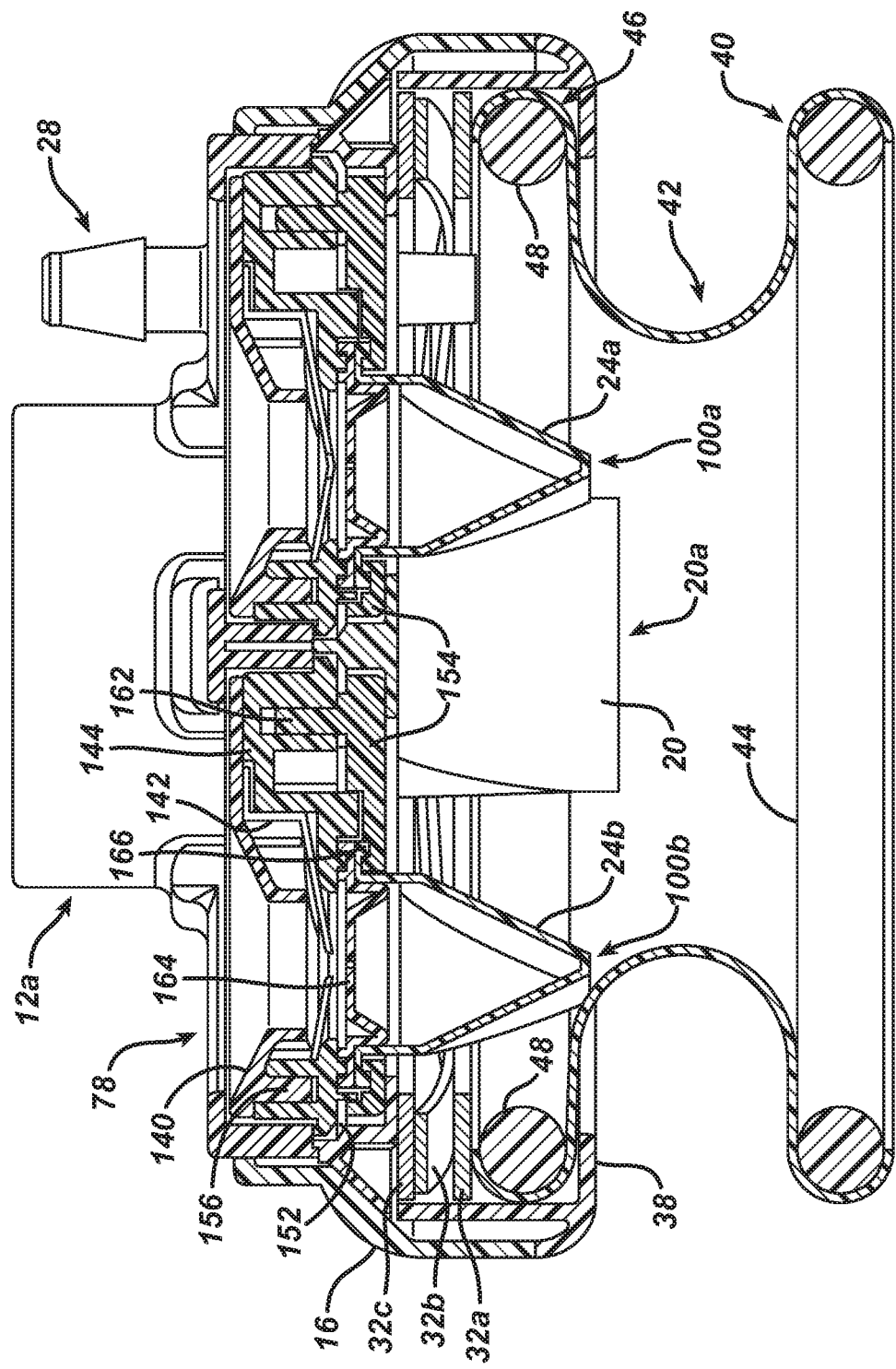
FIG. 4 is another cross-sectional view of the device of FIG. 1.

As shown in FIG. 3, the seal base 26 and the housing 16 can have a height H that is less than a longitudinal length of the device's sealing elements. In such a configuration, one or more of at least the fixed sealing elements can be oriented to minimize contact with the retractor 18. For non-limiting example, each of the fixed distal seals 20, 22 can be aligned with their respective distal sealing element openings 20a, 22a tangential to a nearest portion of a circumference of the housing 16 and the retractor 18 extending from the housing 16 as shown in FIGS. 3 and 4. In other words, the distal sealing element openings 20a, 22a can extend in a direction that is substantially parallel to a closest portion of a circumference of the housing 16, and not transverse to the housing 16. Such an alignment can help prevent the distal sealing element openings 20a, 22a from being pushed open by an inner wall of the retractor's inner elongate portion 42 when the seal base 26 is moved relative to the retractor 18. In some embodiments, the seal base 26 and/or the housing 16 can have a height H to accommodate a full length of the sealing elements to prevent the sealing elements from coming into contact with the interior of the retractor 18.

As mentioned above, the first and second fixed sealing ports 12a, 12b, including their respective port housings and respective sealing elements, can be configured to be in a fixed position relative to the base 26 and to rotate with the base 26 relative to the housing 16 and the retractor 18. On the other hand, the first and second movable sealing ports 14a, 14b, including their respective port housings and respective movable sealing elements, can be movable within their respective port openings 80c, 80d relative to the base 26 and hence also relative to the fixed sealing ports 12a, 12b. The first and second movable sealing ports 14a, 14b can also be configured to be movable independent of one another and when individually moved can cause rotational movement of the base 26, and/or cause rotational and/or lateral movement of the other one of the movable sealing ports 14a, 14b when a surgical instrument is inserted through the other one of the movable sealing ports 14a, 14b and is held in a substantially fixed position therein.

The first movable sealing port 14a including the first movable port housing and the first movable sealing element can be configured to be rotatably movable relative to the base 26, the housing 16, and the retractor 18 by rotating within the third opening 80c in a first direction M1, e.g., clockwise, and/or in a second, opposite direction M1', e.g., counterclockwise. Being mated to the seal base 26, the first movable port housing can also be configured to be rotatable around the center-point 94 of the base 26 in a first direction M2, e.g., clockwise, and/or in a second, opposite direction M2', e.g., counterclockwise. In this way, the first movable sealing port 14a can be configured to have dual rotational motion by being separately or concurrently rotatable around the third port opening's center-point 81 and around the base's center-point 94. The first movable sealing port 14a can thus be configured to independently rotate around the port opening center-points 81 in the first and/or second directions M1, M1', to independently rotate around the base center-point 94 in the first and/or second directions M2, M2', and to simultaneously rotate with the base 26 and within third port opening 80c, thereby helping to provide for optimal positioning of a surgical instrument inserted through the first movable sealing port 14a. In the illustrated embodiment, the first movable port housing can rotate 360° in each of the first and second directions M1, M1', and the base 26 can rotate 360° in each of the first and second directions M2, M2'. Although, a person skilled in the art will appreciate that the first movable port housing can be configured to rotate any number of degrees in either of the directions M1, M1' and that the base 26 can be configured to rotate any number of degrees in either of the directions M2, M2'.

Because the first movable port housing can be held by interference fit within the base 26, the first movable port housing can be configured to be rotatably movable relative to the base 26, the housing 16, and the retractor 18, e.g., around the center-point 81 of the third port opening 80c and the first movable port housing, but not be laterally movable or orbital relative to the base 26, the housing 16, or the retractor 18. However, the first movable sealing element of the first movable sealing port 14a can be configured to be both rotationally movable and laterally movable relative to the base 26, the housing 16, and the retractor 18. In other words, the first movable sealing element can be configured to rotate within the third port opening 80c as the first movable port housing rotates and thereby laterally move or orbit in a plane parallel to a plane of the base's proximal surface 78. As mentioned above, the first movable sealing port 14a can be configured to not be substantially vertically movable, e.g., distally or proximally movable, within the third port opening 80c, but as will be appreciated by a person skilled in the art, the spring assembly 32, discussed further below, can allow a small amount of vertical movement of the first movable sealing port 14a.

The first movable sealing element can be configured to be laterally movable in a predetermined orbital path defined by the third port opening 80c in which the first movable sealing port 14a is disposed. The predetermined orbital path of the first movable sealing element can have any shape and size, but as shown in this embodiment in FIGS. 2, 6, 7A, and 7B, the predetermined orbital path can generally be defined by a perimeter 92c of the third port opening 80c formed in the base 26, e.g., defined by a circle having the third diameter D3. Because the first movable sealing element is eccentric with the first movable port housing, i.e., is positioned off center in the first movable port housing, the predetermined orbital path can be defined by the third port opening 80c in the base 26 but it can be smaller than the third diameter D3 of the third port opening 80c, e.g., have an orbital path diameter of about 18 mm versus the third diameter D3 of about 25 mm.

The second movable sealing port 14b can be movable similar to the first movable sealing port 14a. Generally, the second movable port housing of the second movable sealing port 14b can be configured to rotate relative to the base 26, the housing 16, and the retractor 18 with the second movable sealing element of the second movable sealing port 14b also being configured to laterally move or orbit in a predetermined orbital path defined by a perimeter 92d of the fourth port opening 80d.

As mentioned above, the device 10 can be configured such that movement of the base 26 relative to the housing 16 and the retractor 18 and movement of either of the first and second movable sealing ports 14a, 14b, and hence also lateral movement of the respective first and second movable sealing elements, relative to the base 26, the housing 16, and/or the retractor 18 can cause movement of at least one other of the base 26 and the first and second movable sealing ports 14a, 14b relative to at least the retractor 18. Such responsive movement of at least one of the base 26, the first movable sealing port 14a, and the second movable sealing port 14b can allow for surgical instruments inserted through the device 10 into a body cavity to dynamically adjust their positions, thereby helping to reduce the "chopstick effect" of interference between the instruments in the body cavity and to maximize an amount of working space available to each of the instruments.

Although the base 26 can be configured to be movable relative to the housing 16 and the retractor 18 with or without any instruments inserted through any of the ports 12a, 12b, 14a, 14b, e.g., by being manually rotated by hand, the base 26 can also be configured to move relative to the housing 16 and the retractor 18 in response to motion of at least one instrument inserted through one of the ports 12a, 12b, 14a, 14b.

Figure 11:
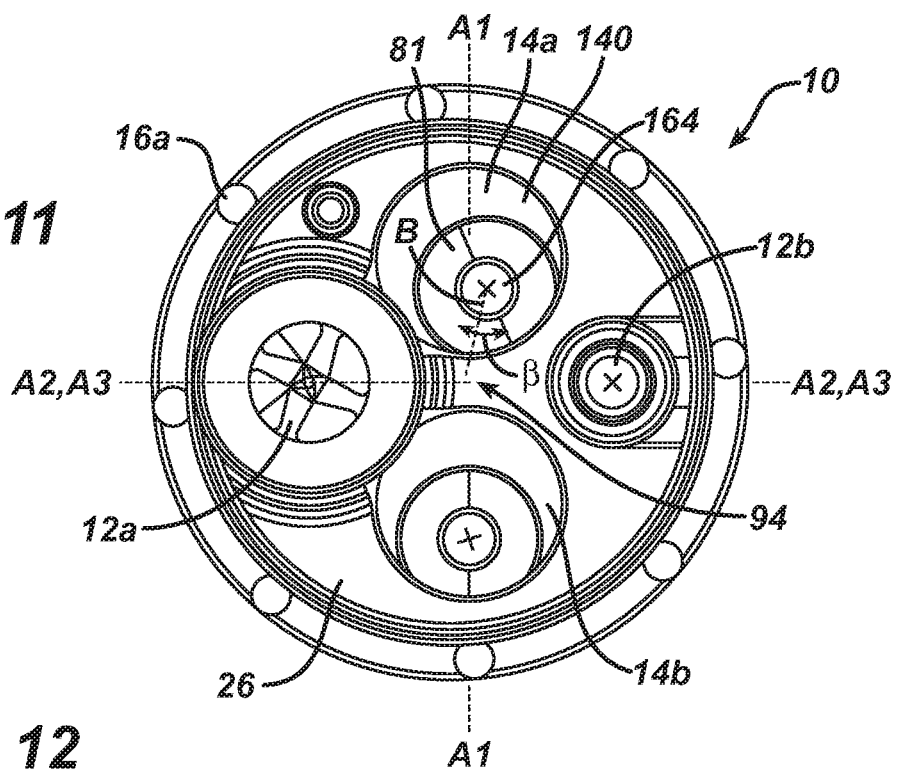
FIG. 11 is a top view of the device of FIG. 1 with one of the movable sealing ports rotated relative to the seal base, a housing, and a retractor of the device.

As shown in one embodiment of surgical access device movement in FIGS. 2 and 11, the first movable sealing port 14a can be configured to rotate in the second direction M1' relative to the base 26, the housing 16, and the retractor 18 (not visible in FIGS. 2 and 11) from a first position shown in FIG. 2 to a second position shown in FIG. 11. During such rotation, the first movable port housing including the proximal cap 140 moves in the second direction M1' around the center-point 81 of the first movable port housing by rotating within the third port opening 92c. The first movable sealing element can also rotationally move in the second opposite direction M1', with the first movable sealing element also laterally moving or orbiting an angle β around its orbital path from a first position (FIG. 2) to a second, different position (FIG. 11). With such lateral or orbital movement, the first movable sealing element can move from the first position that is a first distance A from the base center-point 94 to the second position that is a second, different distance B from the base center-point 94. The second distance B is greater than the first distance A in this illustrated embodiment, but the first movable sealing element can laterally move such that the second distance B is less than the first distance A or such that the first and second distances A, B are equal.

The second movable sealing port 14b can be configured to rotationally and laterally move similar to the first movable sealing port 14a. In response to movement of the first movable sealing port 14a, the second movable sealing port 14b and/or the base 26 can be configured to rotationally move relative to the housing 16 and the retractor 18, and/or the other movable sealing port 14b with a surgical instrument is inserted therethrough and held in a fixed position therein can be configured to laterally move relative to the base 26. In this illustrated embodiment, the base 26 and the second movable sealing port 14b are in substantially the same position relative to the retractor 18 and the second movable sealing port 14b is in the same position relative to the base 26 when the first movable sealing port 14a is in both the first and second positions, shown in FIGS. 2 and 11 respectively. The base 26 and the second movable sealing port 14b can remain in substantially the same position when the first movable sealing port 14a moves from the first position to the second position for a variety of reasons, such as instruments inserted through other ports in the base 26 already being optimally positioned or the first movable sealing port 14a not rotating at a large enough angle β to cause movement of either the base 26 or the second movable sealing port 14b.

Figure 12:
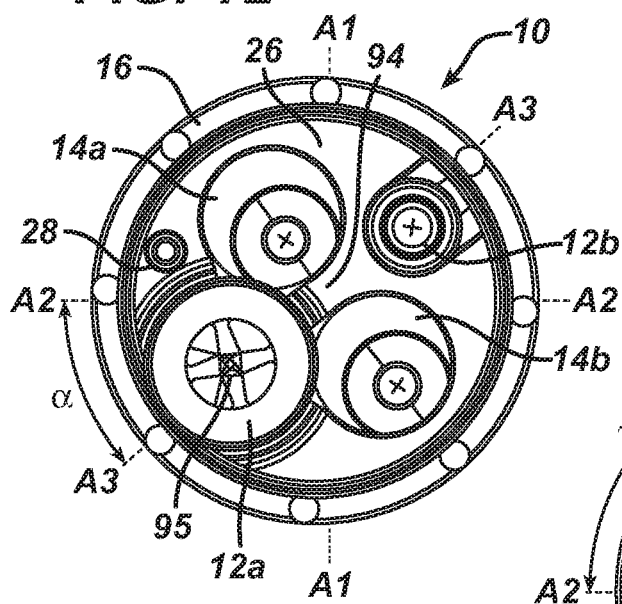
FIG. 12 is a top view of the device of FIG. 1 with the seal base rotated relative to the housing and the retractor, and one of the movable sealing ports rotated relative to the seal base, the housing, and the retractor.

As shown in another embodiment of surgical access device movement in FIGS. 2 and 12, the base 26 can be configured to rotate relative to the retractor 18 (not visible in FIGS. 2 and 12) in the second direction M2' around the center-point 94 of the base 26 from a first position (FIG. 2) to a second position (FIG. 12). Perpendicular first and second horizontal axes A1, A2 that intersect at the center-point 94 of the base 26, help indicate the rotational movement of the base 26 relative to the retractor 18. A horizontal axis A3 of the base 26 passing through the center-point 94 of the base 26 and a center-point 95 of the first fixed sealing port 12a can be aligned with the second perpendicular horizontal axis A2 when the base 26 is in the first position shown in FIG. 2 and can move an angle α from the second horizontal axis A2 when the base 26 has been moved to the second position shown in FIG. 12. Movement of base 26 relative to retractor 18 can, as shown, also move any or all of the device's ports 12a, 12b, 14a, 14b, 28 relative to the retractor 18. While the movable sealing ports 14a, 14b can be configured to move relative to the base 26 in response to movement of the base 26, e.g., rotational movement of the movable port housings, in this illustrated embodiment, the movable sealing elements can be configured to stay in a substantially fixed position in response to movement of the base 26, such as shown here with the movable sealing ports 14a, 14b being in substantially the same position relative to the base 26 with the base 26 in both the first and second positions of FIGS. 2 and 12. When a surgical instrument (not shown in FIGS. 2 and 12) is inserted through a movable sealing element and held in a substantially fixed position therein when the base 26 rotates, the movable port housing associated with that movable sealing element can rotate relative to the base 26 while the movable sealing element can stay in substantially the same position, thereby allowing the instrument inserted therethrough to remain in substantially the same position. The movable sealing elements can remain in substantially the same position relative to the base 26 for other reasons when the base 26 rotates, such the base 26 not rotating at a large enough angle α to cause rotational motion of either of the movable sealing ports 14a, 14b.

Figure 13:
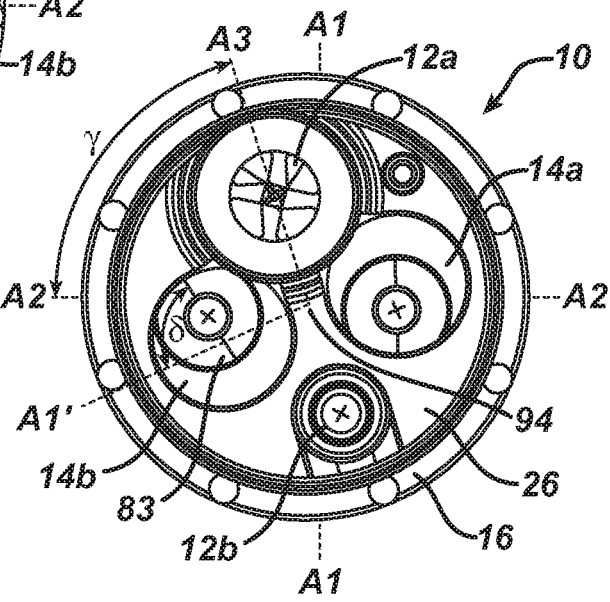
FIG. 13 is a top view of the device of FIG. 1 with the seal base rotated relative to the housing and the retractor, and each of the movable sealing ports rotated relative to the seal base, the housing, the retractor, and each other.

In another embodiment of surgical access device movement illustrated in FIGS. 2 and 13, the second movable sealing port 14b can be configured to rotate relative to the base 26, the housing 16, and the retractor 18 (not visible in FIGS. 2 and 13) at an angle δ in the first direction M1 from a first position (FIG. 2) to a second position (FIG. 13). The angle δ is defined by the position of the second movable sealing port 14b relative to the former position of the first horizontal axis A1, labeled A1' in FIG. 13, passing through a center axis or center-point 83 of the second movable sealing port 14b. As discussed above, the second movable sealing element of the second movable sealing port 14b can laterally move and rotationally move in the first direction M1. In this illustrated embodiment, the base 26 and the first movable sealing port 14a both move in response to movement of the second movable sealing port 14b. The base 26 moves relative to the housing 16 and the retractor 18 in response to movement of the second movable sealing port 14b by rotating an angle γ in the first direction M2. The first directions M1, M2 of the second movable sealing port 14b and the base 26, respectively, can correspond, e.g., can both be clockwise, because lateral motion of the second movable sealing element of the second movable sealing port 14b in the first direction M1 can assert a similarly directed force against the base 26 and cause the base 26 to move in the first direction M2. Similarly, the first movable sealing port 14a moves relative to the base 26, the housing 16, and the retractor 18 in response to movement of the second movable sealing port 14b by rotating in the first direction M1. The first movable sealing port 14a can be configured to dynamically move by the angle δ that the second movable sealing port 14b moved or dynamically move by another, different angle.

In use, one or more surgical instruments can be inserted into a body cavity through the surgical access device 10, which can help optimally position the surgical instruments relative to the body cavity through movement of the base 26 and/or movement of one or both of the movable sealing ports 14a, 14b. The device 10 can be positioned within tissue to provide access to a body cavity underlying the tissue in a variety of ways. In one embodiment, the device 10 can be positioned in tissue fully assembled in the default state shown in FIG. 1. In another embodiment, the device 10 can be positioned partially assembled in tissue and be fully assembled with a portion of the device 10 positioned in the tissue.

Figure 18:
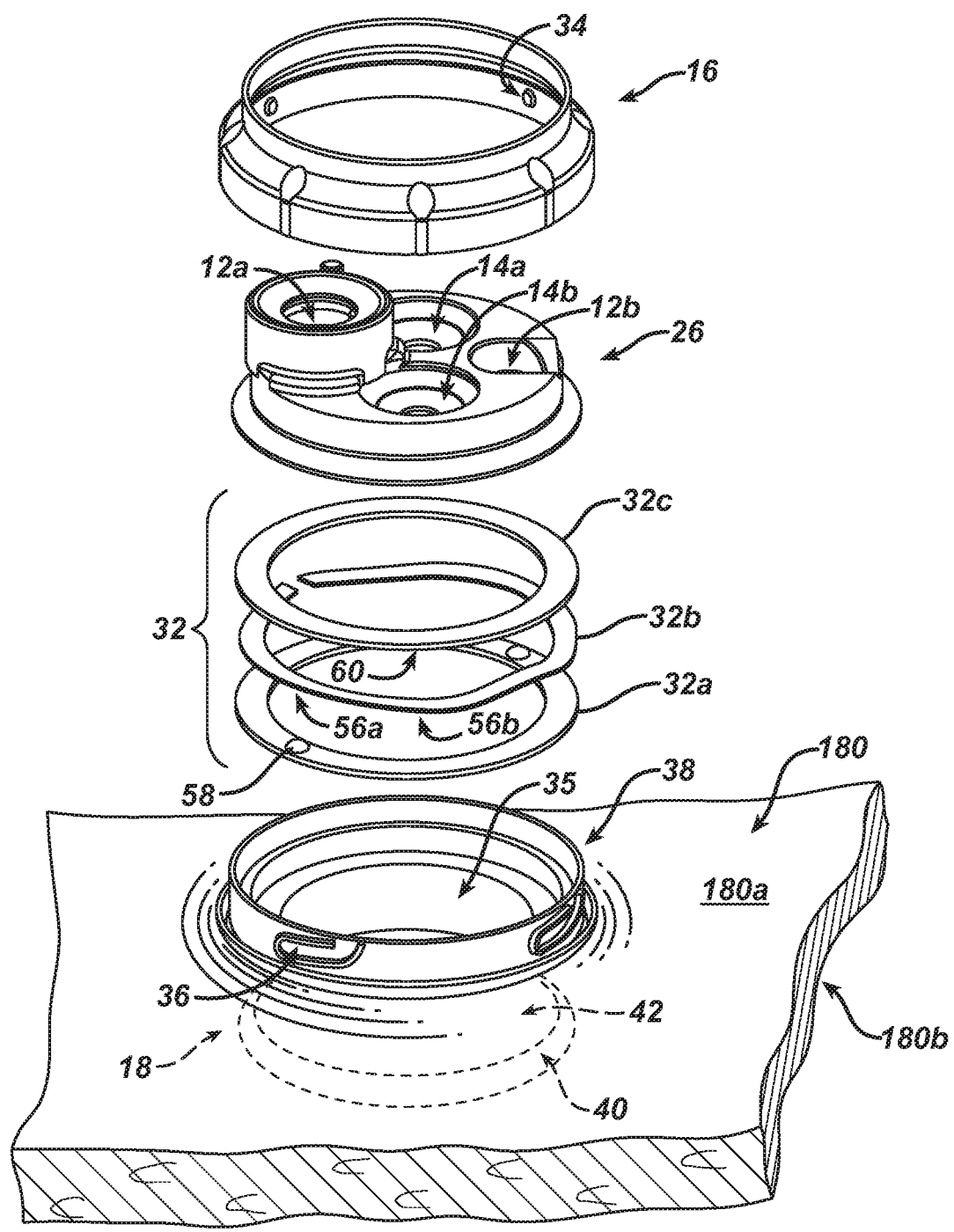
FIG. 18 is a partial cross-sectional, perspective, exploded view of the device of FIG. 1 with the retractor positioned in tissue.
Figure 19:
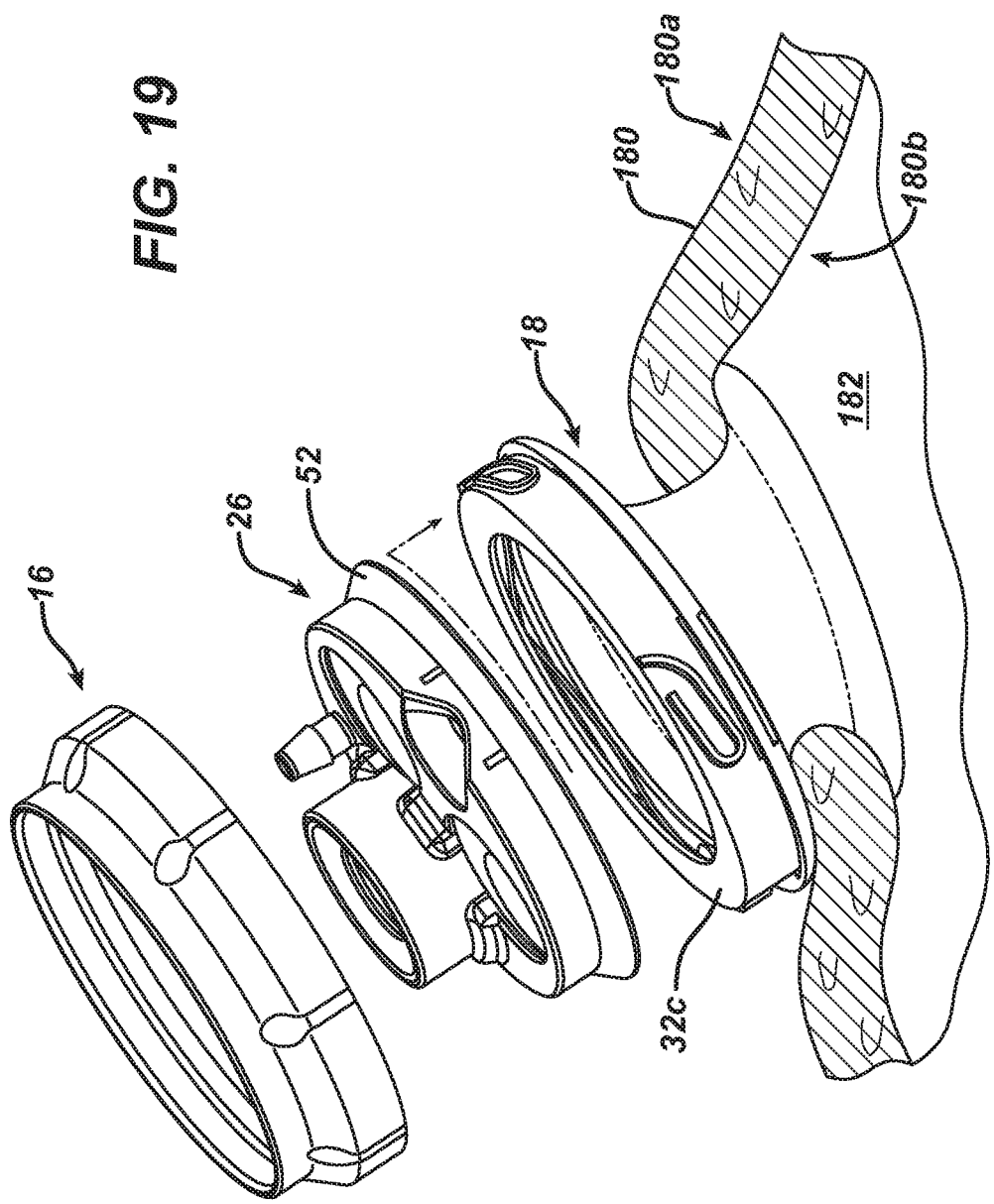
FIG. 19 is a partial cross-sectional, perspective, exploded view of the device of FIG. 18 with a spring assembly positioned in the retractor.
Figure 20:
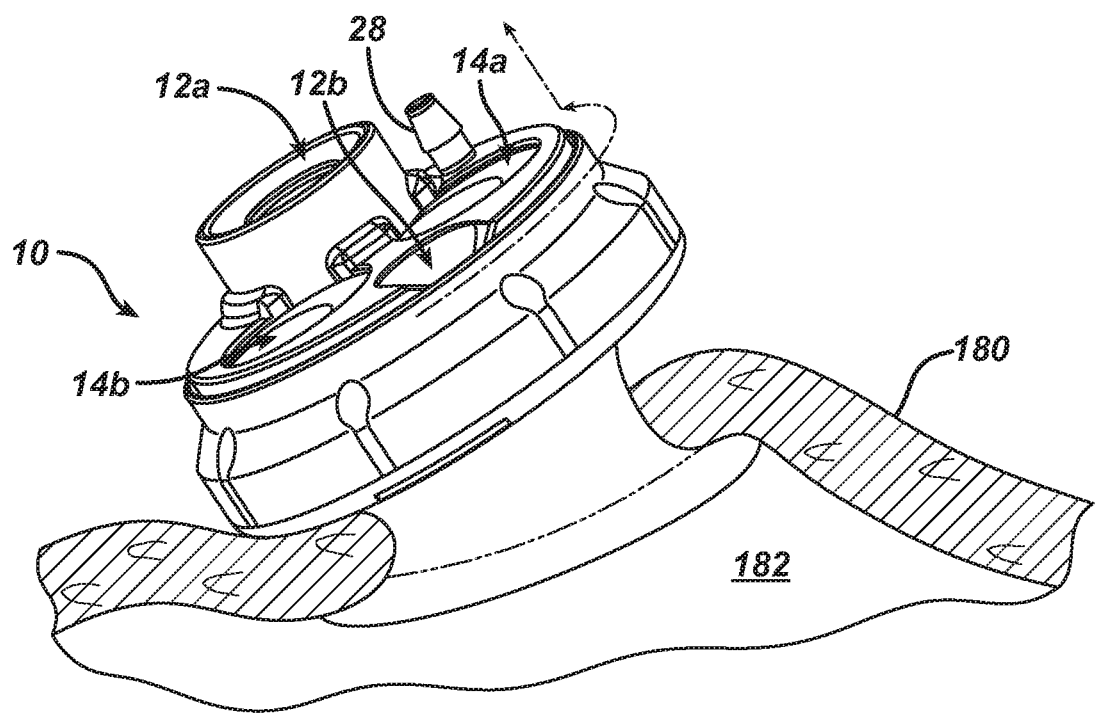
FIG. 20 is a partial cross-sectional, perspective, view of the device of FIG. 19 positioned in the tissue.

As illustrated in one embodiment in FIGS. 18-20, the retractor 18 can be positioned within an opening or incision formed in tissue 180, e.g., in the umbilicus, with proximal and distal flanges 46, 40 of the retractor 18 positioned on opposed sides of the tissue 180. As shown in FIG. 18, the proximal retractor base 38 in the proximal portion of the retractor 18 can be positioned on one side of the tissue 180 with a distal base 38a (see FIG. 5) of the proximal retractor base 38 positioned on and/or proximal to a proximal surface 180a of the tissue 180. The distal flange 40 of the retractor 18 can be positioned on and/or distal to a distal surface 180b of the tissue 180 in a body cavity 182 underlying the tissue 180. The inner elongate portion 42 of the retractor 18 can thereby be positioned within the tissue 180 with an inner lumen or working channel 35 of the retractor 18 extending through the tissue 180 to provide a path of access to the body cavity 182.

With the retractor 18 positioned in the tissue 180, the spring assembly 32 can be positioned within the proximal retractor base 38 with the distal spring retaining ring 32a engaging the interior ledge 54 of the proximal retractor base 38, as illustrated in FIG. 19. The seal spring 32b can be positioned proximal to the distal spring retaining ring 32a with the proximally extending portions 56a of the seal spring 32b positioned above or proximal to the distal spring retaining ring's dimples 58. The proximal spring retaining ring 32c can be positioned proximal to the seal spring 32b with the proximal spring retaining ring's dimples 60 positioned above or proximal to the distally extending portions 56b of the seal spring 32b. A person skilled in the art will appreciate that although the spring assembly 32 is shown in FIG. 19 fully disposed in the proximal retractor base 38, because the spring assembly 32 can be resilient, the spring assembly 32 can partially extend out of the proximal retractor base 38 until the seal base 26 and the housing 16 are attached to the retractor 18. In some embodiments, the spring assembly 32 can be resilient and/or sized large enough to not be fully disposed within the proximal retractor base 38 even with the seal base 26 and the housing 16 attached to the retractor 18.

With the retractor 18 positioned in the tissue 180 and the spring assembly 32 positioned in the retractor 18, the seal base 26 and the housing 16 can be attached to the retractor 18 to fully assemble the device 10, as shown in FIG. 20. If the tissue 180 and/or the retractor 18 are adequately flexible, the retractor 18 can be angled or pivoted as shown in FIGS. 19 and 20 to a desired position to ease attachment of the seal base 26 and the housing 16 to the retractor 18. The retractor 18 can also be angled or pivoted during use of the device 10 with one or more surgical instruments inserted therethrough. To mate the seal base 26 and the housing 16 to the retractor 18, the base 26 can be positioned proximal to the spring assembly 32 with a distal surface of the base 26, e.g., a distal side of the lip 52, engaging the proximal spring retaining ring 32c of the spring assembly 32. In this illustrated embodiment, the base 26 is not configured to lock to the retractor 18 without an engagement and release mechanism releasably locking the housing 16 to the retractor 18, so the base 26 can be held in position while the base 26 is disposed in an inner passageway or working channel 15 extending through the housing 16 and the housing 16 is attached to the retractor 18. As mentioned above, the bayonet pins 34 of the housing 16 can be positioned in the slots 36 of the proximal retractor base 38, and the housing 16 can be rotated relative to the retractor 18 to lock the housing 16 and the base 26 thereto. The tissue 180 can provide adequate tension such that the retractor 18 need not be held in position while the housing 16 is rotated relative thereto, although the retractor 18 can be so held to help provide support to the device 10 during its assembly.

With the surgical access device 10 assembled and positioned in the tissue 180, one or more surgical instruments can be inserted therethrough and into the body cavity 182 where the instruments can help perform any type of surgical procedure. FIGS. 21A, 22A, 23A, 24A, 25A, 26A, and 27A illustrate one embodiment of a suture knot tying procedure using first and second graspers 184a, 184b respectively inserted through the first and second movable sealing ports 14a, 14b and into the body cavity 182. A person skilled in the art will appreciate that the term "grasper" as used herein is intended to encompass any surgical instrument that is configured to grab and/or attach to tissue or other material and thereby manipulate the material, e.g., forceps, retractors, movable jaws, magnets, adhesives, stay sutures, etc. A person skilled in the art will also appreciate that graspers or any other surgical instruments in any combination can be inserted through any of the fixed and movable sealing ports 12a, 12b, 14a, 14b in the device 10, e.g., a scoping device, a surgical stapler, a clip applier, a needle knife, a scalpel, a hook knife, a bougie, a catheter, a vacuum, etc. A person skilled in the art will further appreciate that that the device 10 can be used in a surgical procedure in which one or more surgical instruments can be introduced into a body of a patient through one or more natural and/or artificial orifices. For ease of illustration, the tissue 180 in which the device 10 is disposed is not shown in FIGS. 21A, 22A, 23A, 24A, 25A, 26A, and 27A, nor are any devices shown that can be inserted through any of the fixed sealing ports 12a, 12b and the insufflation port 28 during the suture knot tying procedure. In an exemplary embodiment, a scoping device can be inserted through the first fixed sealing port 12a, a tissue retractor can be inserted through the second fixed sealing port 12b, and working instruments, e.g., graspers, cutters, etc., can be inserted through the first and second movable sealing ports 14a, 14b.

Figure 21A:
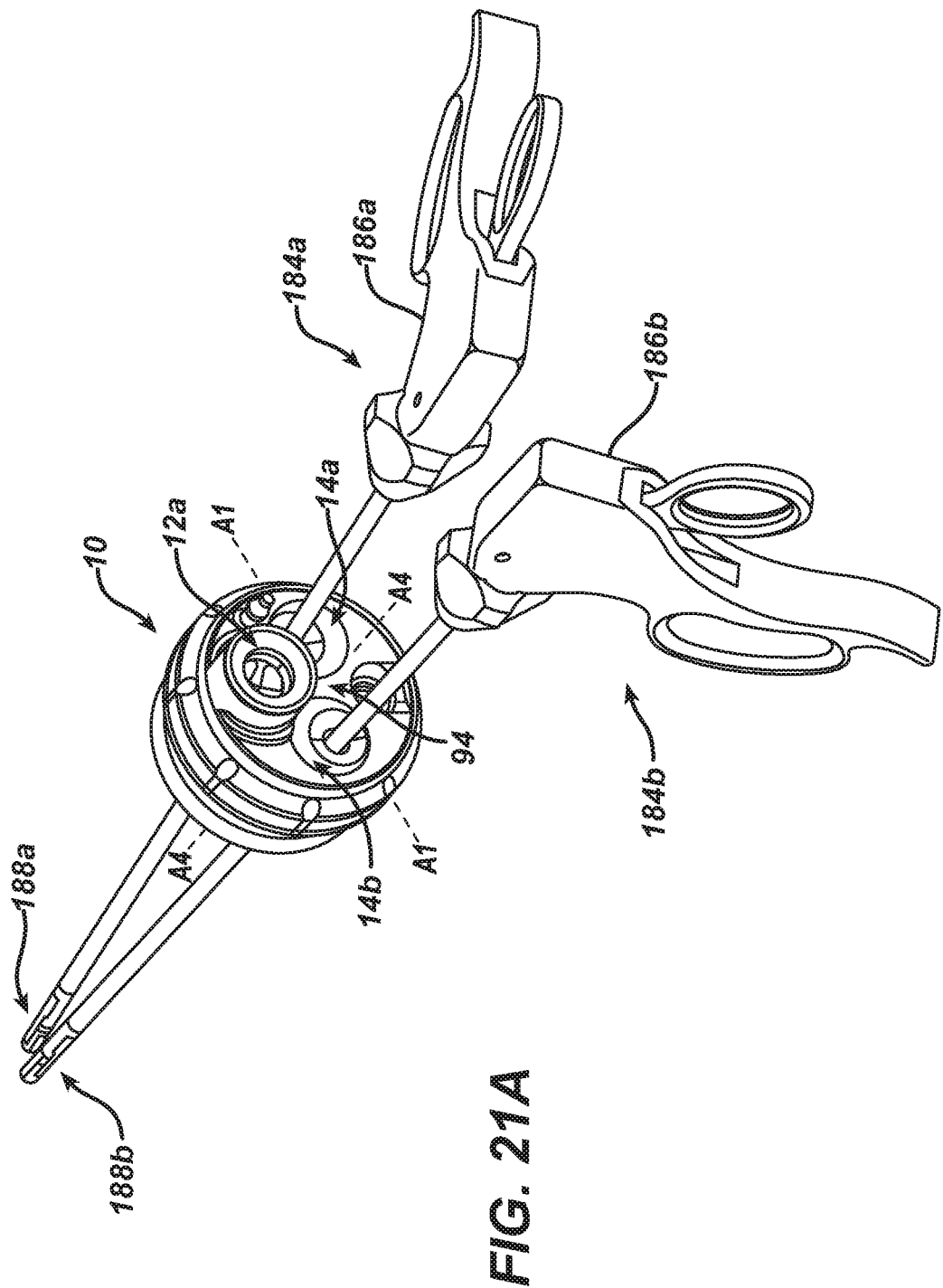
FIG. 21A is a perspective view of first and second surgical instruments each inserted through a movable sealing port in the device of FIG. 20.
Figure 21B:
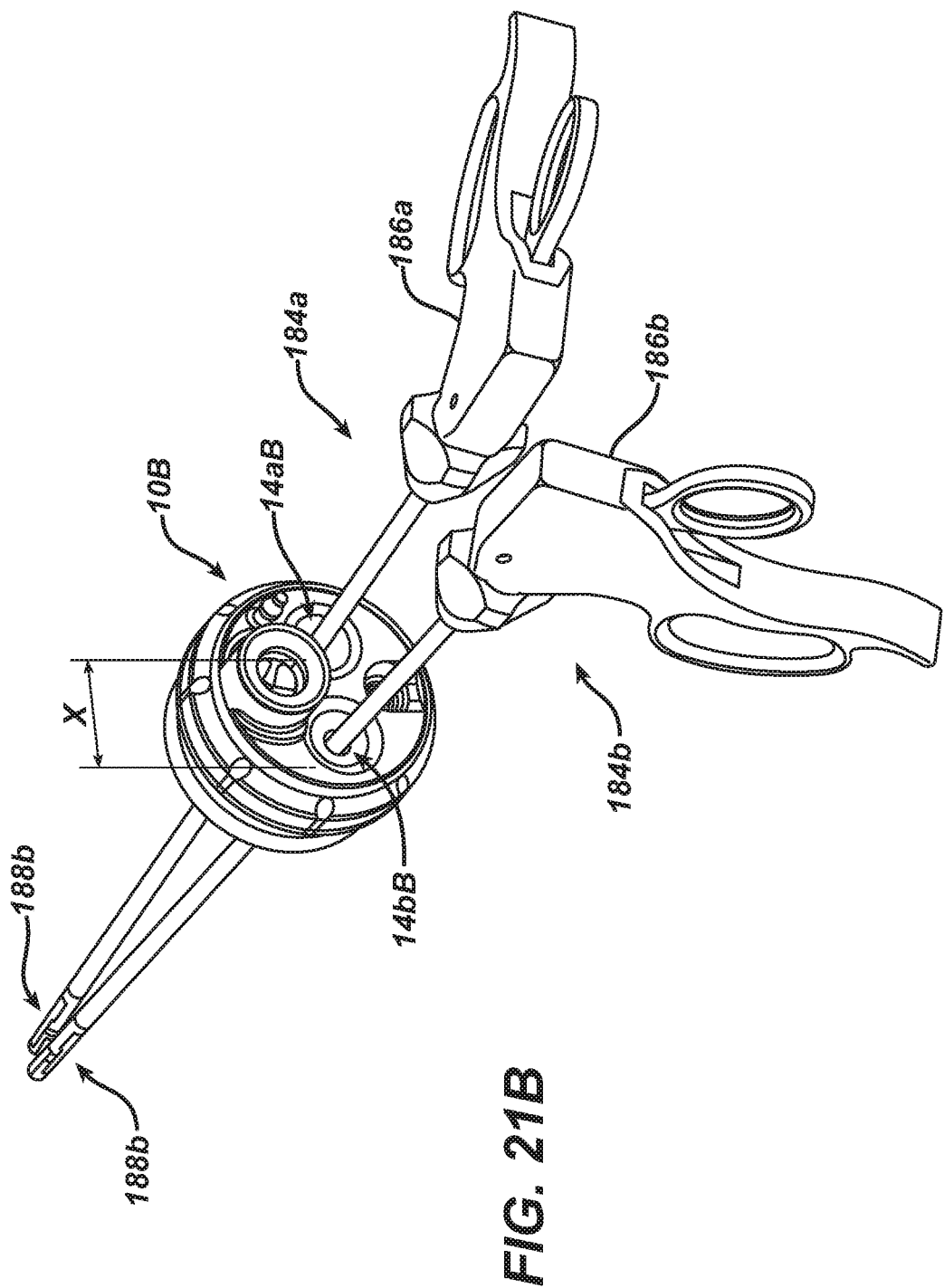
FIG. 21B is a perspective view of first and second surgical instruments each inserted through a fixed sealing port of another embodiment of a surgical access device.
Figure 22A:
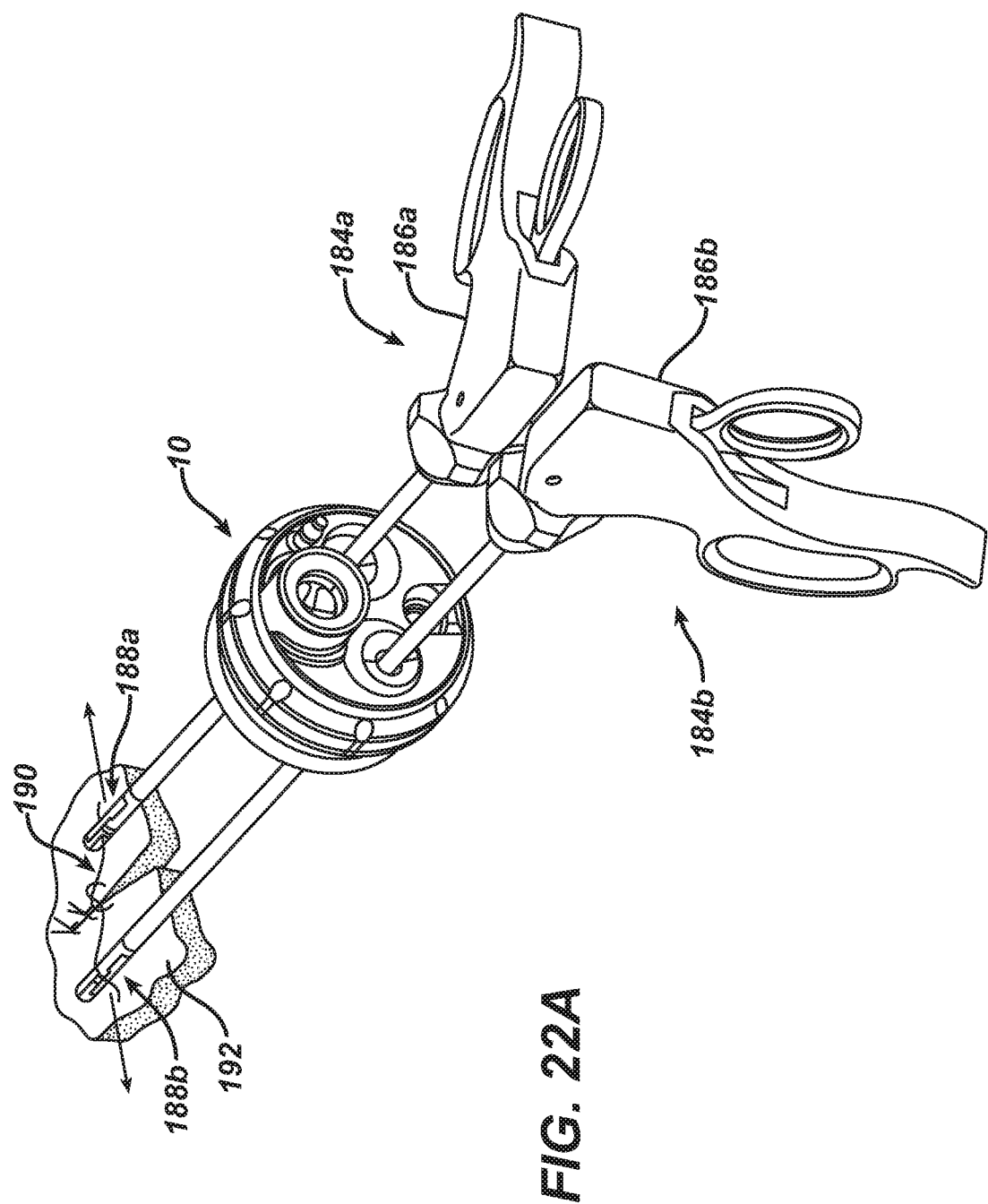
FIG. 22A is a partial cross-sectional, perspective view of the first and second surgical instruments of FIG. 21A with a proximal portion of the first surgical instrument moved closer to a proximal portion of the second surgical instrument and a distal portion of the first surgical instrument moved away from a distal portion of the second surgical instrument.

As illustrated in FIG. 21A, the first and second graspers 184a, 184b can be inserted through the first and second movable sealing ports 14a, 14b, which have dynamically positioned themselves relative to the base 26. As discussed above, the movable sealing ports 14a, 14b can adjust to any dynamic position within their respective port openings 80c, 80d, but as shown, the first movable sealing element can be positioned a shorter distance from the first fixed sealing port 14a than the second movable sealing element. A proximal handle portion 186a of the first grasper 184a can be, as shown in FIG. 21A, positioned proximal to a proximal handle portion 186b of the second grasper 184b with distal working ends 188a, 188b of the respective first and second graspers 184a, 184b positioned a distance. In other words, the first grasper 184a can be vertically displaced from the second grasper 184a in a proximal direction parallel to a vertical or axial axis A4 of the base 26 passing through the center-point 94 of the base 26. To help knot a suture 190 in a cut tissue 192 accessible in the body cavity 182, at least one of the first and second grasper handle portions 186a, 186b can be horizontally or radially displaced from a position parallel to the first axis A1 to increase a distance between the distal working ends 188a, 188b as shown by the directional arrows in FIG. 22. As one or both of the handle portions 186a, 186b are moved, they can come into contact with one other as illustrated in FIG. 22A, which can prevent further horizontal movement of the handle portions 186a, 186b and hence the distal working ends 188a, 188b of the graspers 184a, 184b. To reduce interference between the handle portions 186a, 186b, the first grasper handle 186a can be vertically moved in a proximal direction relative to the second grasper handle 186b, thereby allowing for additional horizontal displacement of the first distal working end 188a relative to the second distal working end 188b as indicated by the directional arrow in FIG. 23A. Such horizontal displacement between the distal working ends 188a, 188b can allow the suture 190 to be tightened and knotted against the cut tissue 192.

Figure 24A:
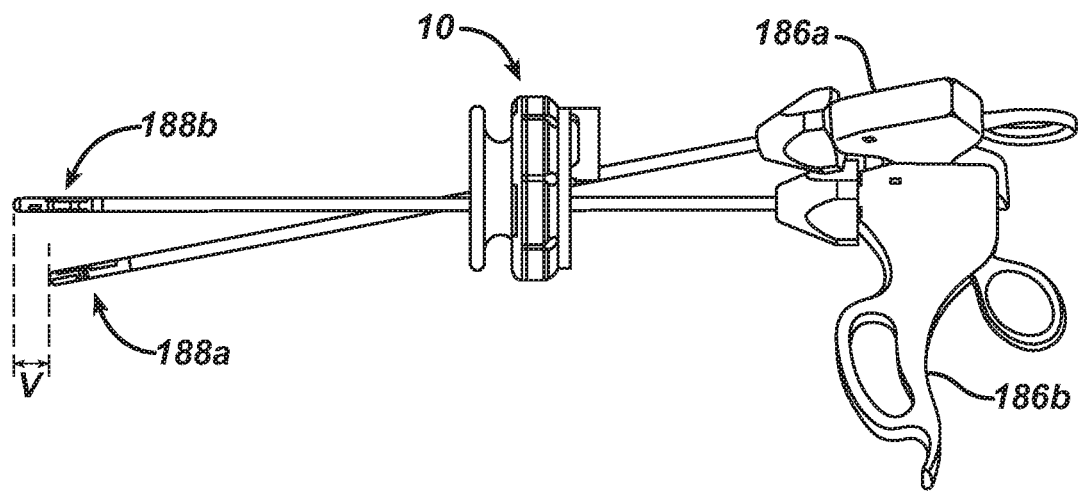
FIG. 24A is a side view of the first and second surgical instruments inserted through the device of FIG. 23A.
Figure 24B:
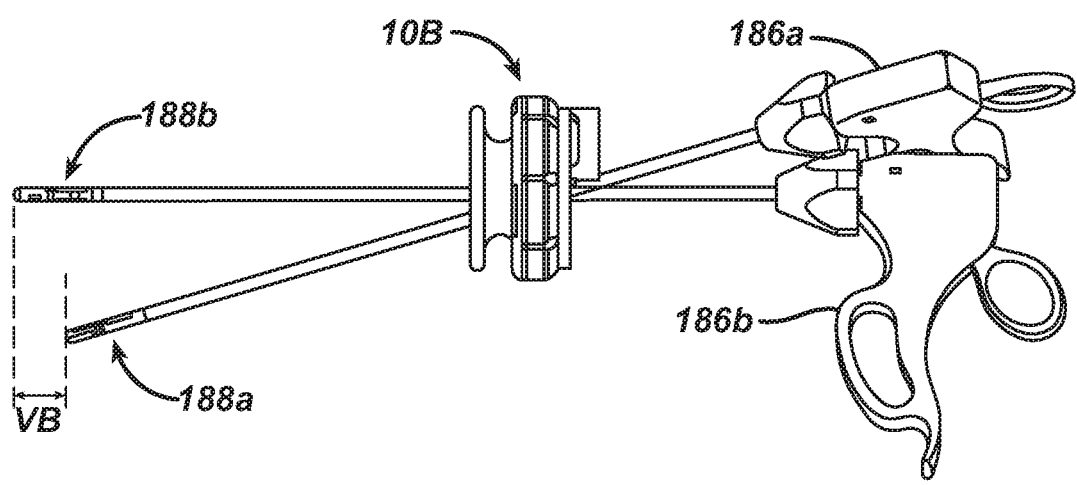
FIG. 24B is a side view of the first and second surgical instruments inserted through the device of FIG. 23B.
Figure 25A:
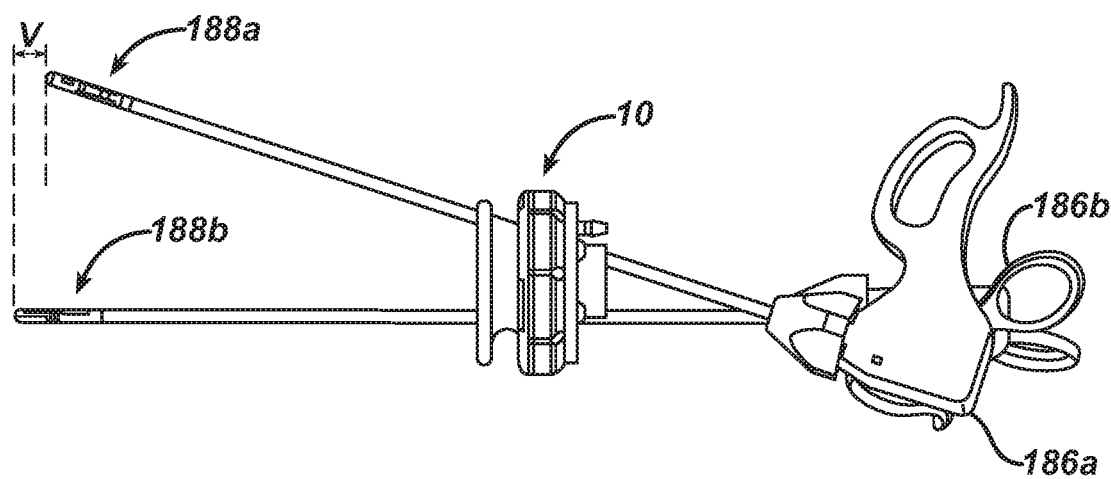
FIG. 25A is another side view of the first and second surgical instruments inserted through the device of FIG. 23A.
Figure 25B:
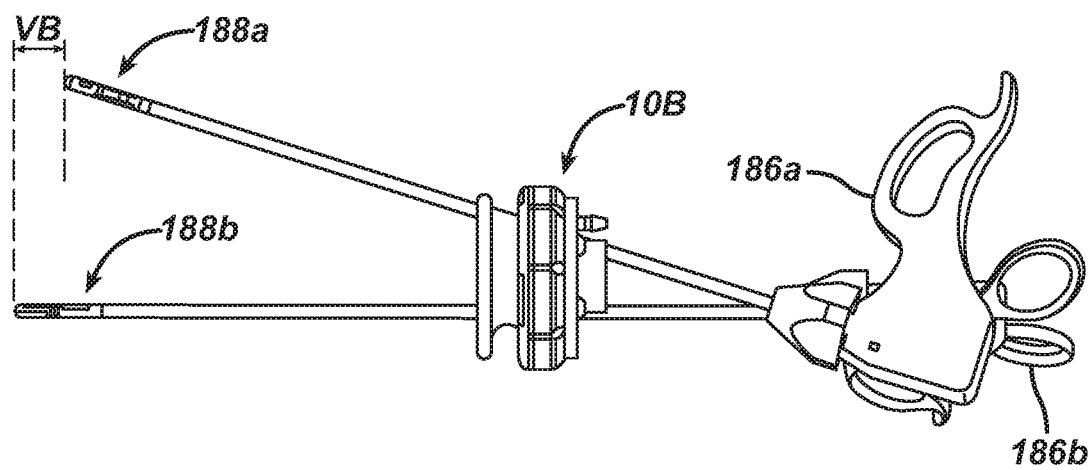
FIG. 25B is another side view of the first and second surgical instruments inserted through the device of FIG. 23B.
Figure 26A:
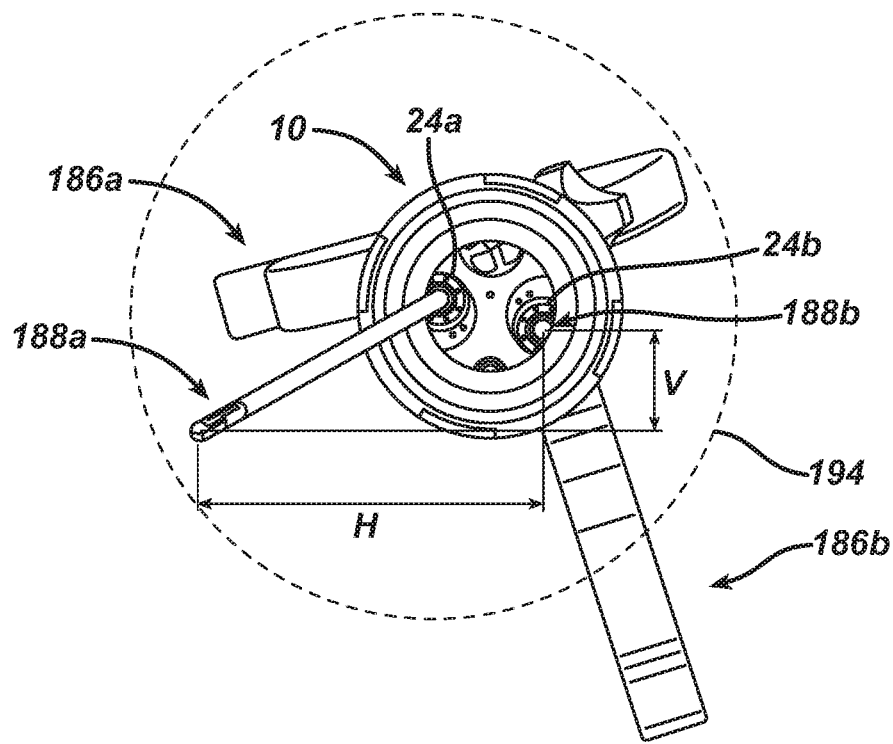
FIG. 26A is a bottom view of the first and second surgical instruments inserted through the device of FIG. 23A.
Figure 27A:
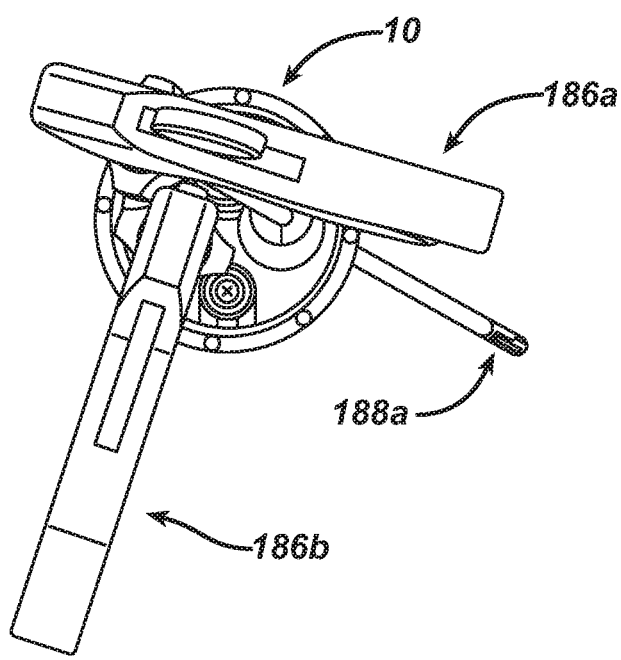
FIG. 27A is a top view of the first and second surgical instruments inserted through the device of FIG. 23A.
Figure 26B:
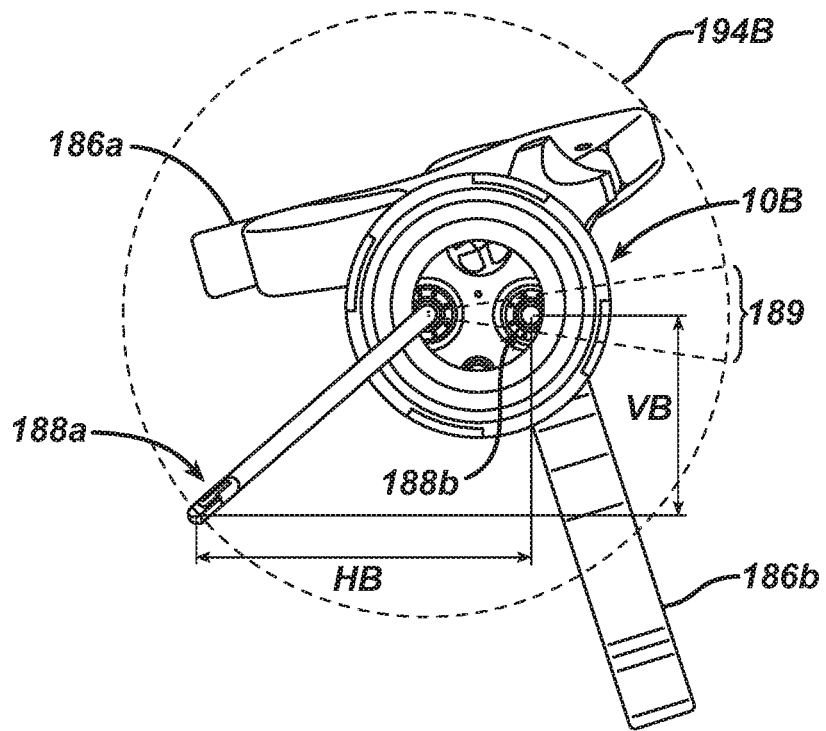
FIG. 26B is a bottom view of the first and second surgical instruments inserted through the device of FIG. 23B.
Figure 27B:
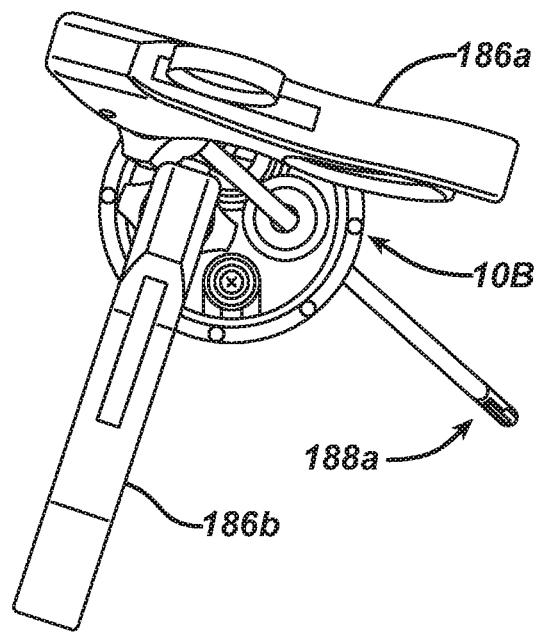
FIG. 27B is a top view of the first and second surgical instruments inserted through the device of FIG. 23B.

Because of the movable configuration of the movable sealing ports 14a, 14b that allows their respective sealing elements to move relative to the base 26 and the housing 16, instruments inserted through the movable sealing ports 14a, 14b can minimally move vertically and/or horizontally while used in a surgical area that can have a limited working space, particularly in minimally invasive surgical procedures. In the illustrated suture tying procedure, the first grasper handle portion 186a need not be vertically displaced by a significant amount relative to the second grasper handle portion 186b to provide for adequate horizontal displacement of the distal working ends 188a, 188b. The distal working ends 188a, 188b can thus, as illustrated in FIGS. 24A, 25A and 26A, be separated by a relatively small vertical distance V and a relatively small horizontal distance H. The proximal handle portions 184a, 184b can also be separated by a relatively small vertical distance, as illustrated in FIG. 27A. Despite being configured to reduce the need for vertical and horizontal movement of instruments inserted through the movable sealing ports 14a, 14b, the movable sealing ports 14a, 14b can nevertheless be configured to allow for a 360° working area for surgical instruments inserted therethrough. In the illustrated suture tying procedure, as shown in FIG. 26A, the first and second graspers 184a, 184b can be movable through movement of any one or more of the movable sealing ports 14a, 14b and the base 26 to access any location within a circular perimeter 194 with which the device 10 is eccentric or concentric.

Figure 22B:
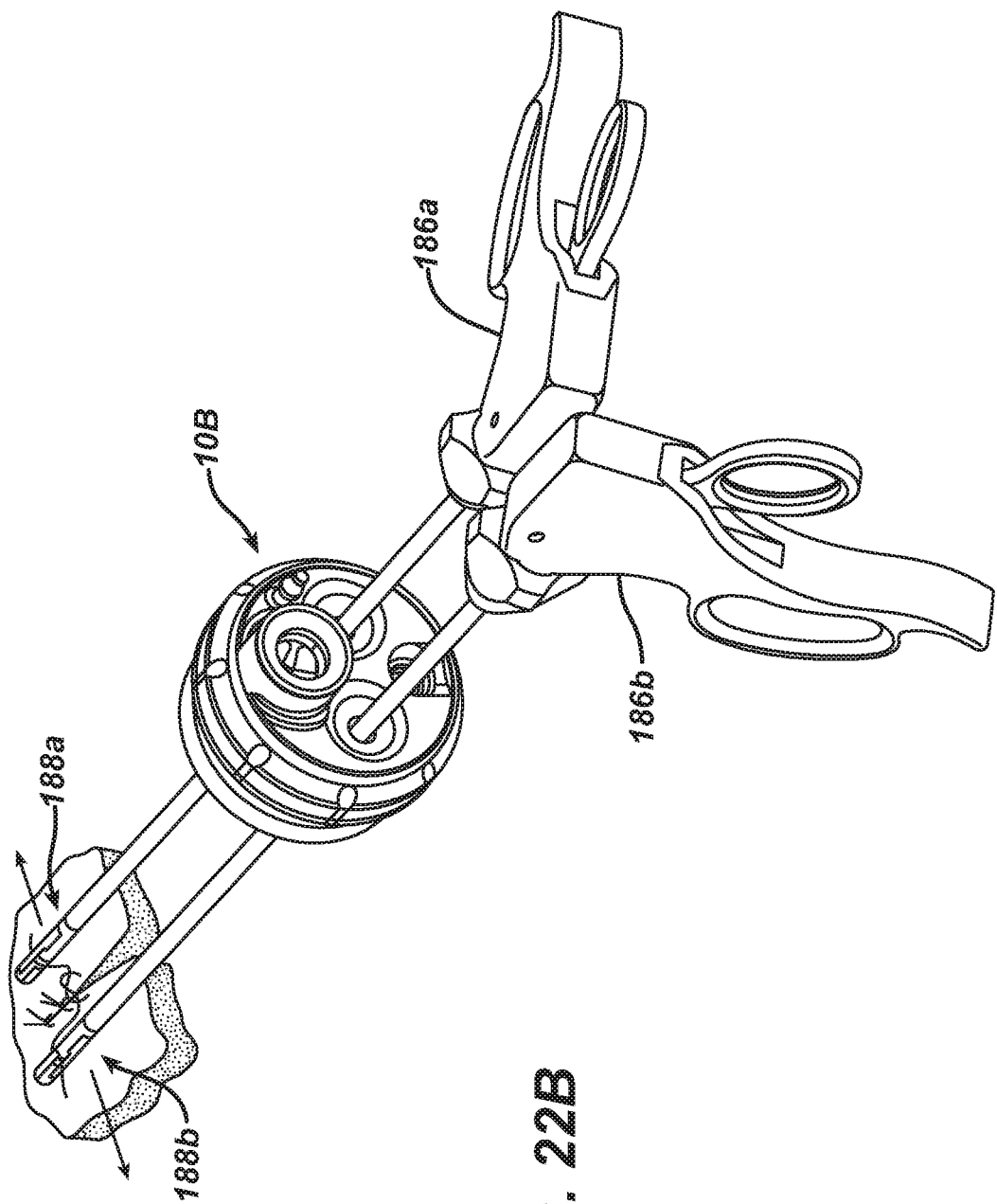
FIG. 22B is a partial cross-sectional, perspective view of the first and second surgical instruments of FIG. 21B with a proximal portion of the first surgical instrument moved closer to a proximal portion of the second surgical instrument and a distal portion of the first surgical instrument moved away from a distal portion of the second surgical instrument.
Figure 23A:
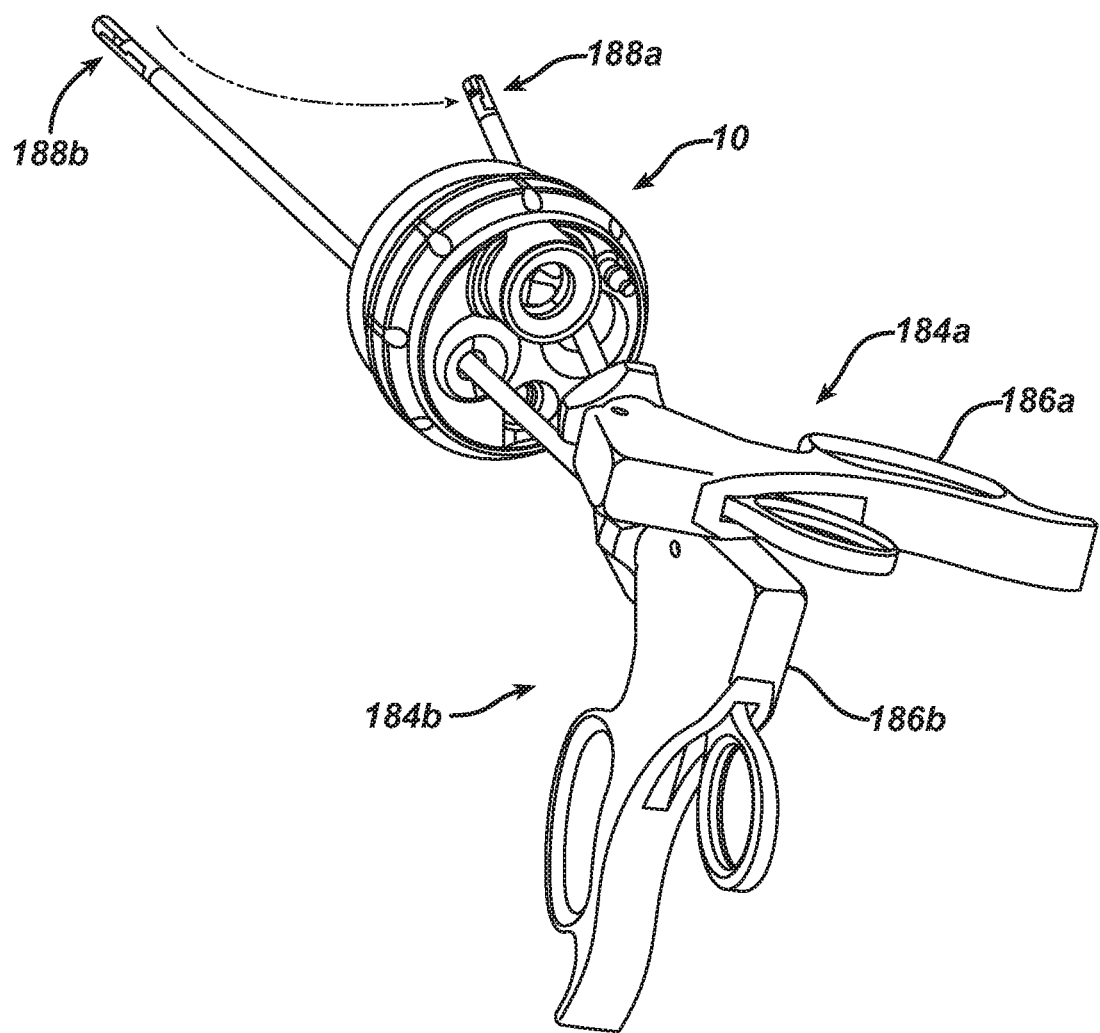
FIG. 23A is a perspective view of the first and second surgical instruments of FIG. 22A with the proximal portion of the first surgical instrument moved vertically and horizontally relative to the proximal portion of the second surgical instrument and the distal portion of the first surgical instrument moved vertically and horizontally relative to the distal portion of the second surgical instrument.
Figure 23B:
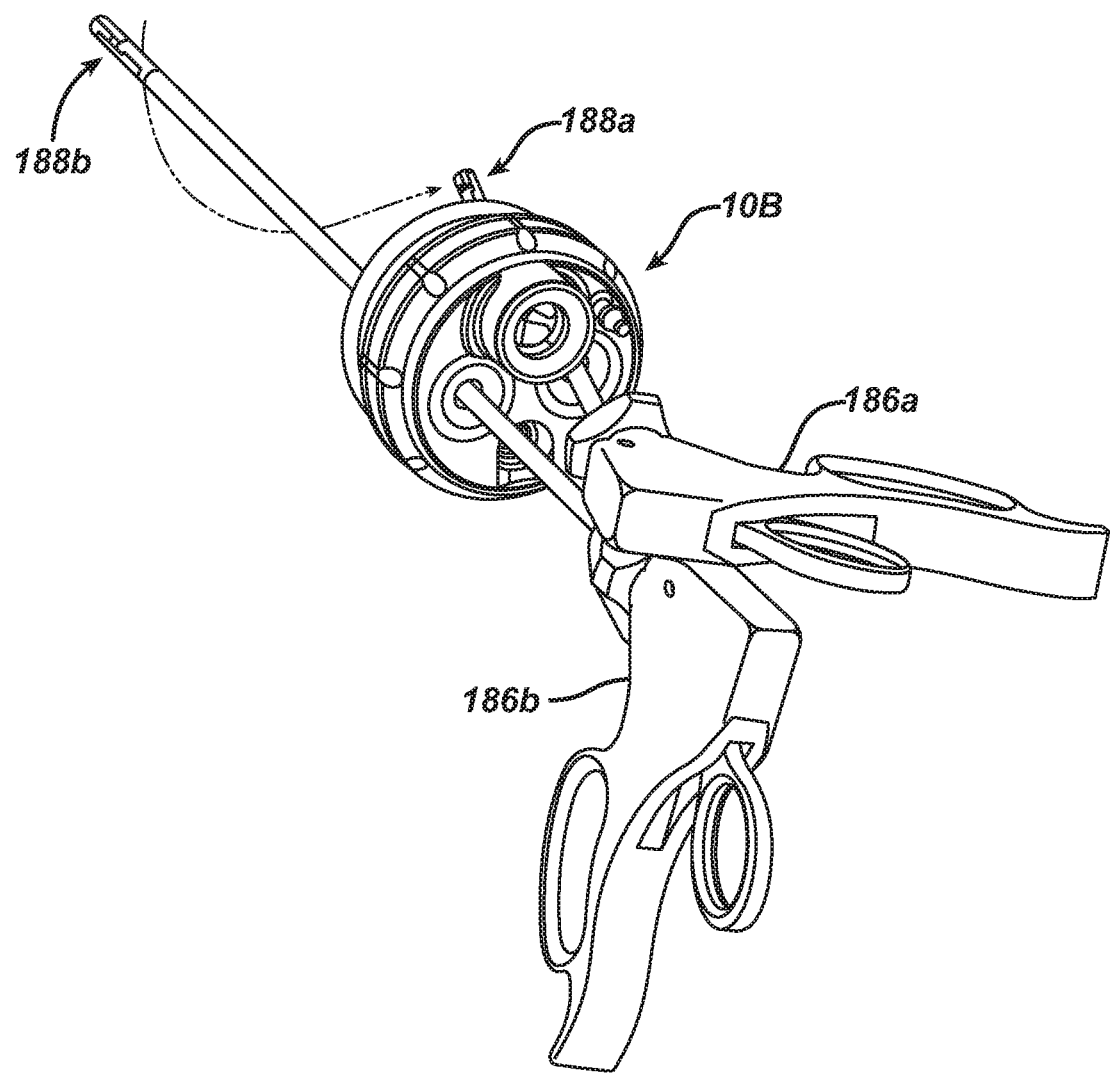
FIG. 23B is a perspective view of the first and second surgical instruments of FIG. 22B with the proximal portion of the first surgical instrument moved vertically and horizontally relative to the proximal portion of the second surgical instrument and the distal portion of the first surgical instrument moved vertically and horizontally relative to the distal portion of the second surgical instrument.

In contrast, FIGS. 21B, 22B, 23B, 24B, 25B, 26B, and 27B, which respectively correspond to FIGS. 21A, 22A, 23A, 24A, 25A, 26A, and 27A, illustrate the first and second graspers 184a, 184b inserted through a surgical access device 10B configured similar to the surgical access device 10 but, instead of having the first and second movable sealing ports 14a, 14b, has first and second fixed sealing ports 14aB, 14bB having a fixed distance X therebetween. Moving the first grasper 184a horizontally, as shown in FIG. 22B, results in interference between the first and second graspers 184a, 184b. Moving the first grasper handle portion 186a horizontally and vertically as illustrated in FIG. 23B can provide clearance of the first grasper 184a around the second grasper 184b, but as shown in FIGS. 24B, 25B, 26B, and 27B, movement of the first grasper 184a around the second grasper 184b is limited. A horizontal distance HB between the distal working ends 188a, 188b can be substantially the same as discussed above for the graspers 184a, 184b inserted through the device 10, but a vertical distance VB between the distal working ends 188a, 188b is larger than the vertical distance V for the graspers 184a, 184b inserted through the device 10. Additionally, the distal working ends 188a, 188b inserted though the first and second fixed sealing ports 14aB, 14bB cannot access a 360° working area around the device 10B but instead have an inaccessible "pie slice" 189 in a circular perimeter 194B with which the device 10B is eccentric or concentric.

At any point before, during, or after a surgical procedure, the housing 16, the base 26, and the spring assembly 32 can be released from the retractor 18, and the retractor 18 can be removed from the tissue 180. To disengage the housing 16 from the retractor 18, the housing 16 can be rotated relative to the housing 16 in the opposite direction from which the housing 16 was rotated to attach the housing 16 to the retractor 18, e.g., in a counter clockwise direction as shown by the dotted directional arrow in FIG. 20. The engagement and release mechanism can thereby be disengaged, e.g., the bayonet pins 34 can be disengaged from the slots 36, to allow the housing 16 to be removed from the retractor 18, also as shown by the directional arrow in FIG. 20. As mentioned above, the tissue 180 can provide adequate tension for the rotational motion of the housing 16.

Figure 28:
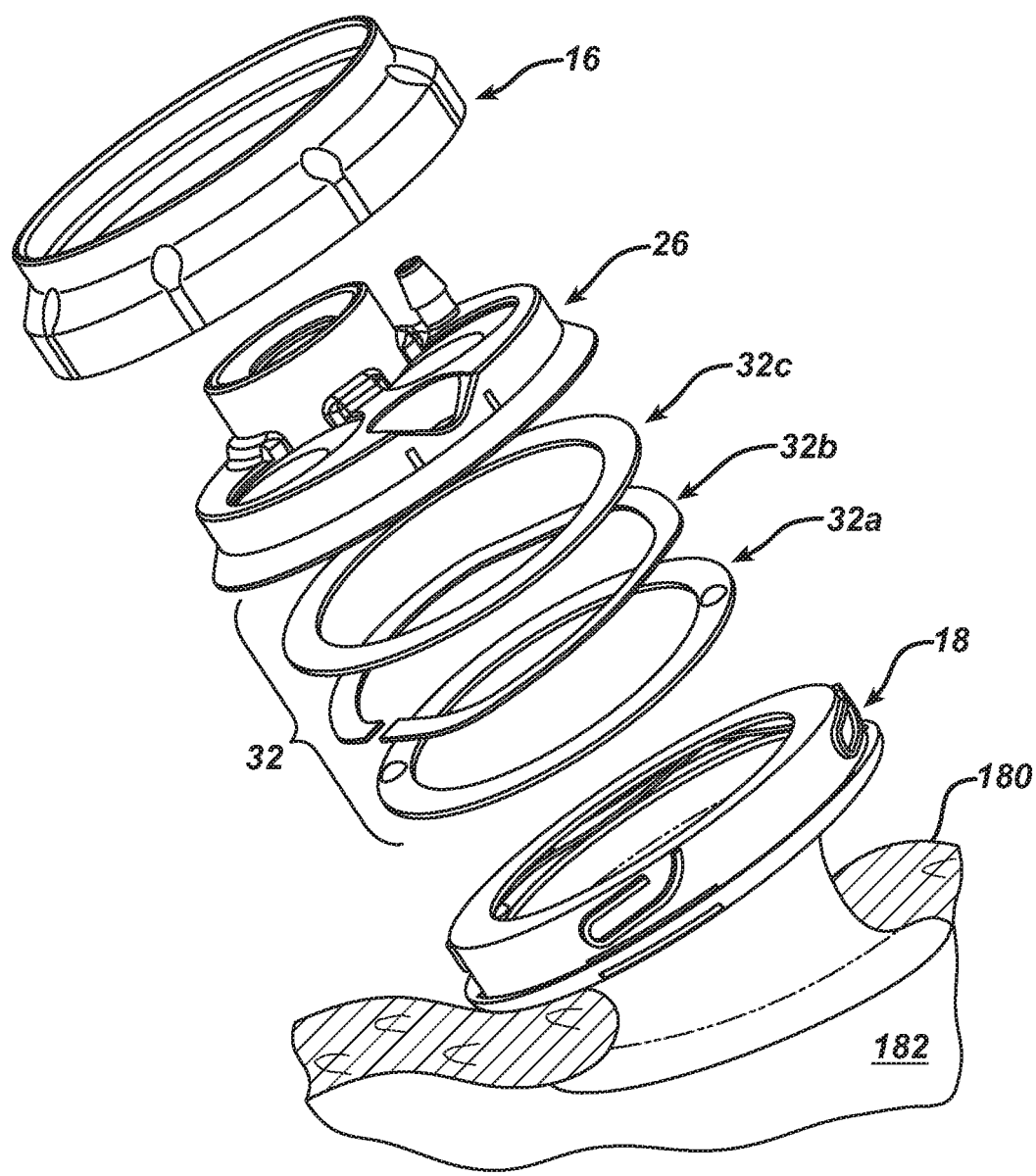
FIG. 28 is a partial cross-sectional, perspective, exploded view of the device of FIG. 1 with the retractor deformed in tissue.
Figure 29:
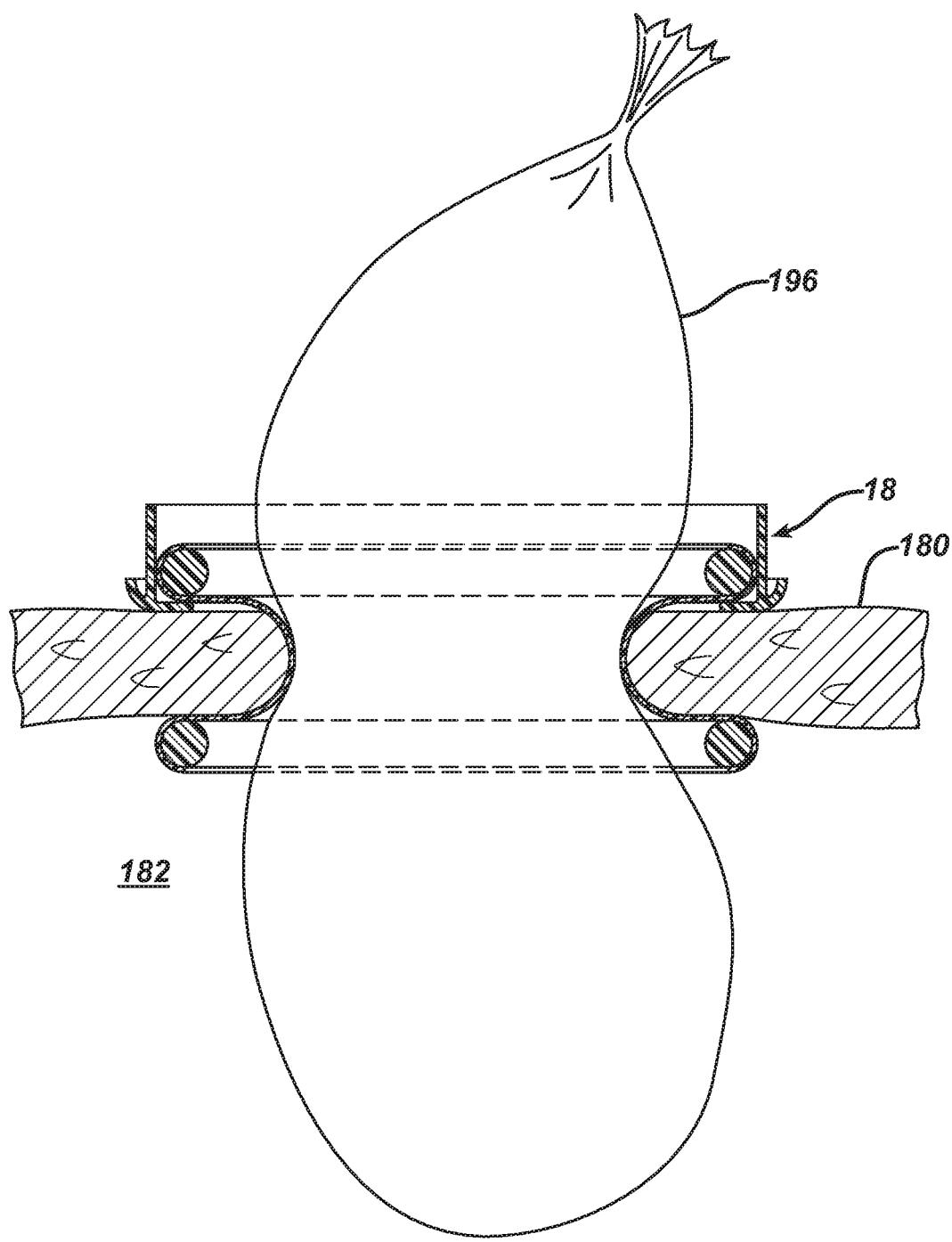
FIG. 29 is a partial cross-sectional, side view of the device of FIG. 28 with a waste disposal bag passing through a working channel of the retractor positioned in tissue.
Figure 30:
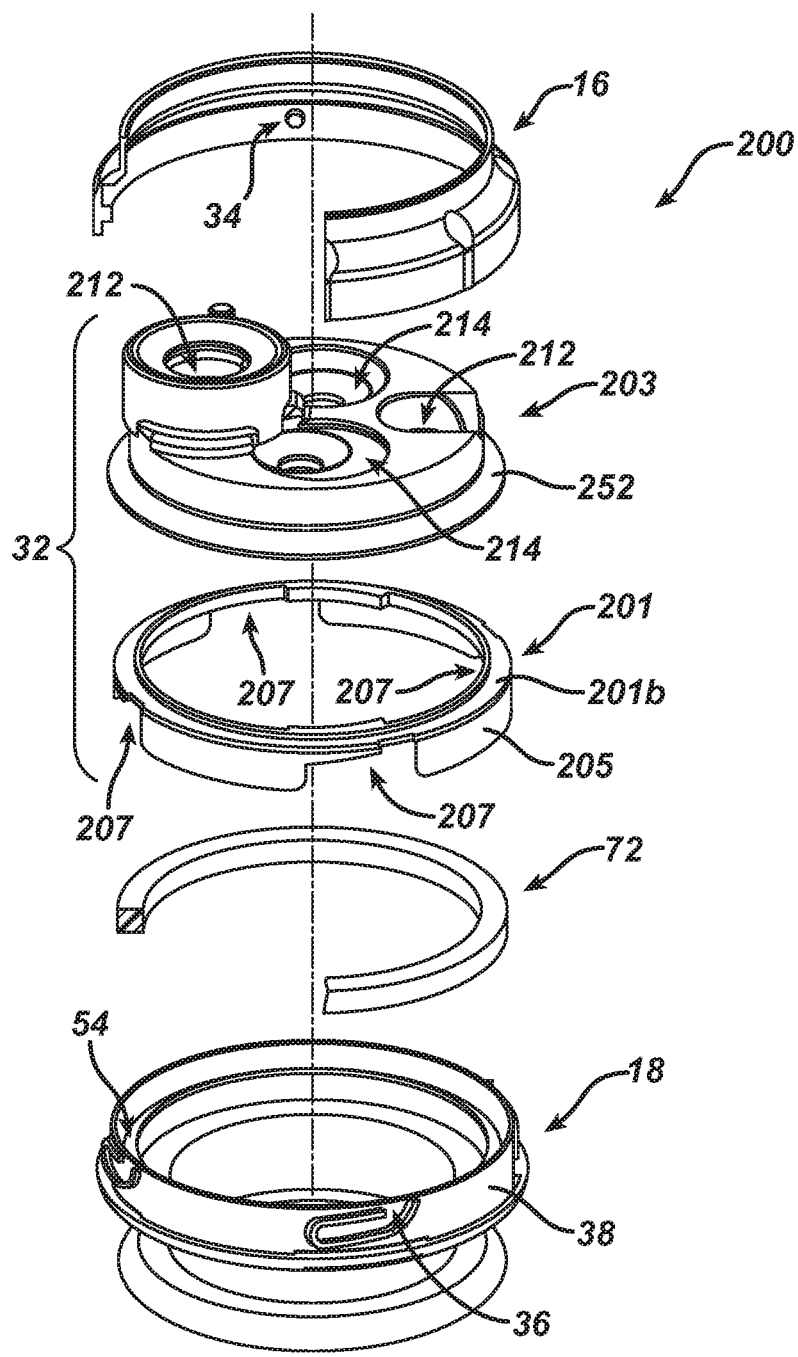
FIG. 30 is a partial cut-away, exploded view of another embodiment of a surgical access device.
Figure 31:
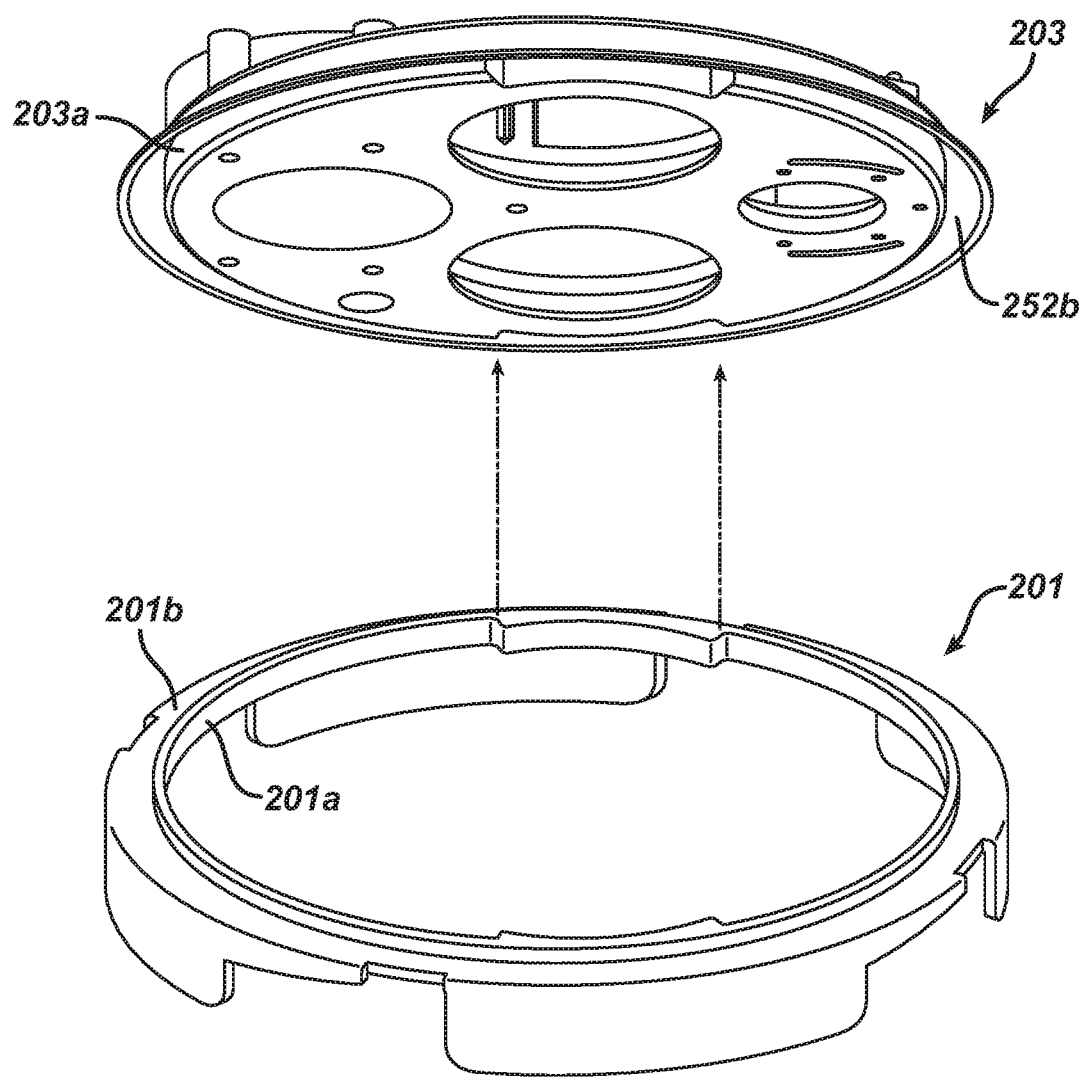
FIG. 31 is an exploded view of a seal base of the device of FIG. 30.
Figure 32:
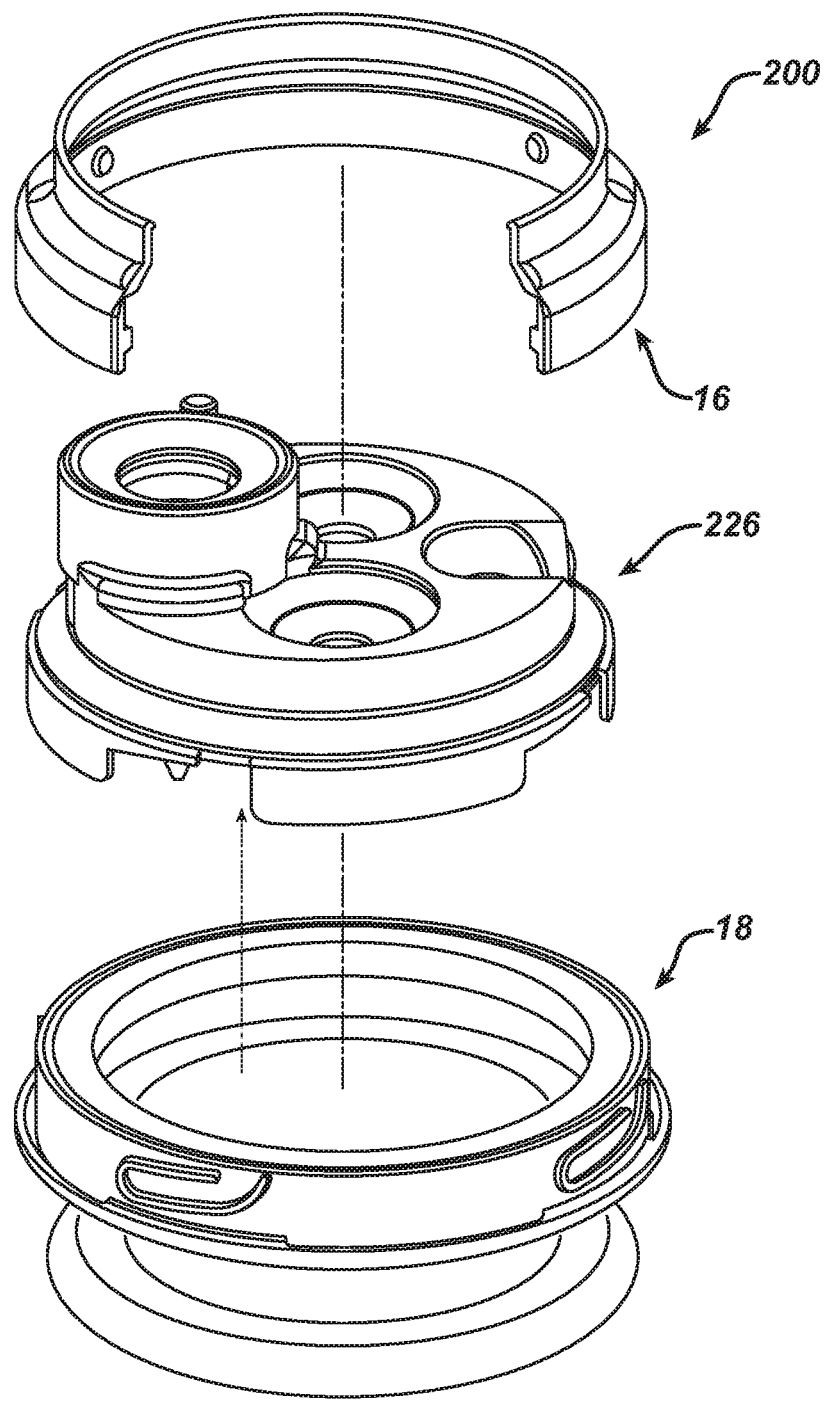
FIG. 32 is an exploded view of the device of FIG. 30 with a spring assembly positioned in a retractor.

With the housing 16 disengaged from the retractor 18, the base 26 and the spring assembly 32 can be proximally lifted and removed from engagement with the retractor 18, as illustrated in FIG. 28 with the base 26 and the spring assembly 32. With the proximal portion 30 of the device 10 disengaged from the retractor 18, the retractor 18 through the working channel 35 can still provide access to the body cavity 182 underlying the tissue 180. One or more surgical instruments can be advanced through the working channel 35, such as a waste removal bag 196 configured to hold waste material, e.g., dissected tissue, excess fluid, etc., from the body cavity 182. The bag 196 can be introduced into the body cavity 182 through the retractor's working channel 35 or other access port. A person skilled in the art will appreciate that one or more surgical instruments can be advanced through the retractor's working channel 35 before and/or after the proximal portion 30 of the device 10 has been attached to the retractor 18.

FIGS. 30-33 illustrate another exemplary embodiment of a surgical access device 200 that includes at least one fixed sealing port and at least one movable sealing port. The surgical access device 200 can be configured and used similar to the surgical access device 10 discussed above and can include the housing 16, the singular seal member 72 of FIG. 15, and the retractor 18. The device 200 can also include a seal base 226 including a proximal portion 203 similar to the seal base 26 and the proximal portion 26a discussed above. However, in this embodiment a distal portion of the seal base 226 is in the form of a guide ring 201 attached to the proximal portion 203. A proximal attachment surface 201a of the guide ring 201 can be fixedly attached to a distal attachment surface 203a of the proximal seal base 203 with a distal surface 252b of a lip 252 extending from the proximal seal base 203 seated on an upper outer perimeter 201b of the guide ring 201. As will be appreciated by a person skilled in the art, the guide ring 201 and the proximal seal base 203 can be otherwise fixedly attached together or can be removably attached together. Similar to those discussed above, the seal base 226 can have an insufflation port 228, one or more fixed sealing ports 212, and one or more movable sealing ports 214.

Generally, the guide ring 201 can be configured to help align the housing 16 with the retractor 18. The guide ring 201 can, as shown in this illustrated embodiment, have a circular shape with a skirt 205 distally extending from the upper outer perimeter 201b of the guide ring 201. The skirt 205 can include a plurality of cut-outs 207 formed therein that are each configured to align with a corresponding one of the slots 36 of the retractor 18 when the base 226 is coupled thereto. The cut-outs 207 can thus each have a size, shape, and position around a perimeter of the guide ring 201 to complement one of the slots 36. One or more of the cut-outs 207, such as each of the cut-outs 207 in this illustrated embodiment, can extend into the guide ring's upper outer perimeter 201b to provide adequate clearance for the bayonet pins 34 on the housing 16 to be disposed in and removed from the slots 36. The seal base 226 can be positioned in a variety of radial configurations with respect to the retractor 18 before and/or after the engagement and release mechanism is engaged to attach the base 226 to the retractor 18, with the cut-outs 207 selectively aligned with any of the slots 36, such as in this illustrated embodiment having four radial configurations about 90° apart using the four equidistantly spaced radial slots 36, pins 34, and cut-outs 207. In this way, the initial position of the seal base 226 can be predictable with respect to the retractor 18 when the housing 16 attaches the seal base 226, which can help desirably position the ports extending through the base 226 with respect to the surgical site.

Figure 33:
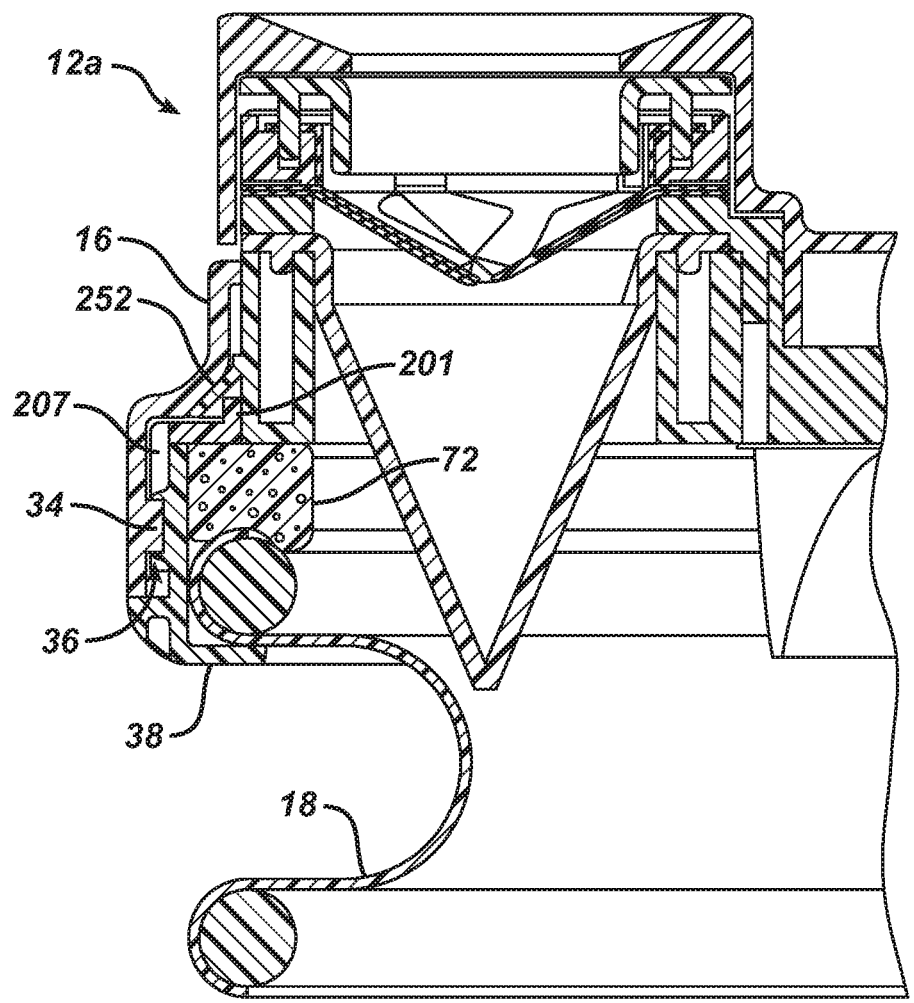
FIG. 33 is a partial cross-sectional view of the assembled device of FIG. 30.

The device 200 can be assembled with or without a portion of the device 200, e.g., the retractor 18, positioned in tissue. To assemble the device 200, the singular seal member 72 can be seated on the interior ledge 54 of the retractor 18 such that the singular seal member 72 is at least partially disposed within the retractor 18. The seal base 226 can be positioned to engage the retractor 18 with the singular seal member 72 positioned therebetween. As illustrated in FIG. 33, the singular seal member 72 can deform to conform to a shape of the retractor 18 and/or the seal base 226. An inner surface of the skirt 205 can be positioned to engage an outer surface of the proximal retractor base 38 such that the cut-outs 207 in the seal base 226 align with and thereby expose the bayonet slots 36. The skirt 205 can help hold the base 226 in position with respect to the retractor 18 until the housing 16 is attached thereto using the pins 34 and rotation of the housing 16 with respect to the retractor 18.

Figure 34:
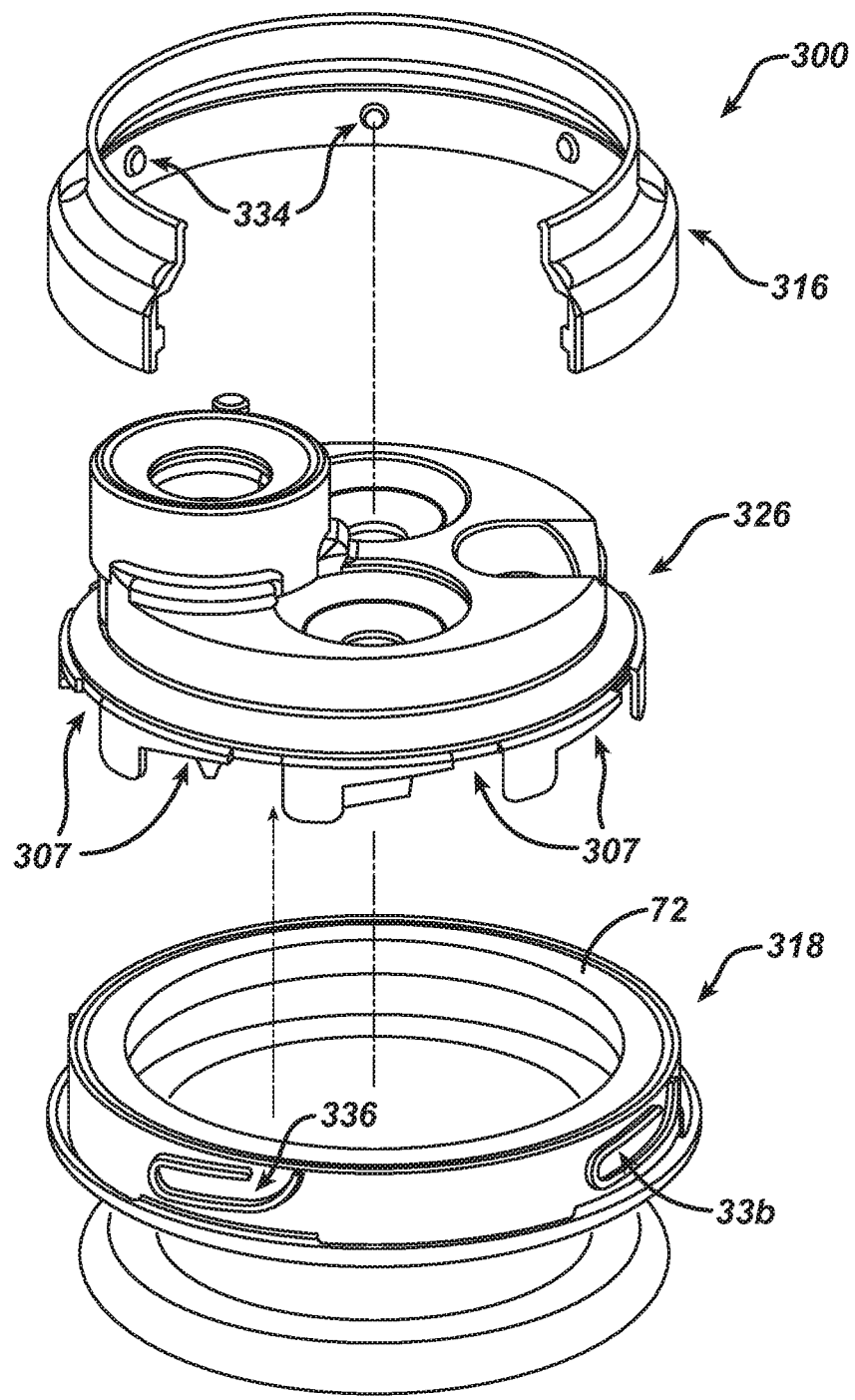
FIG. 34 is an exploded view of yet another embodiment of a surgical access device.

In another exemplary embodiment of a surgical access device 300, illustrated in FIG. 34, the device 300 can be configured and used similar to the device 10 discussed above with a housing 316, a seal base 326 having at least one fixed sealing port and at least one movable sealing port, the singular seal member 72 of FIG. 15, and a retractor 318. The seal base 226 of FIGS. 30-33 can allow four radial positions, while the seal base 326 can include a modified guide ring 301 configured to allow the seal base 326 including the modified guide ring 301 to be positioned in eight radial configurations about 45° apart with the modified guide ring 301 having eight cut-outs 307 formed in its skirt 305, the housing 316 having eight bayonet pins 334, and the retractor 318 having eight bayonet slots 336.

Figure 35:
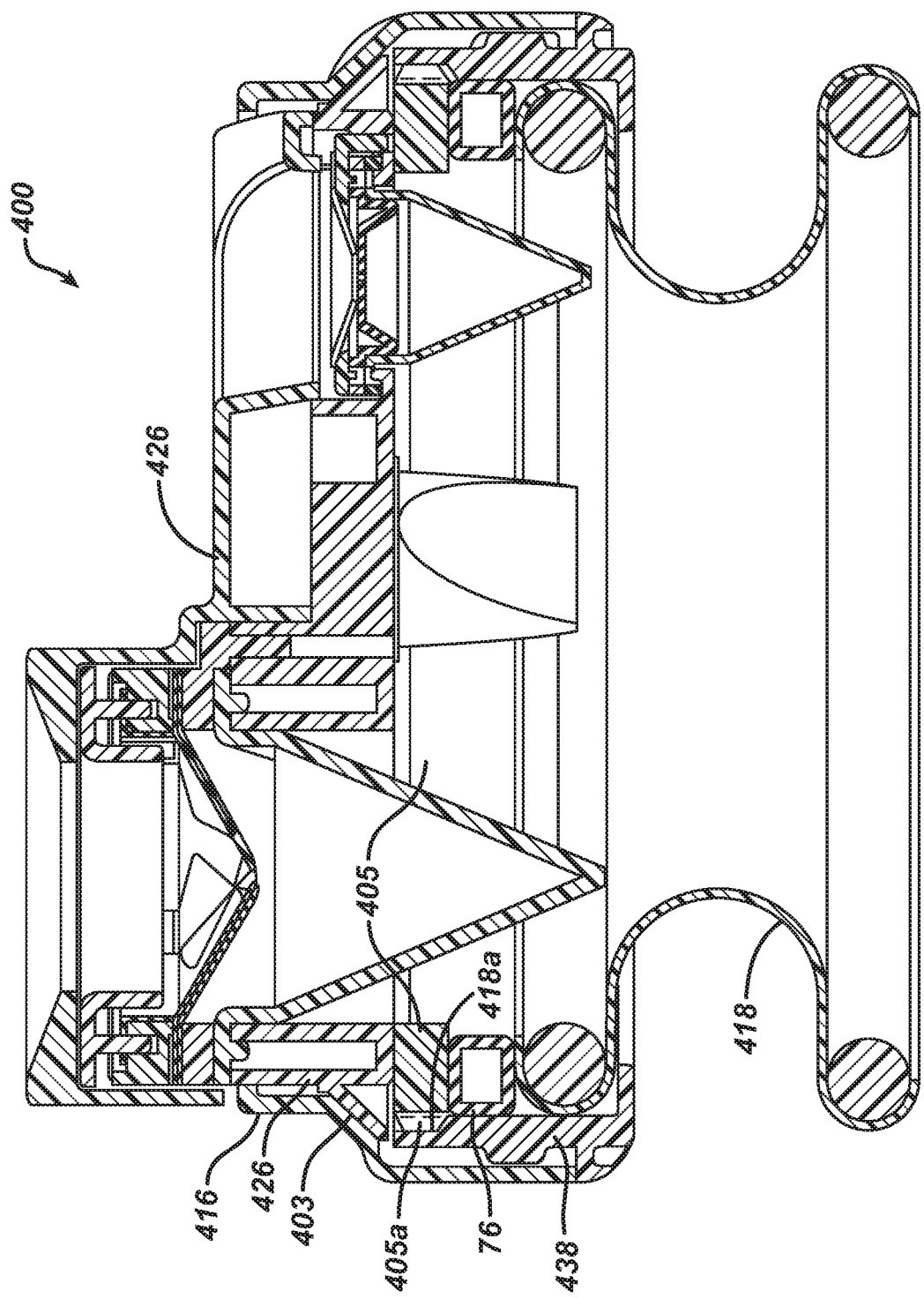
FIG. 35 is a cross-sectional view of another embodiment of a surgical access device.

In yet another exemplary embodiment of a surgical access device 400, illustrated in FIG. 35, a seal base 426 can be configured to be positioned at any location around a perimeter of a retractor 418 prior to attachment of a housing 416 to the retractor 418 to lock the seal base 426 and the housing 416 thereto. The device 400 can be configured and used similar to the device 10 discussed above, including the housing 418, the seal base 426, the hollow singular seal member 76 of FIG. 17, and the retractor 418. In this embodiment of the device 400, a proximal retractor base 438 of the retractor 38 can be configured to engage the seal base 426 using an interlocking mechanism. The interlocking mechanism can generally be configured to allow the seal base 426 to be predictably positioned at any location around the perimeter of the retractor 418, and in this illustrated embodiment includes interlocking teeth. The seal base 426 can include a proximal portion 403 similar to the seal base 26 and a distal portion in the form of a clocking ring 405 attached to the proximal portion 403. The clocking ring 405 can be configured similar to the skirt 205 of FIG. 30 but it can extend around a perimeter of the clocking ring 405 without any cut-out portions. An external surface of the clocking ring 405 can include teeth 405a configured to engage corresponding teeth 418a formed on an inner surface of the retractor 418, e.g., on an internal surface of a proximal retractor base 438 of the retractor 418. In this way, the seal base 426 can be positioned relative to the retractor 418 in a desired position anywhere 360° around the retractor 418 prior to attachment of the housing 416 to the retractor 418 to lock the base 426 thereto. The proximal retractor base 438 can have a thickened wall to help accommodate the teeth 418a, which can be integrally formed therewith.

Figure 36:
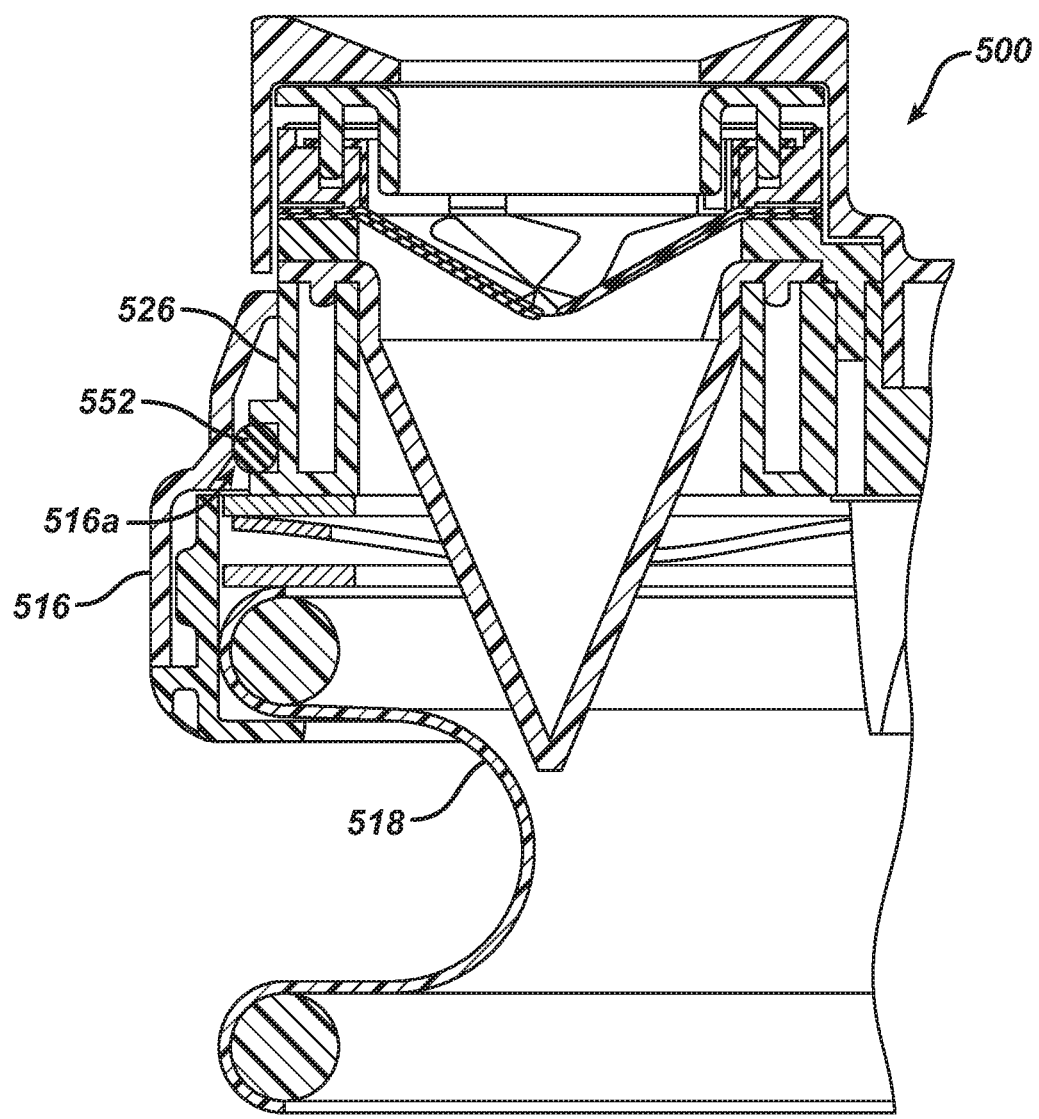
FIG. 36 is a partial cross-sectional view of yet another embodiment of a surgical access device.

The above exemplary embodiments of surgical access devices 10, 200, 300, 400 can each include a circumferential distal lip, e.g., the lip 52 of the device 10, configured to help provide a seal between the seal base and the retractor to which it is releasably attached. In another embodiment of a surgical access device 500, illustrated in FIG. 36, an o-ring 552 can be configured to be seated between a seal base 526 and a retractor 518 to help provide a seal therebetween. A housing 516 configured to couple the base 526 and the retractor 518 can include a chamfered internal surface 516a configured to seat the o-ring 552 between the housing 516 and the base 526 to provide a seal between the base 526 and the retractor 518 when the device 500 is assembled.

Figure 37:
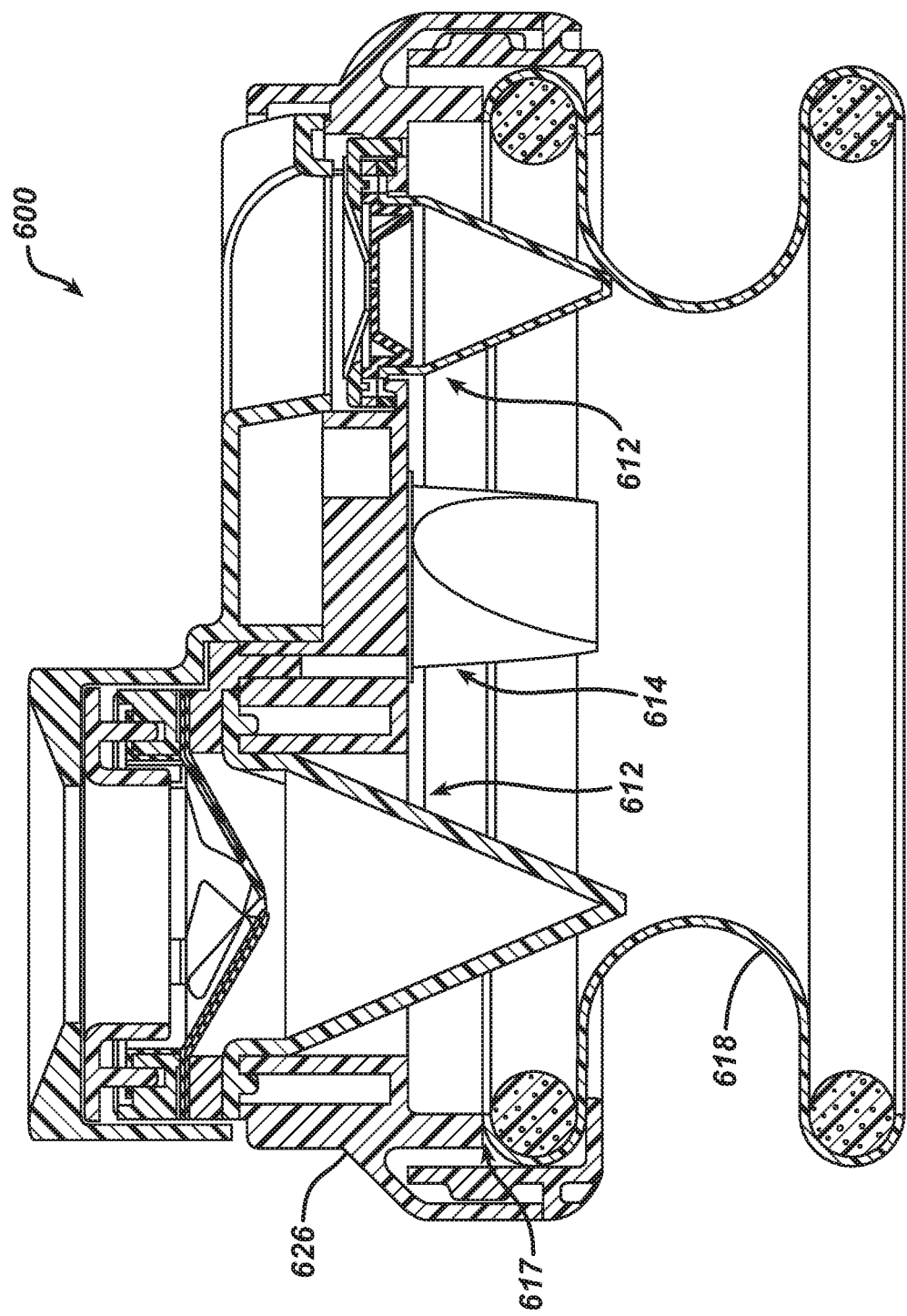
FIG. 37 is a cross-sectional view of another embodiment of a surgical access device.

In some embodiments, a surgical access can have an integrally formed seal base and housing configured to have at least one sealing port and to be removably coupled to a retractor. A surgical access device having an integrally formed seal base and housing can be easier to assemble and disassemble than a device having a separate seal base and housing. As illustrated in one embodiment of a surgical access device 600, shown in FIG. 37, an integral seal base and housing 626 can have at least one fixed sealing port 612 disposed therethrough and at least one movable sealing port 614 disposed therethrough. Opposed pressure surfaces 617 of the integral base and housing 626 and the retractor 618 can be configured to provide a pressure seal 617 to help provide a seal between the integral base and housing 626 and a retractor 618. The opposed pressure surfaces 617 can be configured to engage each other when the integral base and housing 626 is attached to the retractor 618 using an engagement and release mechanism, e.g., a bayonet latch mechanism as shown in this embodiment.

As surgical instruments are inserted through the surgical access device embodiments described herein, a risk can exist that a particularly sharp instrument may tear or puncture a portion of the retractor or nearby tissue. Accordingly, in any and all of the embodiments described herein, a safety shield can optionally be included to reduce the risk of tearing or puncture by a surgical instrument. In general the shield can be of a material that is relatively smooth and with a low coefficient of friction to allow ease of passage of instruments, but resistant to tearing and puncture. For example, the shield can be formed of silicone, urethane, thermoplastic elastomer, rubber, polyolefins, polyesters, nylons, fluoropolymers, and any other suitable materials known in the art. The shield can generally provide a liner for a retractor or tissue and can be detachable from a surgical access device so it can be used as needed in a particular procedure.

Figure 38:
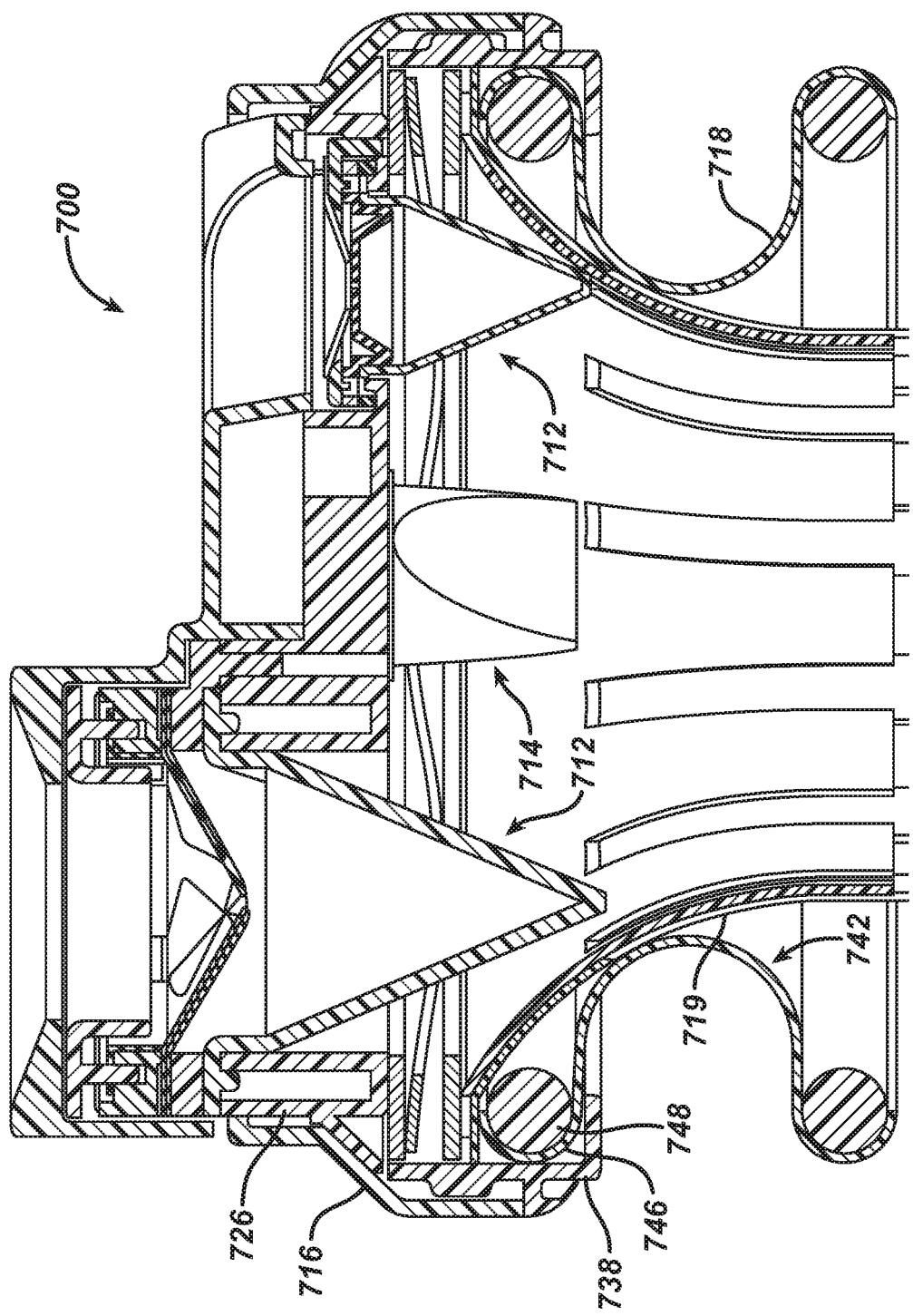
FIG. 38 is a cross-sectional view of yet another embodiment of a surgical access device including one embodiment of a safety shield.
Figure 39:
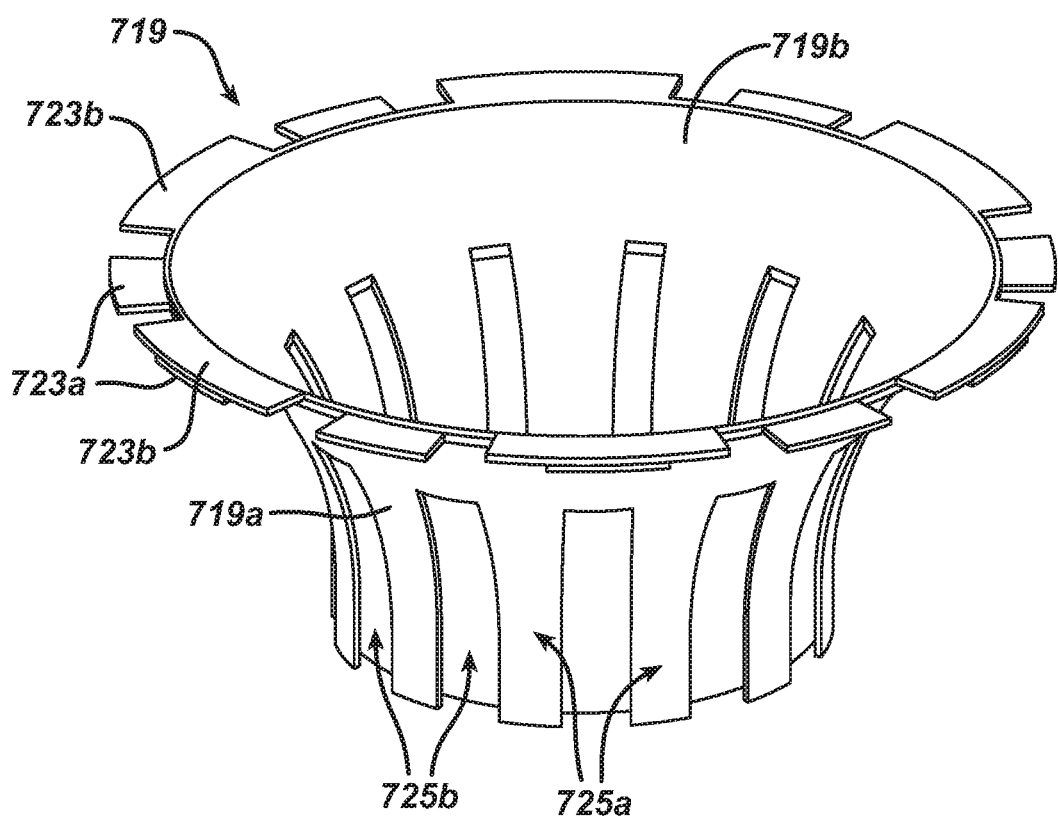
FIG. 39 is a perspective view of the safety shield of FIG. 38.
Figure 40:
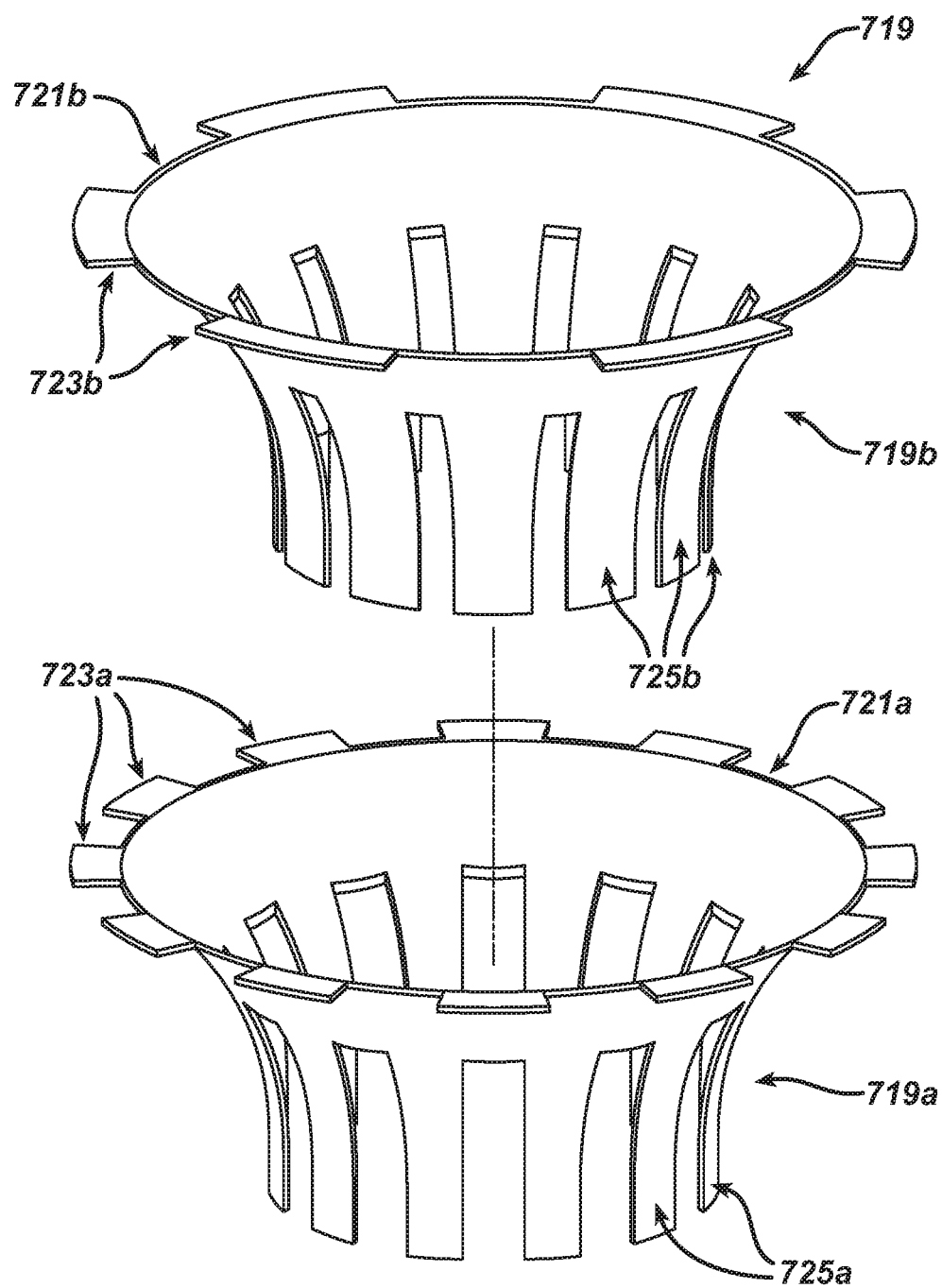
FIG. 40 is an exploded view of the safety shield of FIG. 38.

In one exemplary embodiment shown in FIGS. 38-40, a surgical access device 700 has a housing 416, a seal base 726 with at least one fixed sealing port 712 and at least one movable sealing port 714 extending therethrough, and a retractor 718. The surgical access device 700 can also include a shield 719 configured to extend through the retractor 718 to thereby provide a protective lining as surgical instruments are inserted through the device 700. The shield 719 can have a length corresponding to a length of the retractor 718, but can also have a length less than or considerably longer than the length of the retractor depending on a specific application. The shield 719 can be mated to the retractor 718 using any attachment mechanism, e.g., adhesive, screws, press fit, etc., as will be appreciated by a person skilled in the art. As illustrated, the shield 719 can be configured to engage a proximal flange 746 seated in a proximal retractor base 738 of the retractor 718 that has a proximal o-ring 748 disposed therein. The proximal o-ring 748 can help provide structure to the proximal flange 746 and therefore help provide a more stable engagement surface for the shield 719.

The shield 719 can have any size, shape, and configuration. In this illustrated embodiment, the shield 719 includes a circumferentially expandable, cylindrically-shaped member having an outer layer 719a and an inner layer 719b configured to be disposed within in the outer layer 719a. The outer and inner layers 719a, 719b can each respectively include a circumferential proximal rim 721a, 721b having a plurality of flanges 723a, 723b extending radially outward therefrom. The outer and inner layers 719a, 719b can include any number of flanges 723a, 723b, and the flanges 723a, 723b can be spaced equidistantly or any other distance apart from one another around their respective proximal rims 721a, 721b. The outer and inner flanges 723a, 723b can each be configured to at least partially overlap to form a continuous proximal flange of the shield 719 that is configured to engage the proximal flange 746. Alternatively, as shown, a portion of the outer and inner flanges 723a, 723b can be configured to engage one another to form a "broken" proximal flange of the shield 719. In other embodiments, none of the outer and inner flanges 723a, 723b can overlap one another when the inner layer 719b is disposed in the outer layer 719a.

The outer and inner layers 719a, 719b of the shield 719 can also include a plurality of respective distal elongate fingers 725a, 725b distally extending from the proximal rim 721a, 721b and configured to at least partially overlap and engage one another when the inner layer 719b is disposed in the outer layer 719a to form a continuous distal surface configured to engage at least a portion of an inner wall of an inner elongate portion 742 of the retractor 718. The distal fingers 725a, 725b can thus be configured to protect the inner elongate portion 742 of the retractor 718 from damage but be configured to be selectively movable when in contact with a surgical instrument such that the surgical instrument can optionally push between the distal fingers 725a, 725b to help provide the surgical instrument with free angular range of motion through the device 700. The distal fingers 725a, 725b can also be configured to be selectively movable when the retractor 718 bends when in position in tissue, if the retractor 718 is flexible.

Figure 41:
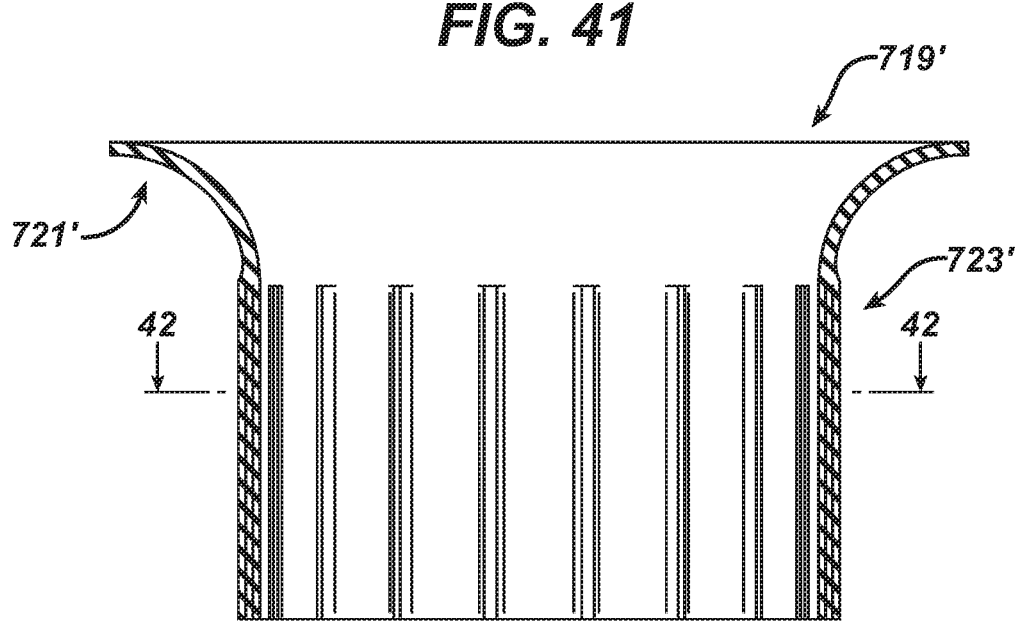
FIG. 41 is a cross-sectional side view of a second embodiment of a safety shield.
Figure 42:
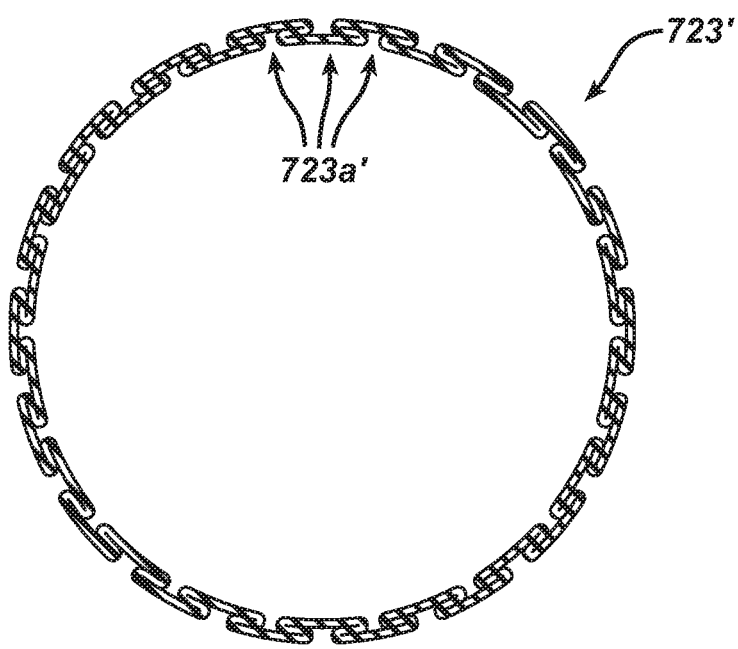
FIG. 42 is a cross-sectional top view of the safety shield of FIG. 41.
Figure 43:
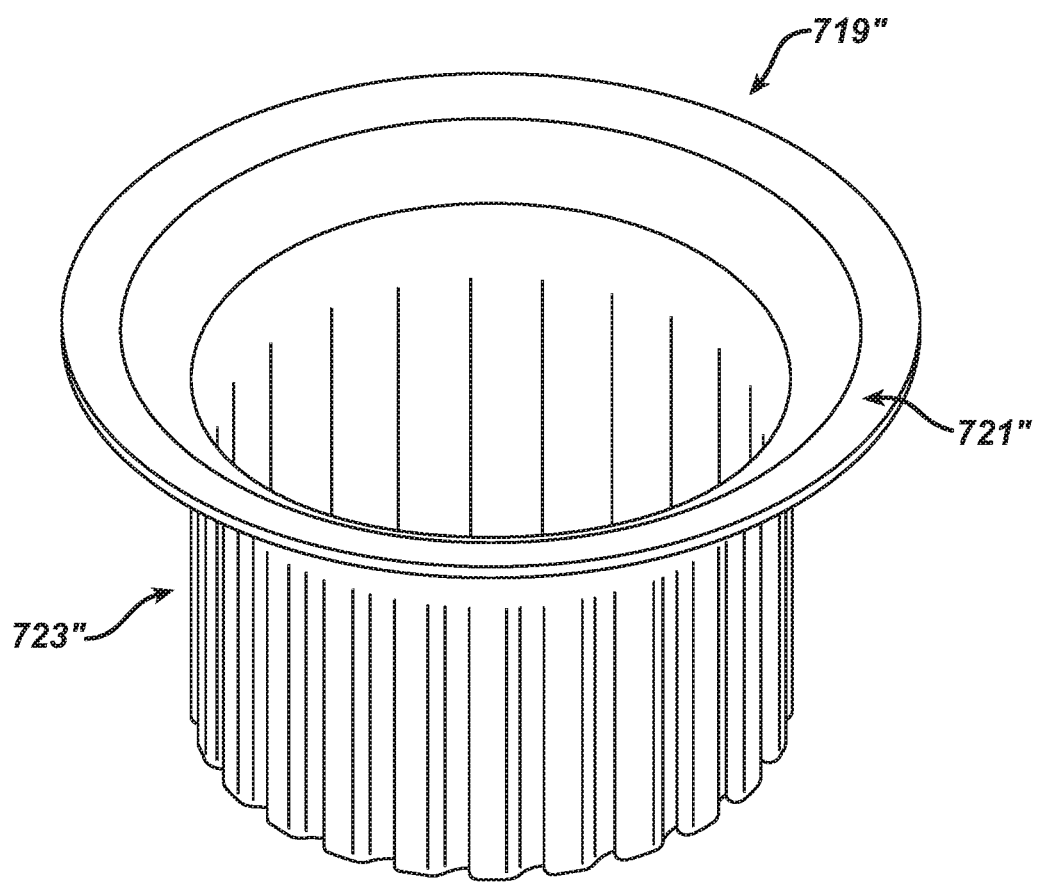
FIG. 43 is a perspective view of a third embodiment of a safety shield.
Figure 44:
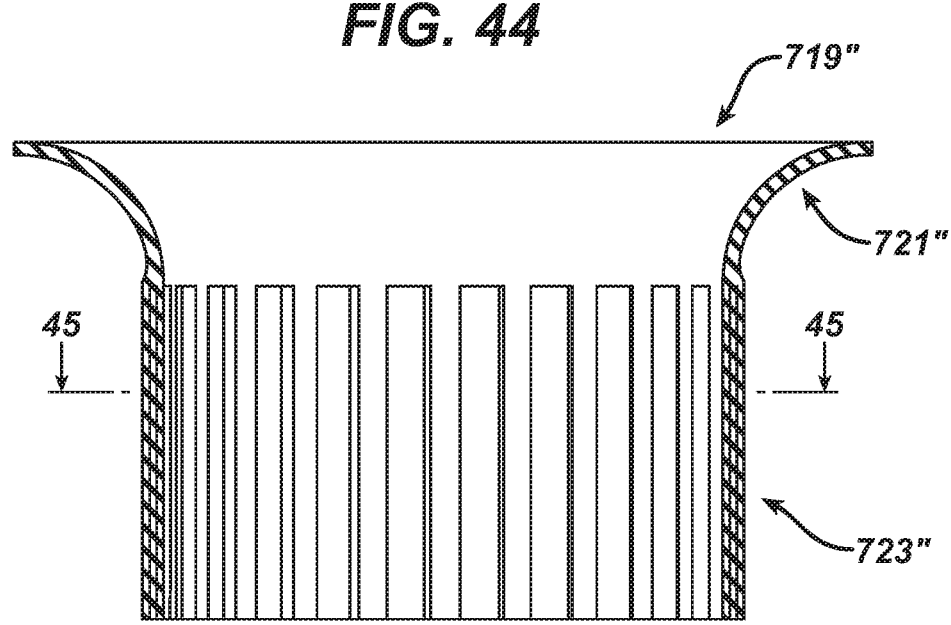
FIG. 44 is a cross-sectional side view of the safety shield of FIG. 43.
Figure 45:
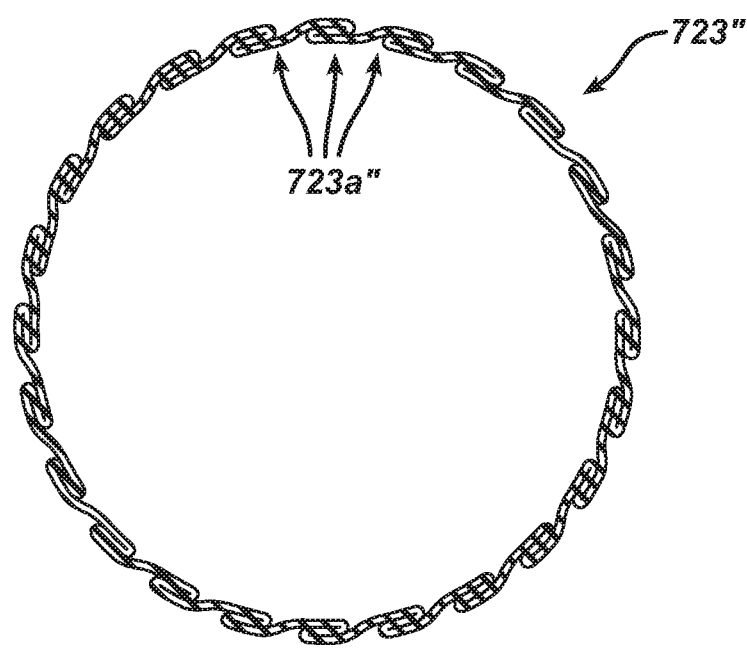
FIG. 45 is a cross-sectional top view of the safety shield of FIG. 43.

A shield can include a plurality of layers as discussed above, or a shield can be a singular member, which can make the shield easier to dispose in a retractor. FIGS. 41 and 42 illustrate one embodiment of a singular shield 719'. The alternate shield 719' can include a circumferential proximal rim 721' with or without radially extending flanges. Instead of having a plurality of fingers distally extending from the proximal rim 721', the alternate shield 719' can include a pleated distal portion 723' that simulates distal fingers. The pleated distal portion 723' can have a variety of sizes, shapes, and configurations. As shown, the pleated distal portion 723' can include a plurality of box pleats 723a' folded in the shield 719' circumferentially around the distal portion 723'. In this way, the pleated distal portion 723' can be configured to be selectively movable when the retractor 719' bends, if the retractor 719' is flexible, and/or when a surgical instrument presses against an inner wall of the pleated distal portion 723'. In another embodiment of a singular retractor shield 719", shown in FIGS. 43-45, the shield 719" can include a pleated distal portion 723" distally extending from a proximal rim 721" and having a plurality of knife pleats 723a" formed circumferentially therearound.

In the surgical access device embodiments described above, each of the device's surgical access ports can be configured to move relative to the retractor through movement of the seal base and/or movement of a movable sealing port. However, in some surgical procedures it can be advantageous to have at least one surgical access port configured to stay in a fixed radial position relative to the retractor. For example, during a surgical procedure tissue can be retracted away from a surgical site to provide more direct access to the surgical site and to protect the retracted tissue from damage during the surgical procedure. Because the retracted tissue is traditionally retracted in a stable position throughout a surgical procedure, a retractor surgical instrument used to retract tissue also traditionally remains in a stable position throughout a surgical procedure, e.g., by continuous hand holding of the retractor, by mounting a retractor to a wall fixture, etc. Accordingly, in any and all of the embodiments described herein, a side access port can optionally be included to allow a surgical instrument to be inserted through the surgical access device but remain in a fixed radial position relative to the retractor of the surgical access device to, e.g., hold retracted tissue in a stable position even during movement of the seal base or other portion of the surgical access device.

Figure 46:
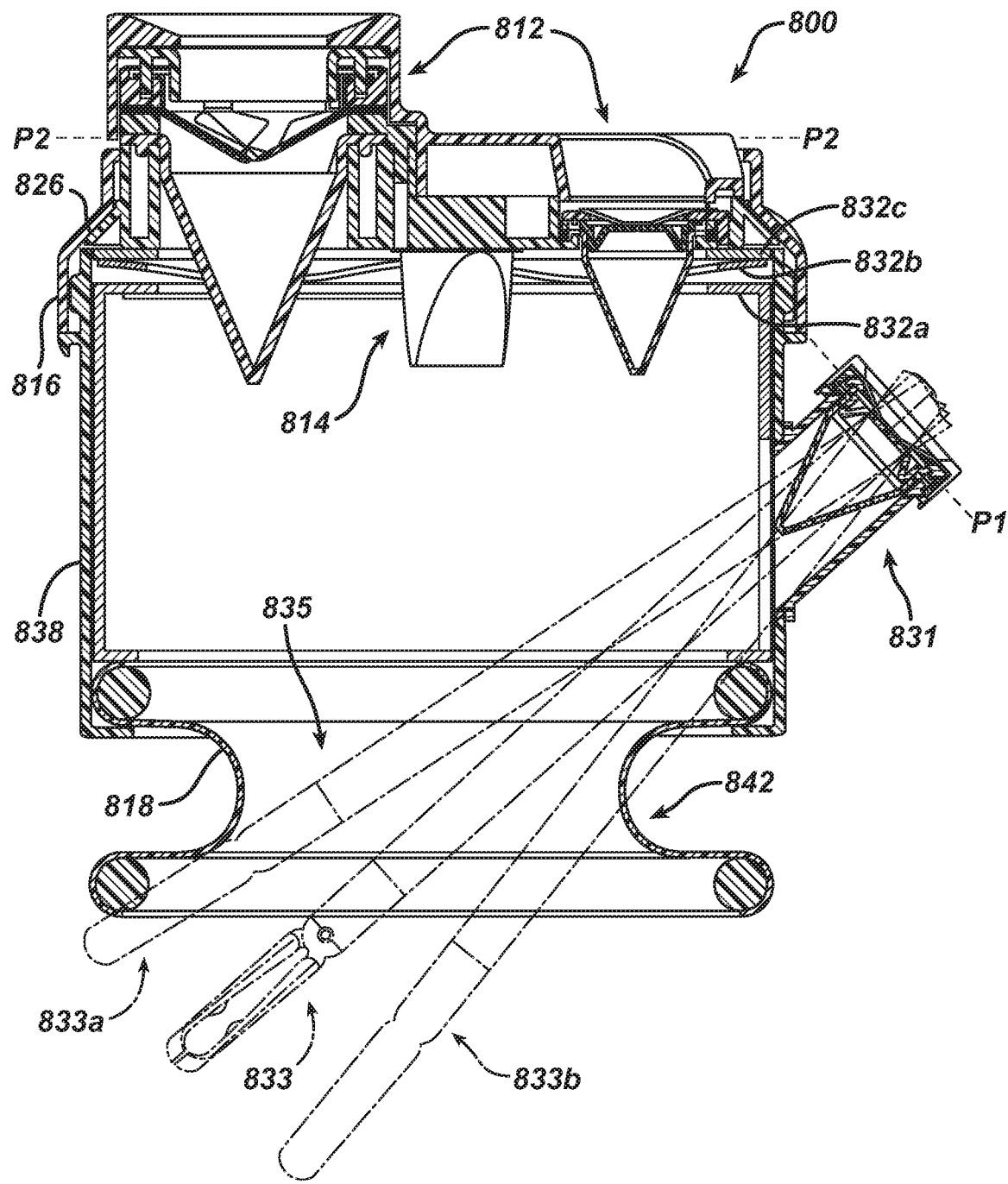
FIG. 46 is a cross-sectional view of another embodiment of a surgical access device including one embodiment of a side access port with a surgical instrument inserted therethrough.
Figure 47:
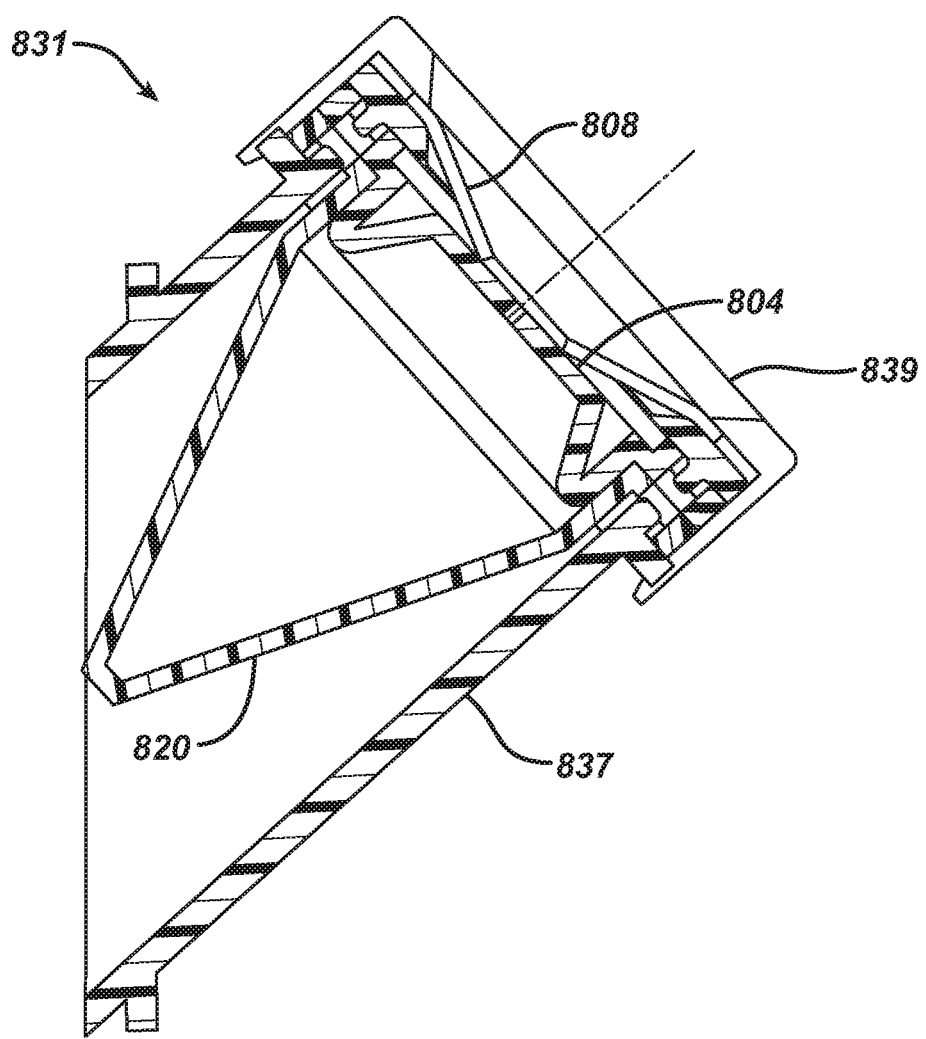
FIG. 47 is a cross-sectional view of the side access port of FIG. 46.
Figure 48:
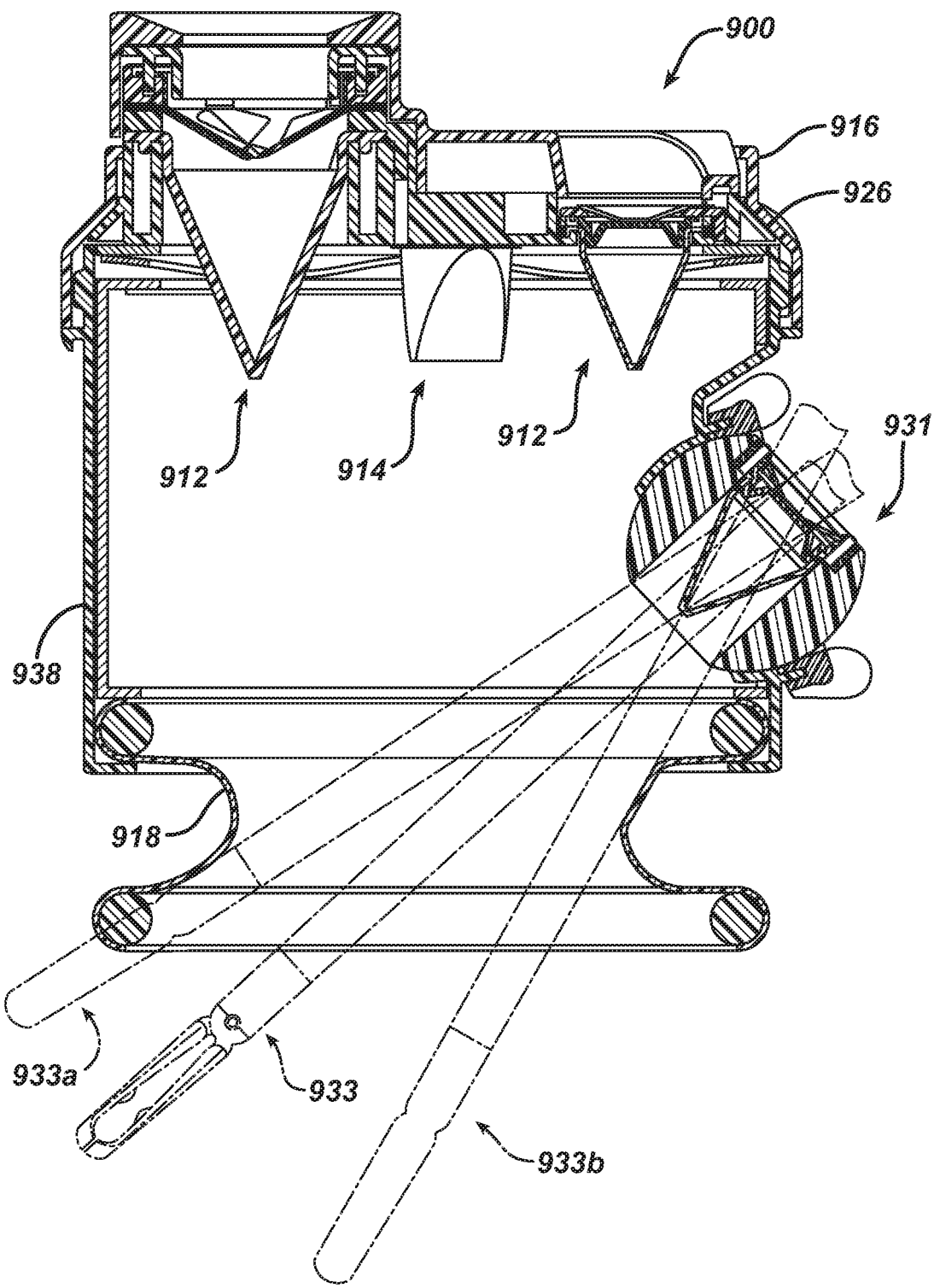
FIG. 48 is a cross-sectional view of yet another embodiment of a surgical access device including another embodiment of a side access port with a surgical instrument inserted therethrough.
Figure 49:
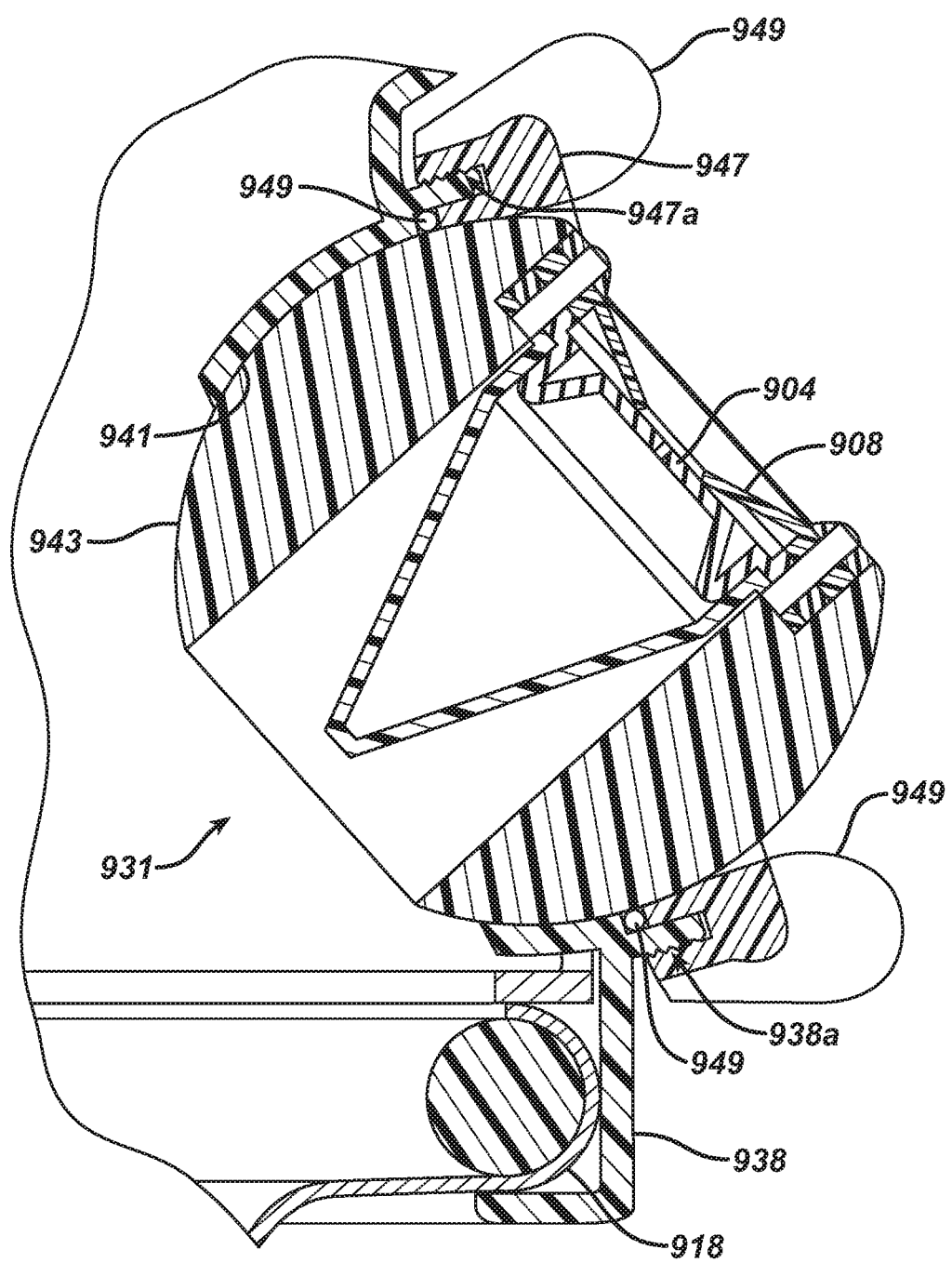
FIG. 49 is a partial cross-sectional view of the side access port and the device of FIG. 48.
Figure 50:
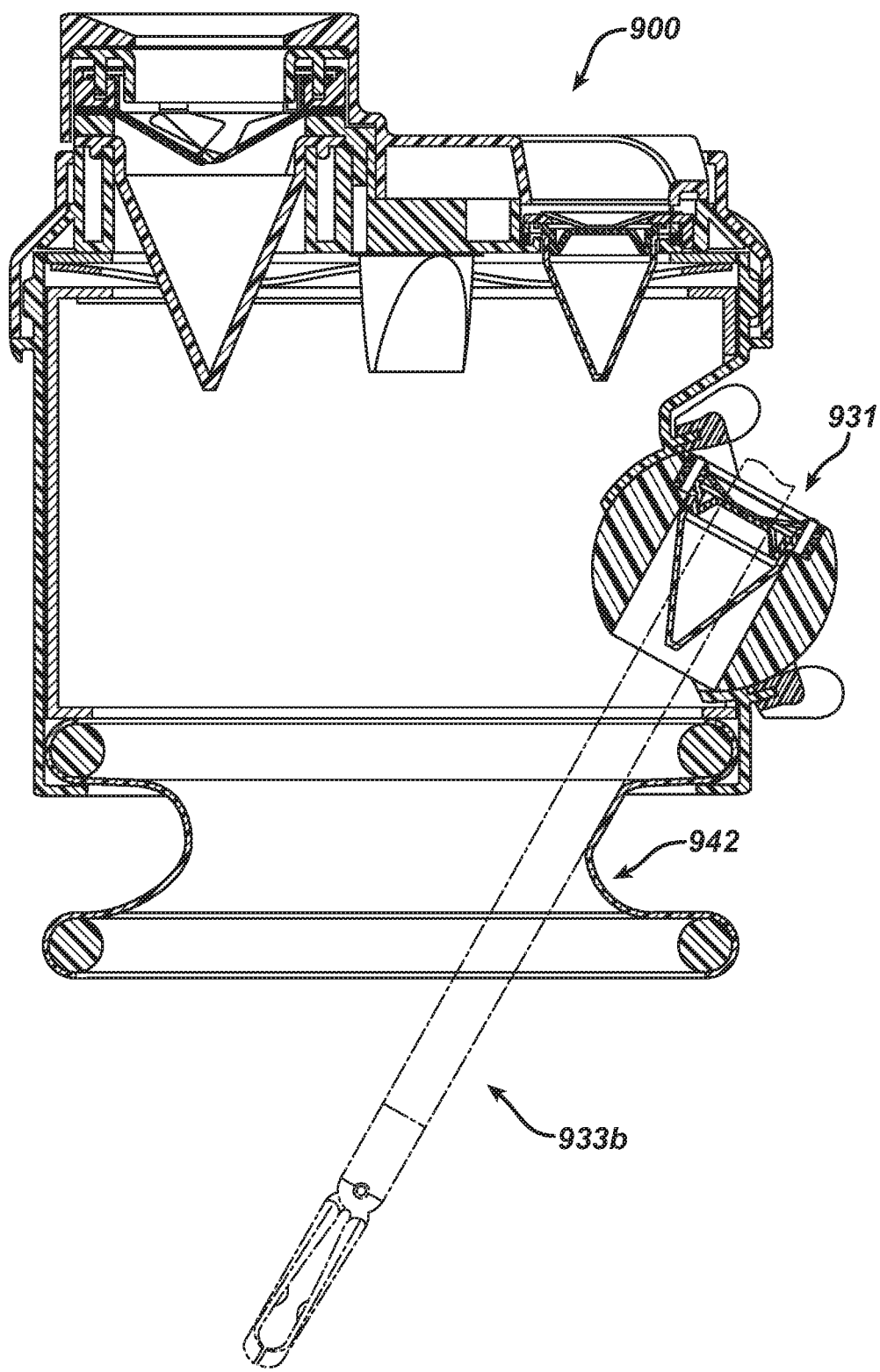
FIG. 50 is a cross-sectional view of the device of FIG. 46 with the surgical instrument inserted through the side access port in a minimized insertion position.
Figure 51:
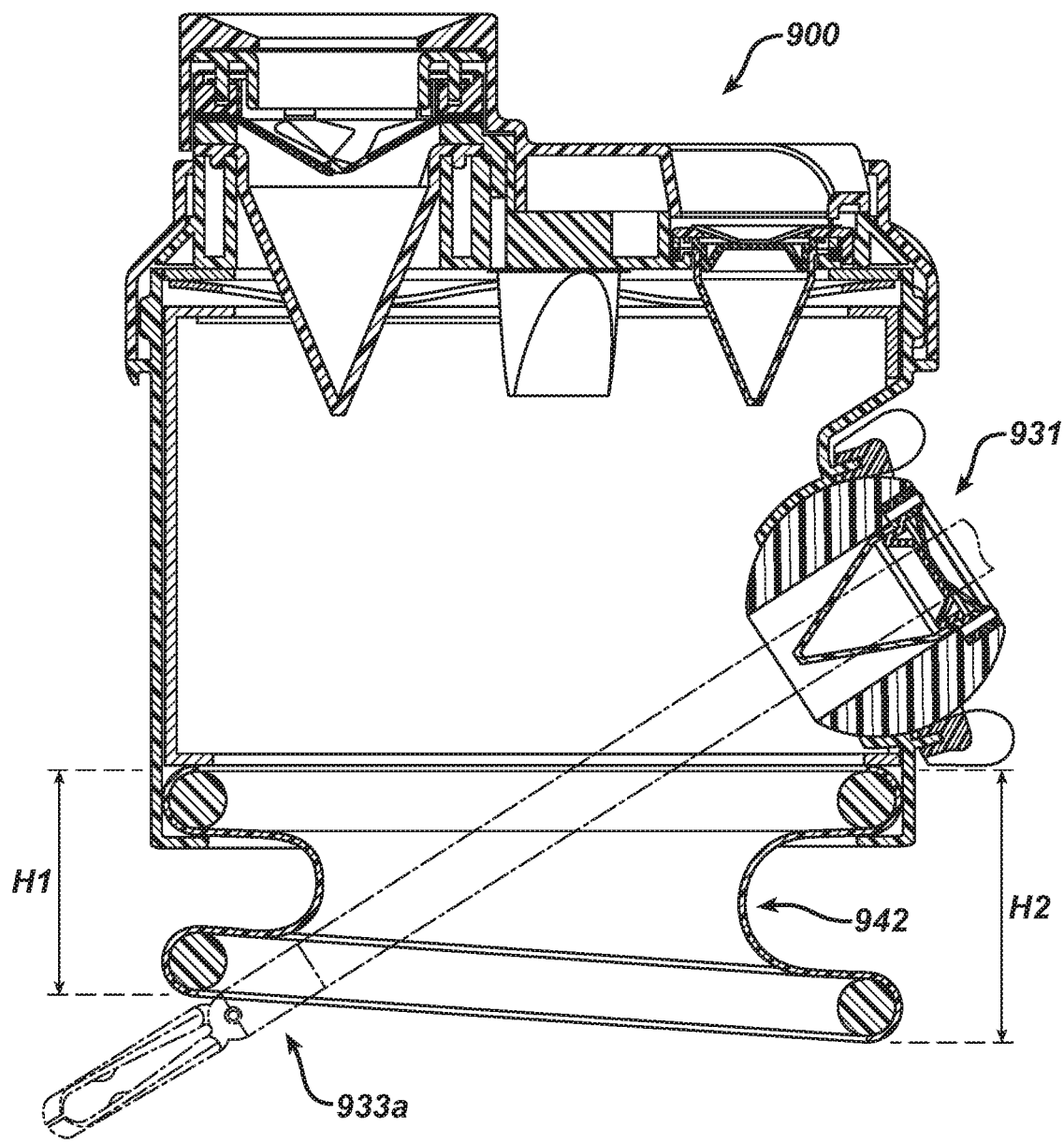
FIG. 51 is a cross-sectional view of the device of FIG. 46 with the surgical instrument inserted through the side access port in a maximized insertion position.

In one exemplary embodiment shown in FIGS. 46 and 47, a surgical access device 800 has a housing 816, a retractor 818 configured to couple with the housing 816 using an engagement and release mechanism, a seal base 826 with at least one fixed sealing port 812 and at least one movable sealing port 814 extending therethrough, and a spring assembly including distal and proximal spring retaining rings 832a, 832c with a seal spring 832b positioned therebetween. Similar to that discussed above, the housing 816 and the base 826 can be movable relative to the retractor 818, and the at least one movable sealing port 814 can be movable relative to the housing 816 and the retractor 818. The surgical access device 800 can also include a side access port 831 having a sealing element 820 disposed therein and configured to receive a surgical instrument 833 inserted therethrough. The side access port 831 can be a fixed sealing port or a movable sealing port similar to the sealing ports discussed above, although in an exemplary embodiment the side access port 831 can be a fixed sealing port similar to the fixed sealing ports 12a, 12b of the device 100 of FIG. 1. A person skilled in the art will appreciate that while a grasper 833 configured to retract tissue is shown inserted through the side access port 831, any surgical instrument can be inserted through the side access port 831 to retract tissue or perform any other function in a surgical procedure.

The side access port 831 can be formed in the retractor 818 such that the side access port 831 is located at a fixed radial position relative to the retractor 818. In the illustrated embodiment, a body 837 of the side access port 831 angles proximally upwards and outwards from a sidewall of the proximal retractor base 838 such that the side sealing element 820 extending through the body 837 points toward the retractor's working channel 835 to allow the surgical instrument 833 inserted through the side access port 831 to easily access the working channel 835. To accommodate the side access port 831, a proximal retractor base 838 of the retractor 818 can have an extended depth to allow the side access port 831 to be formed in a sidewall thereof at a fixed position around a perimeter thereof and allow the side access port 831 to provide access to a working channel 835 extending through the retractor 818. As shown, the distal spring retaining ring 832a engaging the proximal retractor base 838 can also have an extended depth to accommodate the side access port 831. Being formed in a sidewall of the retractor 818, as illustrated in FIG. 46, the side access port 831 can extend in a plane P1 that is offset from a plane P2 containing the base 826 through which the at least one fixed and movable sealing ports 812, 814 extend. The side access port 831 can extend at any angle through the retractor 818 and the distal spring retaining ring 832a with any angle between the plane P1 of the side access port 831 and the plane P2 of the base 826.

The surgical instrument 833 can have a range of motion within the side access port 831 dependent on its angle of insertion through the seal, e.g., in this embodiment a multi-layer protective member 808 disposed on a proximal surface of a conical seal 804 of the side access port 831. For example, as illustrated in FIG. 46, at a maximum angle of insertion, the instrument 833a can extend through the side access port 831 and engage an inner wall of an inner elongate portion 842 of the retractor 818 on a side opposed to the sidewall of the retractor 818 including the side access port 831. Similarly, at a minimum angle of insertion, the instrument 833b can extend through the side access port 831 and engage the inner wall of the inner elongate portion 842 on a same side as the sidewall of the retractor 818 including the side access port 831.

The side access port 831 can also include a seal cap 839 attached to a proximal end thereof. The seal cap 839 can be configured similar to the lip seal 132 of FIG. 9 and can be configured to allow insertion of the instrument 833 therethrough. The seal cap 839 can also be configured to cover and protect the side access port 831 when the side access port 831 is not in use, e.g., when the instrument 833 is not disposed therethrough. The seal cap 839 can be removably coupled to the side access port 831, e.g., with a snap lock, for cleaning and/or replacement.

In some embodiments, a surgical access device can include a side access port that is at a fixed radial position relative to the device's retractor but that is otherwise movable relative to the retractor. As illustrated in one embodiment in FIGS. 48-51, a surgical access device 900 can include a housing 916, a retractor 918, a seal base 926 with at least one fixed sealing port 912 and at least one movable sealing port 914 extending therethrough, and a spring assembly similar to the device 800 of FIG. 46, but the alternate device 900 can include a radially fixed but rotationally and pivotally movable side access port 931 formed in a sidewall of the retractor 918 in a proximal retractor base 938.

The movable side access port 931 can be configured to be movable relative to the retractor 918 in a variety of ways, such as by using a ball and socket joint as illustrated. The retractor 918 can include a socket 941 configured to seat a ball 943 of the movable side access port 931 that allows the ball 943 to slide or rotate therein. The device 900 can include a releasable locking mechanism configured to lock the ball 943 in a fixed position relative to the socket 941 and the retractor 918 and to be released to allow the ball 943 to move relative to the socket 941 and the retractor 918. The releasable locking mechanism can have a variety of configurations, e.g., engaging pins and holes, threads, a latch, a clamp, etc. In the illustrated embodiment, the releasable locking mechanism includes complementary threads 938a, 947a respectively formed on the proximal retractor base 938 and on a seal cap 947. The ball 943 can be adjusted to a desired position within the socket 941 with the seal cap 947 detached from the retractor 918 or partially threaded onto the retractor 918. When the ball 943 and hence the side access port 931 has been adjusted to a desired position, the seal cap 947 can be tightened onto the proximal retractor base 938, e.g., by rotating the seal cap 947 clockwise relative to the retractor 918, to hold the ball 943 in place until the seal cap 947 is loosened, e.g., by rotating the seal cap 947 counter clockwise relative to the retractor 918. The seal cap 947 can optionally include finger grips 951 and/or other gripping mechanism, e.g., a textured surface, finger loops, etc., to help in rotating the seal cap 947. A seal can be formed between the seal cap 947 and the retractor 918 in any way, e.g., with an o-ring 949 positioned between the seal cap 946 and the proximal retractor base 938.

Allowing movement of the side access port 931 relative to the retractor 918 while maintaining a fixed radial position relative to the retractor 918 can allow an instrument 933 inserted through the movable side access port 931 to have a greater range of available motion. A person skilled in the art will appreciate that while a grasper 933 configured to retract tissue is shown inserted through the side access port 931, any surgical instrument can be inserted through the side access port 931 to retract tissue or perform any other function in a surgical procedure. The surgical instrument 933 can have a range of motion within the side access port 931 dependent on its angle of insertion through a multi-layer protective member 908 disposed on a proximal surface of a conical seal 904 of the side access port 931 and on a rotated position of the ball 943 relative to the socket 941. For example, at a maximum angle of insertion, the instrument 933a can extend through the side access port 931 and engage an inner wall of an inner elongate portion 942 of the retractor 918 on a side opposed to the sidewall of the retractor 918 including the side access port 931. Similarly, at a minimum angle of insertion, the instrument 933b can extend through the side access port 931 and engage the inner wall of the inner elongate portion 942 on a same side as the sidewall of the retractor 918 including the side access port 931. Because a sealing element 920 of the side access port 931 can be configured to move with the ball 943 relative to the retractor 918, the sealing element 920 can maintain a fixed, predictable position such that the instrument 933 inserted through the ball 943 and the sealing element 920 can extend transversely through the ball 943 regardless of the ball's position relative to the retractor 918. If the inner elongate portion 942 is flexible as in this illustrated embodiment, the retractor 918 can be configured to deform or bend in response to pressure from the instrument 933, and/or any other instrument inserted therethrough. For non-limiting example, with the instrument 933 in a maximized insertion position, the retractor 918 can have a first height H1 in one portion of the retractor 918 and a second, larger height H2 in another portion of the retractor 918.

As will be appreciated by those skilled in the art, any and all of the embodiments disclosed herein can be interchangeable with one another as needed. For example, an exemplary surgical access device kit could include multiple housings and seal bases with one or more retractors. Each seal base and housing combination can have different movable sealing port configurations enabling various combinations of movable sealing port movement as needed in particular application. Various release mechanism known in the art can be used to releasably attach the various base members and housings to a retractor.

There are various features that can optionally be included with any and all of the surgical access device embodiments disclosed herein. For example, a component of the device, such as a seal base, housing, retractor, etc., can have one or more lights formed thereon or around a circumference thereof to enable better visualization when inserted within a patient. As will be appreciated, any wavelength of light can be used for various applications, whether visible or invisible. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. application Ser. No. 12/242,333 entitled "Methods and Devices for Performing Gastrectomies and Gastroplasties" filed on Sep. 30, 2008; U.S. application Ser. No. 12/242,353 entitled "Methods and Devices for Performing Gastrectomies and Gastroplasties" filed on Sep. 30, 2008; and U.S. application Ser. No. 12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a seal base, a housing, a proximal retractor base, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   advancing a distal end of a first surgical instrument from outside a body of a patient such that the distal end of the first surgical instrument is located within the body of the patient, wherein an elongate shaft of the first surgical instrument is positioned in a single elongate tube that is positioned in an opening of the patient, and a seal is formed around the first surgical instrument in the elongate tube;
   advancing a distal end of a second surgical instrument from outside the body of the patient such that the distal end of the second surgical instrument is located within the body of the patient, wherein an elongate shaft of the second surgical instrument is positioned in the elongate tube, and a seal is formed around the second surgical instrument in the elongate tube;
   advancing a distal end of an imaging device from outside the body of the patient such that the distal end of the imaging device is located within the body of the patient, wherein an elongate shaft of the imaging device is positioned in the elongate tube, and a third seal is formed around the imaging device in the elongate tube;
   with the distal ends of the first surgical instrument, second surgical instrument, and imaging device located within the body of the patient, rotating the first and second surgical instruments and the imaging device as a unit about a longitudinal axis of the elongate tube;
   with the distal ends of the first surgical instrument, second surgical instrument, and imaging device located within the body of the patient, moving the distal end of the first surgical instrument at an angle relative to the elongate tube and the distal end of the second surgical instrument; and
   with the distal ends of the first surgical instrument, second surgical instrument, and imaging device located within the body of the patient, moving the distal end of the second surgical instrument at an angle relative to the elongate tube and the distal end of the first surgical instrument;
   wherein the opening is a natural orifice of the patient or is a minimally invasive incision formed in tissue of the patient.

2. The method of claim 1, wherein a first sealing element forms the seal around the first surgical instrument;
   a second sealing element forms the seal around the second surgical instrument;
   a third sealing element forms the seal around the imaging device; and
   the first, second, and third sealing elements rotate with the imaging device and the first and second surgical elements about the longitudinal axis of the elongate tube.

3. The method of claim 2, further comprising, with the first seal forming the seal around the first surgical instrument, rotating the first sealing element relative to the second sealing element, the second surgical instrument, and the elongate tube, wherein the rotation of the first sealing element is about a first axis that is laterally offset from the longitudinal axis of the elongate tube; and
   with the second seal forming the seal around the second surgical instrument, rotating the second sealing element relative to the first sealing element, the first surgical instrument, and the elongate tube, wherein the rotation of the second sealing element is about a second axis that is laterally offset from the first axis and from the longitudinal axis of the elongate tube.

4. The method of claim 2, wherein the rotation of the first sealing element is 360°, and the rotation of the second sealing element is 360°.

5. The method of claim 2, wherein the first, second, and third sealing elements are seated in a base, and the base also rotates as a unit with the first and second surgical instruments.

6. The method of claim 1, wherein the rotation is 360°.

7. The method of claim 1, further comprising releasably attaching the elongate tube to a proximal housing member;
   after the operative coupling of the elongate tube to the proximal housing member, positioning the elongate tube in the opening, the proximal housing member being located entirely proximal to the opening;
   removing the elongate tube from the opening; and after removing the elongate tube from the opening, detaching the elongate tube from the proximal housing member.

8. The method of claim 1, wherein each of the first and second surgical instruments includes a grasper.

9. A surgical method, comprising:
positioning a retractor within tissue of a patient to provide access through the tissue to a body cavity of the patient;
advancing a first surgical instrument through a first sealing element disposed in a first opening formed in a base and then advancing the first surgical instrument through a working channel extending through the retractor, the first sealing element forming a seal around the first surgical instrument; and
advancing a second surgical instrument through a second sealing element disposed in a second opening formed in a sidewall of an intermediate base located between and coupled to the base and the retractor, the second sealing element forming a seal around the second surgical instrument;
wherein the first sealing element has a first longitudinal axis, the working channel has a second longitudinal axis that is substantially parallel to the first longitudinal axis, and the second sealing element has a third longitudinal axis that is angularly offset from the first and second longitudinal axes.

10. The method of claim 9, wherein the first surgical instrument extends through the first sealing element simultaneously with the second surgical instrument extending through the second sealing element.

11. The method of claim 9, further comprising rotating the base relative to the intermediate base with the first surgical instrument extending through the first sealing element.

12. The method of claim 9, further comprising rotating the first sealing element within the first opening relative to the base and the intermediate base with the first surgical instrument extending through the first sealing element.

13. The method of claim 9, further comprising advancing a third surgical instrument through a third sealing element disposed in a third opening formed in the base and then advancing the third surgical instrument through the working channel extending through the retractor, the third sealing element forming a seal around the third surgical instrument;
wherein the third opening has a fourth longitudinal axis that is substantially parallel to the first and second longitudinal axes and is angularly offset from the third longitudinal axis.

14. The method of claim 9, further comprising moving the second sealing element within the second opening so as to change the angular offset of the third longitudinal axis relative to the first and second longitudinal axes.

15. The method of claim 9, wherein the second sealing element is seated at a fixed position in the second opening such that the angular offset of the third longitudinal axis is fixed relative to the intermediate base.

16. A method of using a surgical device, comprising:
mating a proximal housing to a distal retractor configured to provide a pathway through tissue of a patient, thereby capturing a base between the proximal housing and the distal retractor;
with the proximal housing mated to the distal retractor, rotating the base 360° about a central point of the base relative to the proximal housing and the distal retractor;
with the proximal housing mated to the distal retractor, rotating a first sealing element seated in a first opening in the base 360° about a central point of the first opening relative to the proximal housing, the distal retractor, and a second opening in the base having a second sealing element seated therein, the first sealing element being configured to form a seal around a first surgical instrument advanced therethrough, and the second sealing element being configured to form a seal around a second surgical instrument advanced therethrough;
with the proximal housing mated to the distal retractor, rotating the second sealing element 360° about a central point of the second opening relative to the proximal housing, the distal retractor, and the first opening; and
removing the proximal housing from the distal retractor, thereby releasing the base from between the proximal housing and the distal retractor.

17. The method of claim 16, further comprising, with the proximal housing mated to the distal retractor, moving the first sealing element laterally in a plane parallel to a plane defined by the base, thereby changing a distance between the first sealing element and the central point of the base.

18. The method of claim 16, wherein mating the proximal housing to the distal retractor captures a spring assembly between the base and the distal retractor, the spring assembly forming a seal between the base and the distal retractor.

19. The method of claim 16, wherein the central point of the second sealing port is laterally offset from the central point of the base and is laterally offset from the central point of the first opening.

20. The method of claim 16, further comprising positioning the distal retractor in the tissue of the patient.

* * * * *